(12) United States Patent
Wilson et al.

(10) Patent No.: US 11,219,566 B2
(45) Date of Patent: Jan. 11, 2022

(54) MULTIMODALITY MEDICAL PROCEDURE MATTRESS-BASED DEVICE

(71) Applicant: Egg Medical, Inc., Arden Hills, MN (US)

(72) Inventors: Robert F. Wilson, Roseville, MN (US); John P. Gainor, Mendota Heights, MN (US); Uma S. Valeti, St. Paul, MN (US)

(73) Assignee: Egg Medical, Inc., Arden Hills, MN (US)

( * ) Notice: Subject to any disclaimer, the term of this patent is extended or adjusted under 35 U.S.C. 154(b) by 0 days.

(21) Appl. No.: 16/989,850

(22) Filed: Aug. 10, 2020

(65) Prior Publication Data

US 2020/0368086 A1 Nov. 26, 2020

Related U.S. Application Data

(63) Continuation of application No. 14/961,822, filed on Dec. 7, 2015, now abandoned.
(Continued)

(51) Int. Cl.
*A61G 7/05* (2006.01)
*A61G 13/10* (2006.01)
(Continued)

(52) U.S. Cl.
CPC .............. *A61G 7/05* (2013.01); *A61B 6/0407* (2013.01); *A61B 6/107* (2013.01); *A61B 6/503* (2013.01);
(Continued)

(58) Field of Classification Search
CPC ...... A61G 7/05; A61G 7/0524; A61G 7/0503; A61G 7/072; A61G 7/075; A61G 13/101; A61G 13/107; A61G 13/121; A61G 1/01; A61G 1/013; A61G 12/008; A61G 2205/60; A61G 2210/50; A61G 2210/90;
(Continued)

(56) References Cited

U.S. PATENT DOCUMENTS 3,984,696 A * 10/1976 Collica ................... A61B 6/107
 250/519.1
4,062,518 A * 12/1977 Stivender ................. A61B 6/04
 250/519.1
(Continued)

FOREIGN PATENT DOCUMENTS

CN 203 408 059 U 1/2014
DE 196 27 645 A1 1/1998
(Continued)

OTHER PUBLICATIONS

EPO, European Search Report for EP Application No. 15 865 511.8 dated Jan. 16, 2018, 12 pages.

*Primary Examiner* — Robert G Santos
*Assistant Examiner* — Rahib T Zaman
(74) *Attorney, Agent, or Firm* — Inskeep IP Group, Inc.

(57) ABSTRACT

A mattress system is provided that is optimized for the hospital setting and includes a guiderail system that accepts a variety of accessories for attachment thereto. The guiderail system may have integrated data lines, power lines, gas lines, and/or fluid lines. Also provided are radioabsorbant shields, trays and other components designed for optimal use with the mattress system.

16 Claims, 40 Drawing Sheets

Related U.S. Application Data

(60) Provisional application No. 62/088,495, filed on Dec. 5, 2014, provisional application No. 62/240,409, filed on Oct. 12, 2015.

(51) Int. Cl.

| | | |
|---|---|---|
| *A61G 7/07* | (2006.01) | |
| *A61G 13/12* | (2006.01) | |
| *A61B 6/00* | (2006.01) | |
| *A61B 6/04* | (2006.01) | |
| *A61G 7/075* | (2006.01) | |
| *A61B 6/10* | (2006.01) | |
| *A61G 1/01* | (2006.01) | |
| *A61M 5/14* | (2006.01) | |
| *A61H 31/00* | (2006.01) | |
| *A61G 12/00* | (2006.01) | |
| *A61G 1/013* | (2006.01) | |

(52) U.S. Cl.
CPC ......... *A61G 7/0503* (2013.01); *A61G 7/0524* (2016.11); *A61G 7/072* (2013.01); *A61G 7/075* (2013.01); *A61G 13/101* (2013.01); *A61G 13/107* (2013.01); *A61G 13/121* (2013.01); *A61B 6/0492* (2013.01); *A61B 6/102* (2013.01); *A61B 6/4423* (2013.01); *A61B 6/487* (2013.01); *A61G 1/01* (2013.01); *A61G 1/013* (2013.01); *A61G 12/008* (2013.01); *A61G 2205/60* (2013.01); *A61G 2210/50* (2013.01); *A61G 2210/90* (2013.01); *A61H 31/006* (2013.01); *A61M 5/14* (2013.01)

(58) Field of Classification Search
CPC ........ A61H 31/006; A61M 5/14; A61B 6/487; A61B 6/4423; A61B 6/102; A61B 6/0492; A61B 6/0407; A61B 6/107; A61B 6/503
See application file for complete search history.

(56) References Cited

U.S. PATENT DOCUMENTS

| | | | | |
|---|---|---|---|---|
| 4,168,554 A * | 9/1979 | Hindes | A61H 31/00 | 5/722 |
| 4,628,557 A * | 12/1986 | Murphy | A47C 27/148 | 5/699 |
| 4,770,164 A * | 9/1988 | Lach | A61H 31/005 | 601/41 |
| 4,977,630 A * | 12/1990 | Oswalt | A61G 1/00 | 297/316 |
| 5,400,448 A * | 3/1995 | Zwickey | A61G 1/04 | 128/870 |
| 5,738,637 A * | 4/1998 | Kelly | A61H 31/008 | 601/41 |
| 5,860,176 A * | 1/1999 | Norberg | A61G 1/00 | 128/870 |
| 5,981,964 A * | 11/1999 | McAuley | G21F 3/00 | 250/515.1 |
| 6,195,820 B1 * | 3/2001 | Heimbrock | A61G 13/12 | 403/68 |
| 6,278,125 B1 * | 8/2001 | Belek | G21F 3/00 | 250/519.1 |
| 6,325,538 B1 * | 12/2001 | Heesch | A61B 6/107 | 128/846 |
| 6,653,648 B2 * | 11/2003 | Goldstein | A61B 6/107 | 250/515.1 |
| 6,898,811 B2 * | 5/2005 | Zucker | A61G 1/04 | 5/603 |
| 7,226,427 B2 * | 6/2007 | Steen | A61H 31/006 | 601/44 |
| 7,276,716 B1 * | 10/2007 | Munro, III | A61N 5/1007 | 250/515.1 |
| 7,303,334 B2 * | 12/2007 | Cadwalader | A61B 6/107 | 378/203 |
| 7,347,832 B2 * | 3/2008 | Jensen | A61H 31/008 | 601/41 |
| 7,650,656 B2 * | 1/2010 | Jahrling | A61B 6/0442 | 5/601 |
| 8,132,277 B2 * | 3/2012 | Buchanan | A61G 7/00 | 5/627 |
| 8,777,879 B2 * | 7/2014 | Johnson | A61H 31/00 | 601/43 |
| 9,101,272 B2 * | 8/2015 | O'Loughlin | A61B 6/4035 | |
| 10,548,795 B2 * | 2/2020 | Conner | A61B 6/12 | |
| 2001/0044967 A1 * | 11/2001 | Gaspar | A47C 21/003 | 5/632 |
| 2002/0138904 A1 * | 10/2002 | Wong | A61G 7/0513 | 5/600 |
| 2004/0088793 A1 * | 5/2004 | Koch | A61G 13/101 | 5/621 |
| 2004/0162587 A1 * | 8/2004 | Hampton | A61H 31/006 | 607/5 |
| 2005/0011518 A1 * | 1/2005 | Biondo | A61G 7/001 | 128/204.18 |
| 2005/0166325 A1 * | 8/2005 | Tidwell | A61B 6/0485 | 5/624 |
| 2005/0236588 A1 * | 10/2005 | Ein-Gal | A61B 6/107 | 250/515.1 |
| 2006/0251219 A1 * | 11/2006 | Cadwalader | A61B 6/107 | 378/203 |
| 2007/0138415 A1 * | 6/2007 | Rees | G21F 3/02 | 250/516.1 |
| 2007/0270725 A1 * | 11/2007 | Sherman | A61H 31/00 | 601/44 |
| 2008/0301874 A1 * | 12/2008 | Salt | A61G 1/04 | 5/425 |
| 2009/0110152 A1 * | 4/2009 | Manzke | A61B 6/107 | 378/195 |
| 2009/0144903 A1 * | 6/2009 | Delvaux | A61H 31/008 | 5/617 |
| 2009/0232282 A1 * | 9/2009 | Belson | A61B 6/4423 | 378/203 |
| 2010/0192300 A1 * | 8/2010 | Tannoury | A61G 13/0036 | 5/607 |
| 2011/0047706 A1 * | 3/2011 | Hiebert | A61G 13/121 | 5/623 |
| 2013/0320246 A1 * | 12/2013 | Beck | A61M 25/00 | 250/515.1 |
| 2014/0029720 A1 * | 1/2014 | Osherov | A61B 6/4441 | 378/62 |
| 2014/0048730 A1 * | 2/2014 | Niedzielski | A61B 6/107 | 250/519.1 |
| 2014/0276269 A1 * | 9/2014 | Illindala | A61G 1/04 | 601/41 |
| 2015/0272519 A1 | 10/2015 | Buchmeyer | | |

FOREIGN PATENT DOCUMENTS

| | | | |
|---|---|---|---|
| DE | 10 2009 009838 A1 | 6/2010 | |
| DE | 10 2012 218 391 A1 | 4/2014 | |

\* cited by examiner

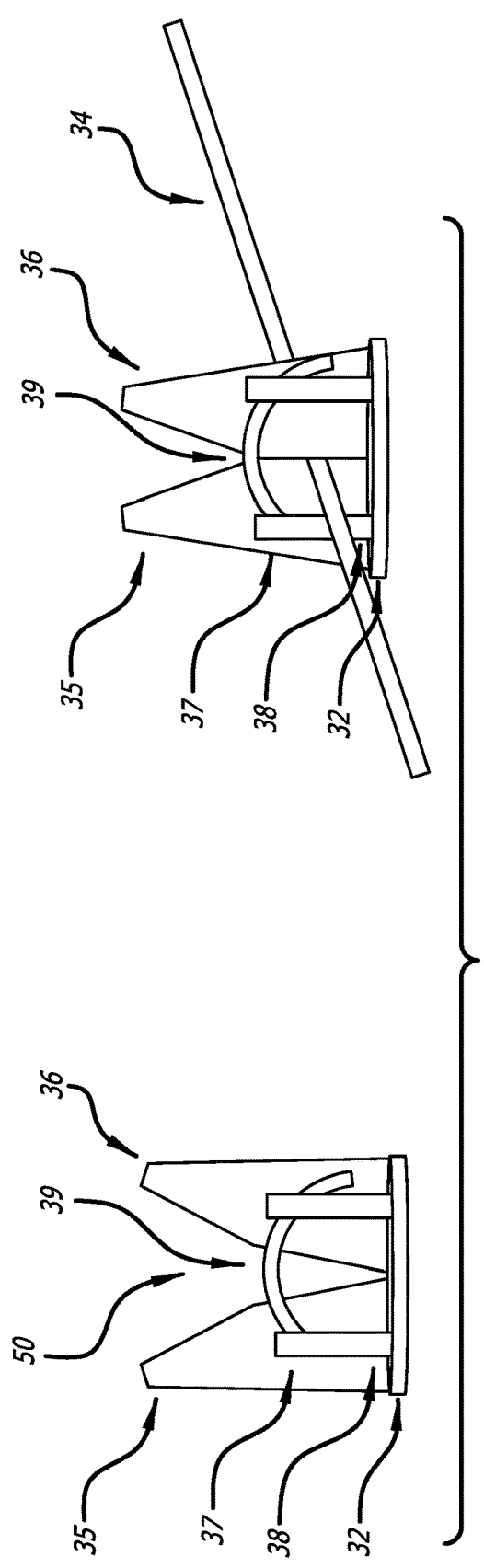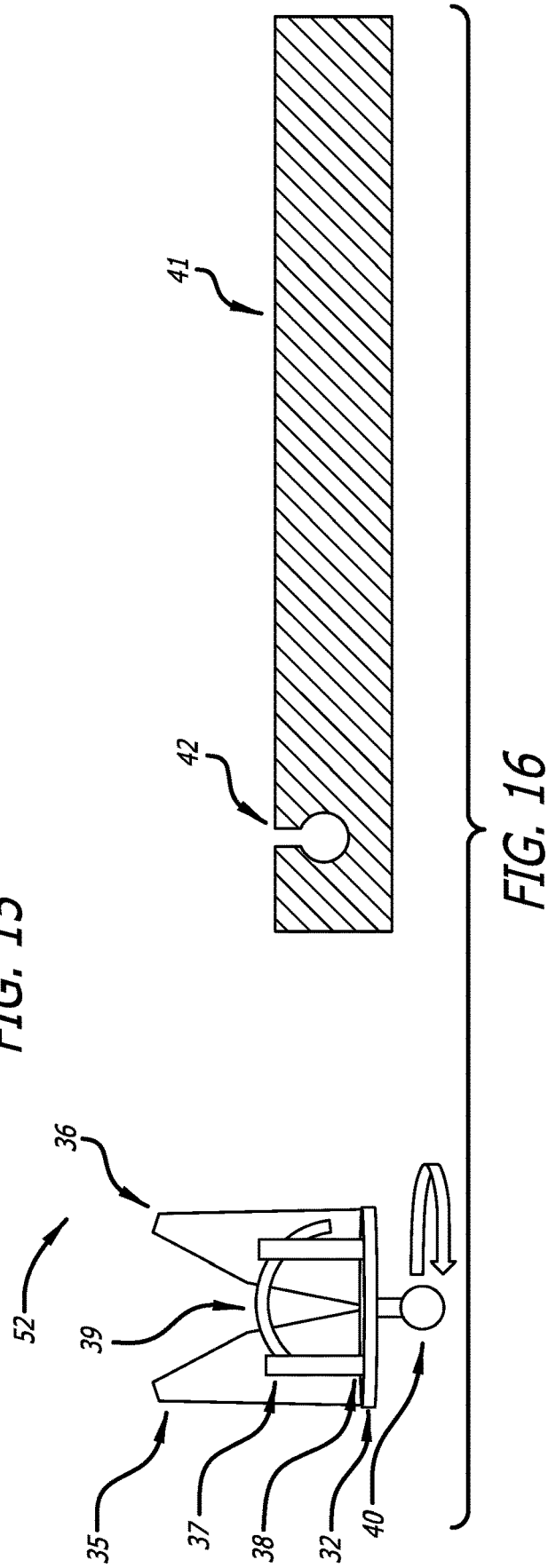
FIG. 15
FIG. 16

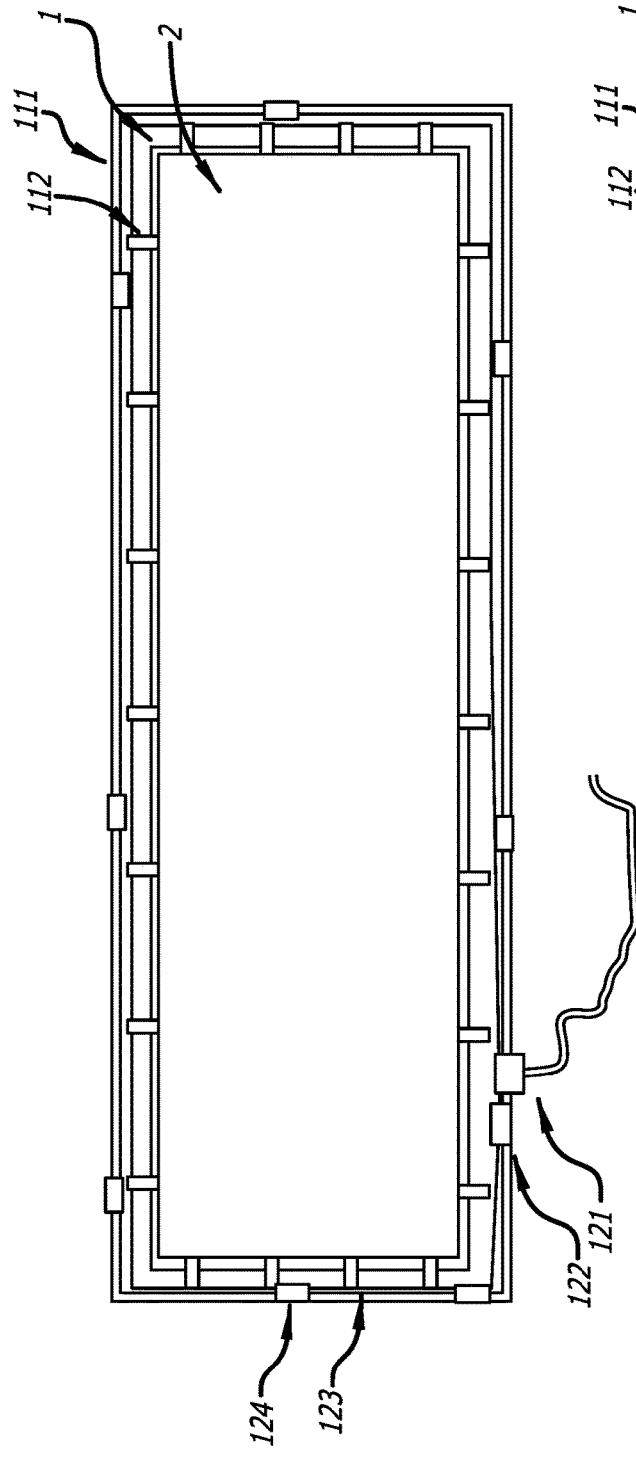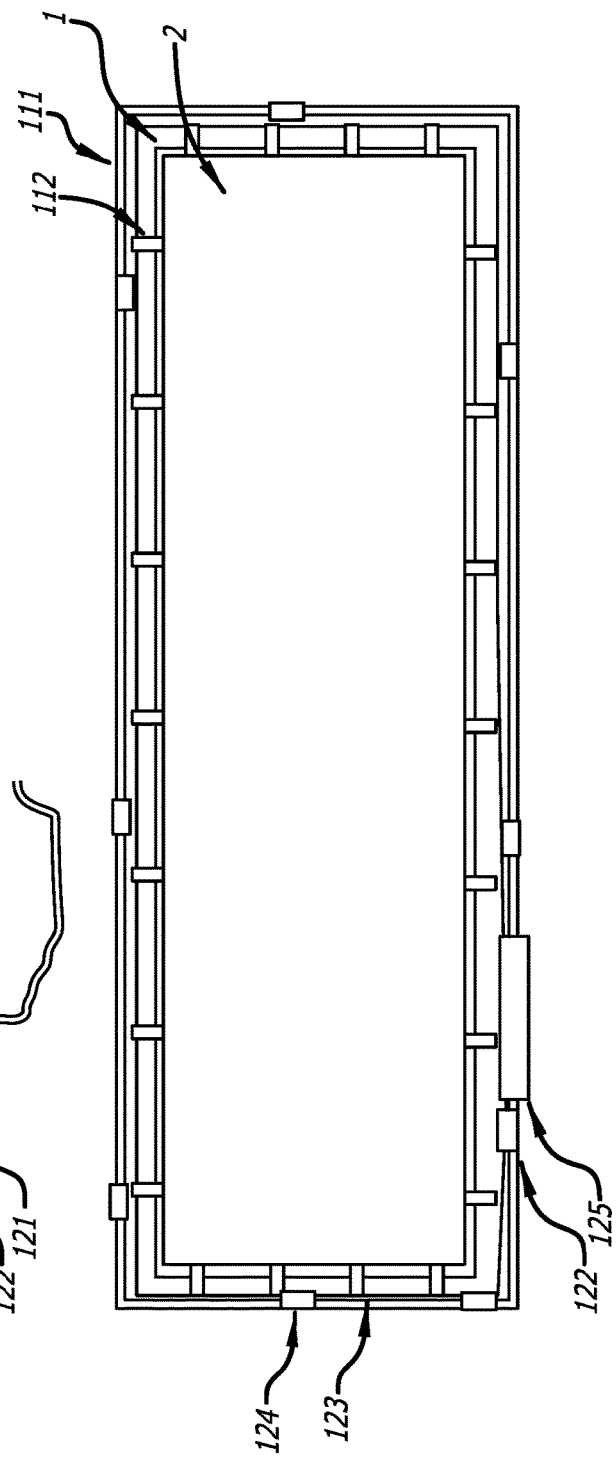

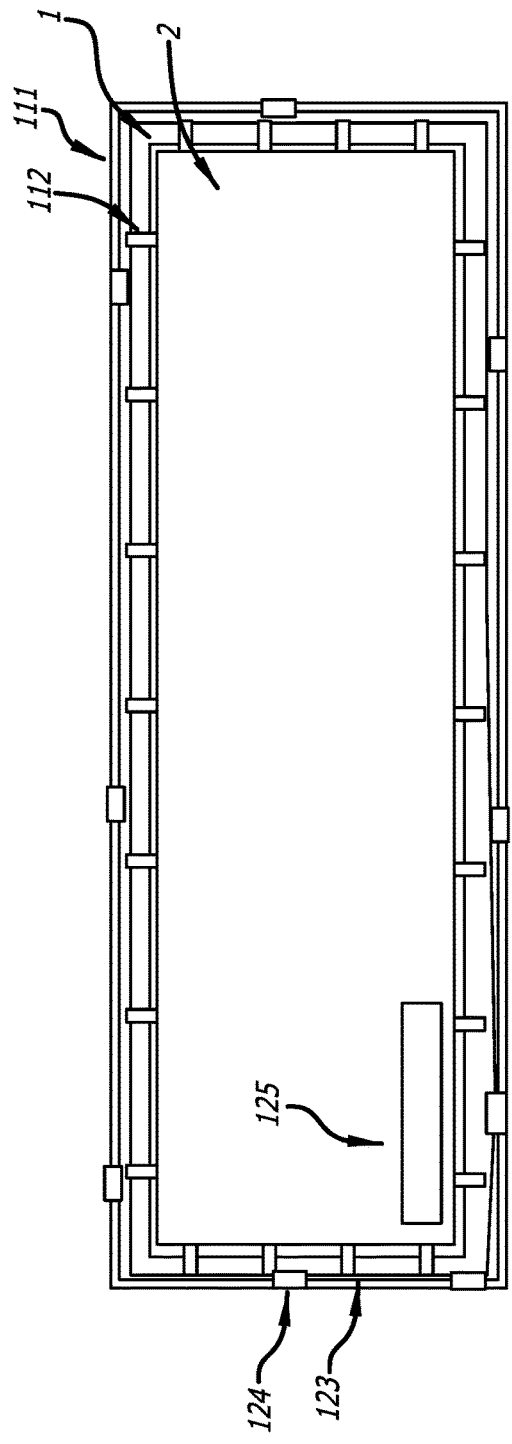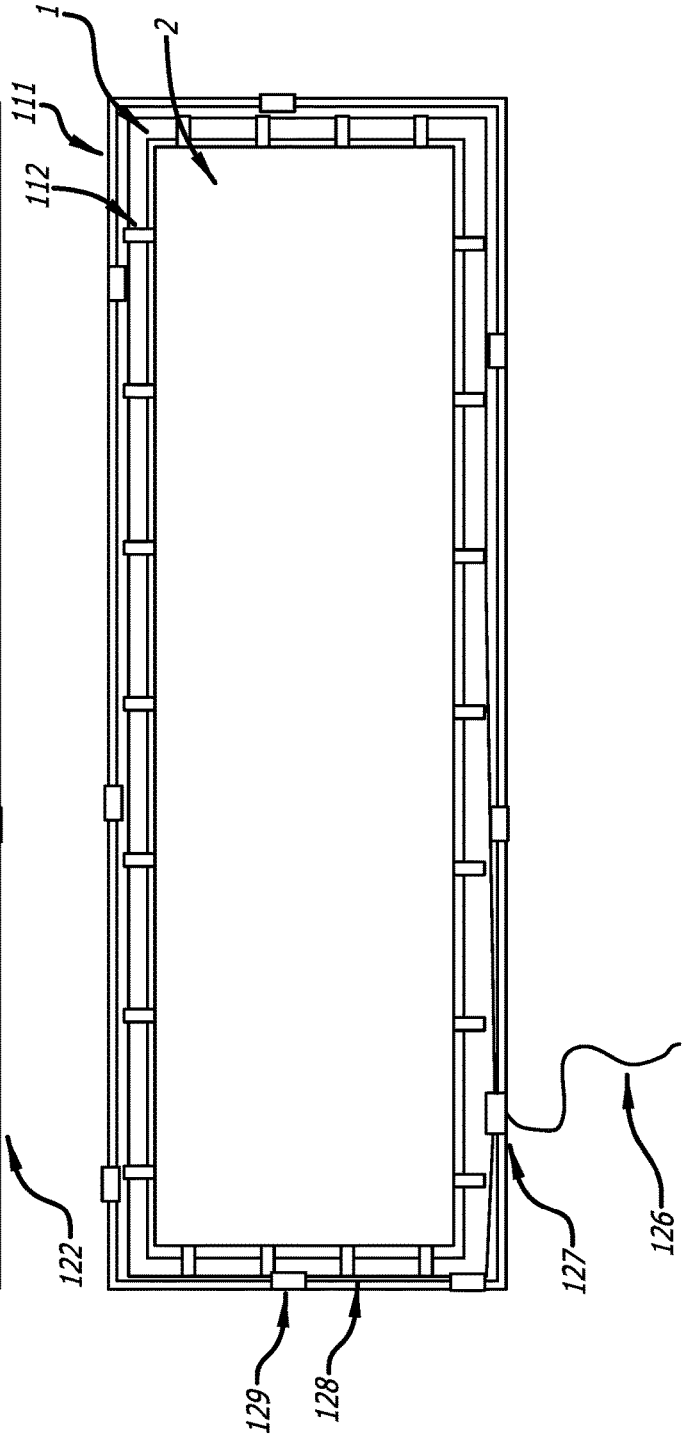

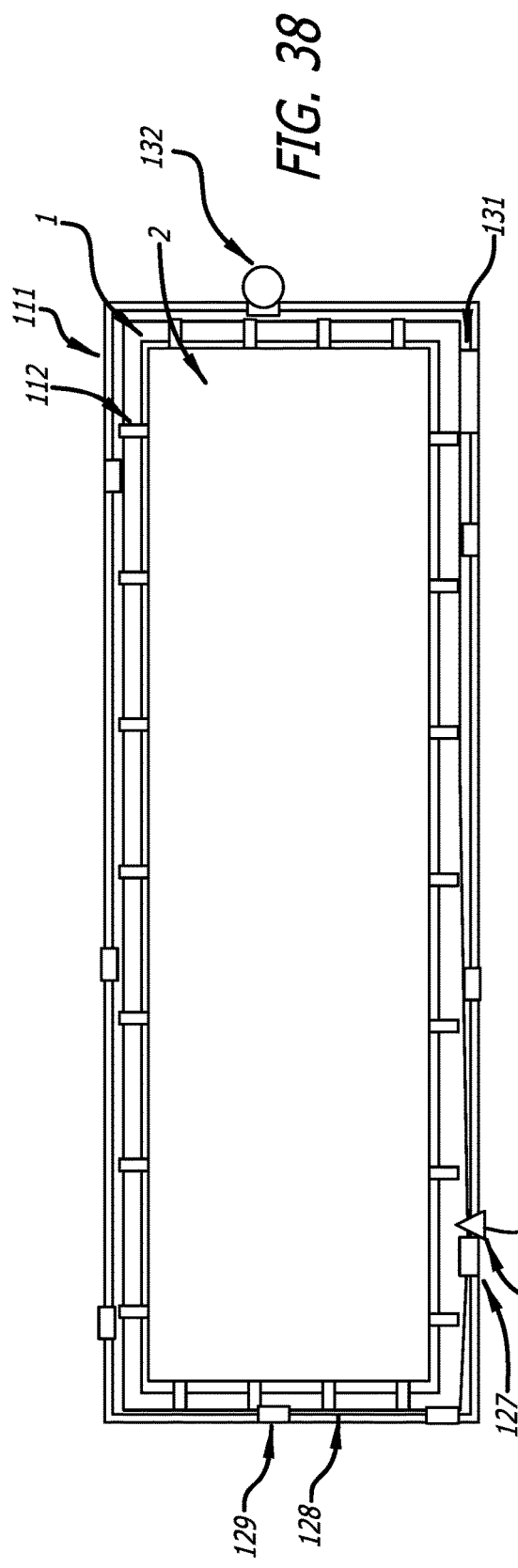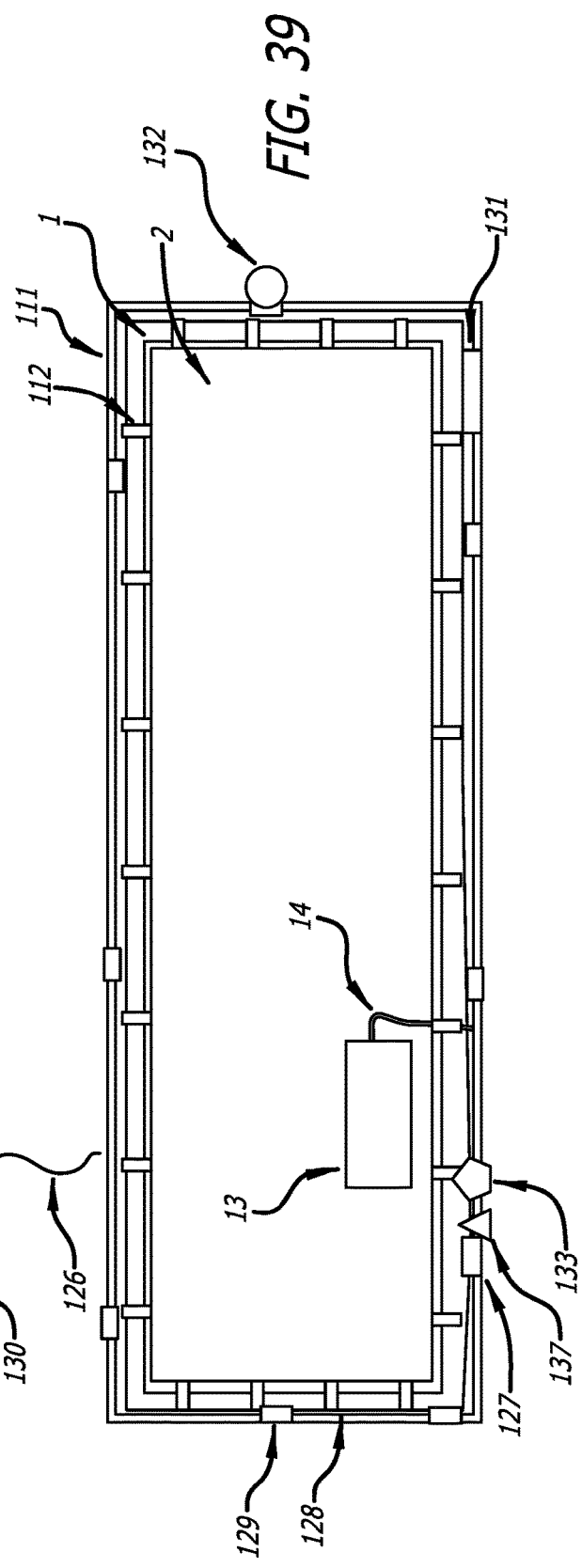

MULTIMODALITY MEDICAL PROCEDURE MATTRESS-BASED DEVICE

RELATED APPLICATIONS

This application is a continuation of and claims priority to U.S. patent application Ser. No. 14/961,822 filed Dec. 7, 2015 entitled Multimodality Medical Procedure Mattress-Based Device, which claims benefit and priority to U.S. Provisional Patent Application Ser. No. 62/088,495 filed Dec. 5, 2014 entitled A Multimodality Medical Procedure Mattress-Based Device, and to U.S. Provisional Application Ser. No. 62/240,409 filed Oct. 12, 2015 entitled Radioabsorbent Assemblies, all of which are hereby incorporated herein by reference in their entireties.

FIELD OF THE INVENTION

The present application relates generally to the use of devices during medical procedures (e.g. heart catheterization, surgery, medical imaging) in which a patient lies on a surface.

BACKGROUND OF THE INVENTION

Patient tables are used in a wide variety of settings for medical procedures and for patient transport. In most or all of these procedures, the patients lie upon a mattress that rests atop the patient table and typically consists of a soft pad that is contained within a flexible cover. While on the mattress, the patient is often connected to any one of a number of monitors that may be used to monitor pulse oximetry, blood pressure, electrocardiogram tracings, heart rate or other physiologic information. In addition, medical treatment devices, such as intravenous infusion pumps and cardiopulmonary resuscitation devices are connected to the patient on the mattress and attached to surrounding structures, such as a gurney or free standing pole.

The intention of the mattress design is to provide a durable, easily cleanable, relatively comfortable location for the patient to lie through the procedure with a shape that matches the table upon which it is to be used. This type of mattress is present on all patient tables throughout the hospital. While providing some modicum of patient comfort, this mattress is not designed with any additional features to provide value to the patient or clinician. In fact, patient mattresses are frequently surrounded by a variety of monitoring and therapeutic devices that are attached to the patient in one way or another. This results in a confusing array of cables, tubes, power sources, gas sources (such as oxygen), and displays. All of these require attachment to the patient or travel with the patient, creating a complex web of devices around and connected to the patient. These connections are prone to inadvertent mis-application and disconnection. Moreover, the need for a battery power supply in some devices increases weight and creates a need for recharging of multiple devices.

Many of the ancillary medical devices referred to above are attached to a table or gurney that supports the patient mattress. X-ray tables with rails that support patient mattresses have been developed (e.g. Philips Allura Centron table) and rail systems for stretchers have been described (applications Ser. Nos. 12/107,730, 11/784,994 [lapsed], Ser. No. 12/651,601). The rails attached to the table prevent patient movement without moving from the table rails all ancillary equipment attached to the patient. That impedes patient transfer to a bed and often leaves the patient unmonitored while electrodes are reattached.

Support structures within mattresses have been described, but these do not protrude from the mattress, are not intended to be attached to medical devices, and do not carry power or data conductors, or gas tubing (U.S. Pat. Nos. 8,984,690, 763,442, 4,676,687).

Mattresses with flexible covering to aid sliding and evacuation of patients from hazardous environments have also been described (PCT/IB2011/000190, PCT/IB2011/003057, U.S. Ser. No. 13/452,079, U.S. Ser. No. 12/968,840, U.S. Ser. No. 11/617,061), as well as ones with integral spinal protection boards within the mattress to stabilize the spinal cord during transport and straps to stabilize the patient within the evacuation apparatus. While helpful for evacuation of patients, these products do not support ancillary medical equipment such as pumps, monitoring devices, or radiation shielding.

Stith described a life support bed where the medical equipment needed for life support reside on the carriage of the bed (U.S. Pat. No. 4,584,989). This device obviously could not be easily transported or used for x-ray imaging.

In the medical procedure environment, the mattress and associated patient table are two of many pieces of equipment commonly used. Often times, there are monitors for electrocardiogram tracings, pulse oximetry, blood pressure and other purposes. For each of these monitors, there are associated cables or leads used to connect to the patient. These cables often become entangled and there is always a risk that leads are inappropriately managed or connected to the patient. Challenges with cable management can lead to procedural delays, entanglement with other devices, and potential patient misdiagnosis.

Medical procedures are performed often on patients lying horizontally on a mattress, such as an operating table. Ancillary equipment such as intravenous pumps, control consoles and imaging displays are often attached to a side rail on the operating table or bed frame. These rails are composed of metal and are configured to allow the attachment of a clamp or locking mechanism to fix the equipment to the rail. One problem with this method of attaching medical equipment to tables is that the table is usually fixed to a rigid structure such as an x-ray unit, stretcher, or large bed. Therefore, when patients are moved, the entire set of control devices and other medical devices attached to the patient must to detached and reattached to another bed structure or simply held by a caregiver or the patient. In addition, many of the devices attached to the rails require electrical power, connections to other devices, or pressurized gas. This creates a clutter of wires and tubes around the bed and also may impede efficient patient transfer from one area to another.

Another aspect of a patient mattress is the fact that the mattress must be thoroughly cleaned after each use. Concerns of viral or bacterial transmission from patient to patient necessitate an extensive cleaning process that includes manual spraying and wiping of all patient surfaces. Following that process, other potential disinfecting steps such as UV light or other sterilants may be used in an attempt to reduce the risk of contamination and disease transmission.

In the instance of a patient table used in an interventional catheterization laboratory, there are additional aspects to the use of the table and mattress. Arm boards are commonly used to support the arms of the patient, both with standard arm boards during a typical interventional procedure as well as with custom arm boards designed to manage the arm during a radial artery access procedure, in which the radial artery of the arm is accessed for catheterization. The current state of the art with these boards is simply to slide a polymeric sheet under the back of the patient to stabilize the board, which cantilevers over the edge of the mattress to support the arms. This can be a difficult maneuver to insert the board, and the rigid board directly beneath the back and shoulders of the patient may be uncomfortable.

The patient's wrist can be placed in any number of support devices that lay on the arm board. These support devices generally extend the wrist to provide better access to the radial artery. The disadvantage is that the support devices must themselves be secured to the arm board. In addition, procedures are usually performed with the physician on the patient's right side. Access to the patient's left arm for radial or brachial artery access to difficult. Typically, the entire operating team has to move to the patients left side and the room monitors (for example, x-ray and physiologic monitoring) must be moved to the opposite side. As a result, many surgeons have the patient drape their left arm across their abdomen in order to access the left arm arteries from the patient's right side. In this position, the surgeon's exposure to x-ray increases significantly. A number of devices have been developed to support the left arm in this position, but none have integrated x-ray shielding. i In addition to the discomfort to the patient, there is risk during radiographic procedures to the physician and cath lab staff due to radiation exposure. The fluoroscopy unit that provides imaging during the procedure emits x-rays that pass through the patient with the intent of reaching the image intensifier for the image to be transferred to the monitor. However, significant portions of the radiation intended for imaging are scattered by interaction with the patient and spread around the cath lab. Some of this x-ray radiation is ultimately absorbed by the physician and staff, increasing their overall radiation exposure.

Radiation protection during medical procedures requiring x-rays or other ionizing radiation is a major health concern for health care workers (HCW). There are numerous methods of shielding the HCW from radiation. Commonly used methods include the use of flat, inflexible, clear or opaque shields impregnated or covered with lead or lead equivalent materials. These are cumbersome to operate and require constant movement by the HCW to shield themselves from radiation. Frequently, they also do not conform to the patient's body habitus and contours. In addition, shields often get in the way of adequate fluoroscopic visualization of the patient or key areas of the patient that require easy access or monitoring. Another major impediment of existing methods is that the HCW has to move these heavy equipment manually and also conform their bodies to visualize around the impediments caused by the existing devices. This is a major cause for musculoskeletal morbidity of the HCW resulting in chronic neck, back injuries. Consequently, it is common for the HCW to sacrifice radiation protection for better visualization as well as better ergonomics by moving the current shields out of the way or positioning them in a markedly sub-optimal protection position. In addition, many times the HCW forgets to move the shields for adequate protection.

Systems of radiation shielding have been described. These systems, however, employ extensive heavy shields or encase the operator in a restrictive enclosure.

The device described herein offers continuous and critical radiation protection by partially or fully automating the radiation protection process as well as providing optimal patient and HCW ergonomics.

The primary problem with prior attempts to provide x-ray scatter radiation shielding is that the shield must conform to the patient's body contour and also be able to conform to the x-ray imaging device. Patients come in a wide variety of shapes. X-ray units are bulky and the physician often needs to image the patient at widely varied angles relative to the patient's long axis. For example, cardiac imaging requires the x-ray camera to be positioned in all four quadrants (over the left and right shoulder and over the left and right rib cage). The physician usually inserts a catheter into a blood vessel at a specific location such as the femoral artery, radial artery or jugular vein. The physician often needs to stand next to that body part during the procedure. As a result, an ideal shielding system would be able to conform to both the patient shape and the position of the x-ray camera.

A number of shields have been developed to absorb scatter x-ray. The most commonly employed is an apron, vest or skirt with integrated x-ray absorbing material that is worn by the user. X-ray absorbing gloves, glasses, and head caps have been worn to prevent x-ray exposure of specific body areas. These devices are cumbersome, heavy, and have been associated with orthopedic injuries. X-ray absorbing pads have also been developed (U.S. Pat. Nos. 6,674,087, 7,677,214). Problems keeping the pads clean from patient to patient have led to their use in a disposable form. This adds to medical cost and toxic waste. Finally, fixed, durable x-ray shielding has been used extensively. These devices primarily include leaded glass or acrylic in planar sheets hung from the ceiling, attached to the rails of an x-ray table, or placed into a free-standing structure (such as a wheeled structure or apparatus hung from the ceiling). Cocoons (in which the physician resides while operating) that absorb x-ray and large x-ray absorbing barriers have also been described (US20020109107, U.S. Pat. No. 7,091,508). These devices have shown to be too cumbersome to be of practical use. A number of other fixed or mobile x-ray shields have also been described. They provide partial x-ray protection for the physician and staff.

One challenge to x-ray visualization in the cath lab is ensuring that the area of treatment in the patient is not blocked by radiopaque materials that prevent adequate x-ray penetration for imaging. Typically, any radiopaque clip, instrument or wiring that is near the patient will appear on x-ray and potentially prevent visualization of critical anatomy. In particular, cables such as ECG leads that may drape across the patient can cause imaging difficulty. Many medical procedures require imaging of body parts and simultaneous monitoring of physiologic functions, such as an electrocardiogram, blood oximetry, respiratory rate, and blood pressure. Many conductors of electricity, such as copper and gold, are visible under x-ray and interfere with medical imaging. Even aluminum, which is less visible under medical x-ray, can be seen when the wire diameter is sufficiently large or when multiple wires are stacked together, such as when conductors are circled by a shielding material. These problems interfere with the monitoring of patients undergoing x-ray examinations.

While there are concerns that clips and wiring may interfere with visualization of patient anatomy, there is a need for connections to the patient in a manner that provide critical diagnostic information. Pulse oximetry, electrocardiographic traces and blood pressure readings are all examples of data that may be vitally important during a medical procedure. Currently, the methods used to gather this information are not streamlined or synchronized in a manner that is conducive to simple and easy use in the interventional cath lab or other medical settings. Solesbee (U.S. Pat. No. 6,721,977) described the use of wires in a patient mattress to allow integration of patient monitoring cables. Wilson and Kim (U.S. Pat. No. 8,491,473) describe a conduit system within a patient mattress, where the conduit carries wires for monitoring and patient treatment. These are useful additions to the patient mattress, but the conductors and conduits are visible on x-ray imaging when the x-ray camera is turned in some directions (such as when the x-ray tube is under the patient's right shoulder aimed at an x-ray detector that is over the patient's left lateral chest). Wiring that is conductive but nearly invisible under x-ray would improve the inventions of Solesbee et al (U.S. Pat. No. 6,721,977) and Wilson et al (U.S. Pat. No. 8,491,473).

Others have described mattresses of composite construction, including possible components such as flexible inner members with a range of stiffness and an outer containment jacket or cover. However, no present invention envisions a mattress of composite construction that utilizes the materials of the construction to provide for a rigid frame, patient comfort and a suite of features that may provide solutions to previously unresolved issues related to imaging, radiation exposure, cleaning and modular attachment of arm boards or other devices and monitors.

OBJECTS AND SUMMARY OF THE INVENTION

Aspects of the invention described herein generally include:
1. A mattress on which a patient lies, where the mattress is contained within an outer, more rigid shell
2. Rails attached to the mattress or mattress shell are used to attach medical devices and shielding, where the rails may contain a power supply, medical gasses, and conductors for data and computer communication
3. A flexible x-ray shielding system that conforms partially to the patient and x-ray system independently
4. A wiring system composed of flat conductors that are minimally visible on x-ray
5. A blood pressure cuff that can be applied around the arm or leg like a clamshell
6. One or more work surfaces that attach to the mattress rail and provide attachments for clips and other devices to stabilize catheters in the sterile field, an inductive power supply to the sterile field, and radiation shielding
7. One or more heating elements in the mattress with one or more surface temperature feedback sensors that can be used to warm patients in selective body locations or to sterilize the mattress with heat
8. An attachment for cardiopulmonary resuscitation that attaches to the mattress rails and derives power or data control from the rails or mattress.
9. An intravenous infusion pump that receives power from the mattress rails or data control from the mattress or mattress rails.
10. A capacitive ECG sensor that is imbedded into the mattress cover or located below the cover and associated electronic signal processing to provide an ECG signal from the patient lying on the mattress.
11. A device to hold the patient's head that provides radiation shielding, stabilization of head position, and a wrap around the neck that allows for rapid circumferential cooling of the neck to provide brain hypothermia.

This invention describes a medical procedure mat designed to provide integrated patient monitoring and comfort by having a mattress and perimeter shell. The shell is composed of a material more rigid than the foam mattress supporting the patient, such as closed cell foam, fiber glass, carbon fiber, or other rigid material that has minimal x-ray absorption, and an inner insert with open cell or more elastic material to provide comfort. The surface upon which the patient will reside is covered with either flexible closed-cell foam or another appropriate textile that is durable and easily cleaned after use. Medical monitoring and connections to the monitoring devices may reside in between the rigid and flexible layers.

The invention is an object on which a human can lay or sit, where the object contains sensors to monitor physiologic functions. In addition, the object may contain therapeutic devices to provide treatment. In addition, the device has a variety of compartments to house medical equipment and a perimeter rail attached directly to the mattress to provide additional monitoring and therapeutic devices, and a system for distributing electrical power, medical gasses, computer data transmission, and radio receivers and transmitters.

In one embodiment, the object is composed of carbon fiber. The carbon fiber supplies sufficient rigidity to support the remainder of the object, including the included devices and the patient. The carbon fiber structure has cavities or drawers for storage of devices and wiring (including electrical and optical cables, with optional electromagnetic shielding). In addition, the closed carbon fiber may also have rigid members within or covering the foam to provide additional structural integrity.

In one embodiment, the main cavity of the closed cell foam 1 is filled with a softer foam 2 for patient comfort. In one embodiment, one or more top layers of foam are provided to further enhance comfort or to provide specialized functions, such as electrical conductivity, magnetic properties, radiation blocking agents, antibacterial, antifungal or antiviral properties, or photon transmission.

In one series of embodiments, the procedure mat is designed to integrate with commonly used procedure tables that have been installed in the hospital or clinic. In this way, the mat replaces the simple mattress that sits upon the table with a device that provides for patient comfort as well as patient monitoring and cable management.

In one such embodiment, the procedure mat is a relatively rectangular shell structure constructed of relatively rigid closed-cell foam with an open top surface. In another embodiment, the shell is composed of carbon fiber. In yet another embodiment, the shell is composed of aluminum. This shell contains a cavity to house an inner mattress component while acting to provide structural rigidity to the composite device, allowing for routing of cables or wiring throughout the mat and locations to which other structural members such as rails or monitors may be mounted. The inner mattress component is a compliant material which provides for patient comfort. The upper surface of the mat will be covered by a flexible, non-permeable material that will provide for patient comfort as well as furnish a non-porous surface that is impermeable to fluids, resists staining and is easily cleanable.

This profile of this structure may also be adapted to better match patient anatomy and provide closer access to the patient from the caregiver or for diagnostic, therapeutic or imaging equipment. In these configurations, the head region of the mat is narrowed, with the mat increasing in width at the shoulder level and possibly again at the hip level on a supine patient. This type of mat configuration and others may be dimensionally specified to match geometries with procedure tables produced for interventional cardiology, radiology, surgery or other use. In another embodiment, the flexible portion of the mat has protrusion or indentations that facilitate the positioning of the patient on the mat, such as a protrusion at the superior shoulder level to guide optimal positioning of the patient in the long axis of the mat. Similarly, indentations or protrusions for the trunk head, or legs help position these body areas in the left-right axis of the mat.

In yet another embodiment of the procedure mat, the mat contains other features to improve functionality for specific uses. In the region within the mat on which the patient's torso rests, the mat may contain a more rigid support structure that supports the chest of the patient The purpose of this more rigid structure to improve the effectiveness of chest compressions if they are required for cardiac resuscitation.

Another feature of the outer more rigid structure of foam or carbon fiber is the ability to create outer ridges that prevent patients from falling off of the mattress. In one embodiment, the outer ridge can by folded to the outer side of the mattress to allow easier transfer of the patient of the mattress. Moreover, the hinged segment, once folded over, provides an extended surface for transfer.

The anchoring of components to the mat is deemed beneficial in particular when considering the range of procedures that may be performed on a patient residing upon the mat. In the case of interventional cardiology, arm boards are often desired to provide a location upon which the patient may rest their arms. Current technology uses a rigid polymeric sheet that is anchored by placing it under the torso of the patient, an unwieldy and uncomfortable environment. The anchoring component of the mat allows for arm boards 4 made of foam or other material to be designed to be integrated with the anchoring component so that they may be attached or detached as desired. This provides simple, modular and comfortable use of arm boards when necessary for a procedure.

The resuscitation aspect of the embedded reinforcing structure provides a significant benefit when compared to the current state of the art. At the present time, if a patient suffers from cardiac arrest and requires resuscitation, the physician will initiate chest compressions while the patient is lying on a standard mattress. The typical mattress has significant compressibility, meaning that for each chest compression applied by the physician, a substantial amount of the energy goes into compressing the mattress rather than compressing the rib cage and ultimately the heart. The result is less-effective compressions, causing a significantly higher level of fatigue to the physician and reduced cardiac output. By adding a rigid component in place of a portion of the mattress under the chest of the patient, the compressibility of the mat is reduced. Therefore, the result is more effective chest compressions which result in lower physician fatigue and better clinical results.

In addition to the modular arm boards that may be added to the edges of the mat, additional components may be added to the mat itself or modularly added to arm boards that are attached to the mat. In one particular embodiment, flexible radiation shields may be reversibly affixed to the arm boards on a mat used in interventional cardiology or radiology procedures in such a way that they may extend vertically, horizontally or in a curved manner around the patient. These radiation shields are designed such that they prevent x-ray radiation that reflects or backscatters from the patient from reaching the physician or catheter lab staff. Other modular radiation shields may be placed at or near the waist of the patient and/or near the neck of the patient to prevent backscatter radiation from exiting the imaging field. Each of these shields are designed such that they will flex out of the way when contacted by the image intensifier of the c-arm or x-ray imaging unit as it rotates around the patient.

These modular shields may be designed such that they act independently of one another so that movement or use of one component does not affect the other components. Alternatively, they may be designed to mate with one another such that they are attached to one another during use with clips, snaps or magnets, or their geometric design may be such that the components nest within one another in their static position. In one embodiment, the edges of the components are magnetically attracted to one another so that they provide continuous radiation protection around the patient through direct contact between the components, but when the image intensifier pushes on the component the magnetic attraction between components is broken and the impacted radiation shield is free to bend and flex out of the way.

In another embodiment, the winged radiation shield attached to the mattress can bend on a hinge, for example a hinge with a spring that biases the hinge to a position such that the radiation shield is in an upright position. When an x-ray camera needs to be positioned such that the radiation shield would prevent the user from obtaining the desired radiographic projection, the shield can be reversibly moved aside by the movement of the camera by the shield pivoting on the hinge. If a view is desired that is more lateral than can be provided by the wing with the spring-loaded hinge, a release mechanism can be actuated that deactivates the spring and allows the hinge to rotate completely downward, moving the wing out of the field of view.

In yet another embodiment, the neck and waist components of the radiation shield are specifically adapted to ensure that vascular access can be gained for an interventional procedure. There are notches or cutouts provided in the shield so that the femoral artery and femoral vein may be reached in the leg, and the carotid artery and jugular vein may be reached in the neck. Additionally, the radiopacity of the shield components may be reduced in key regions so that areas that may require visualization such as the distal aorta and the iliac arteries can be seen through the shield.

In yet another embodiment, the waist component of the device consists of a "Flag" with elements to conform to patients' body habitus and other elements to flexibly and reversibly deform to accommodate other equipment in the environment of the operating room.

The flag consists of an element that attaches the Flag to the patient's mattress, the table the patient lies on, a free standing device or to a wall or ceiling mount. The attachment mechanism has one or more rigid arms connected at an angle, such that an arm(s) are horizontal and extend from the Attachment mechanism. Below one of the arms is a radiation absorbing material configured in such a way as to conform to the patient's body. Above the same or another arm is a radio-absorbing material that can be reversibly displaced. For example, an x-ray camera can be positioned such that it pushes the upper part of the shield away to allow the camera to be positioned for a particular x-ray view.

The upper functional unit has a degree of internal flexibility/elasticity and has a horizontal articulation with a lower functional unit and a vertical articulation with a lateral functional unit. This allows the upper unit to freely move on a horizontal axis as well as have some elastic stretch when the equipment in the room such as an image intensifier pushes it to enable optimal imaging conditions. This allows the lower functional unit to remain in place on the patient continuing to block radiation scatter from the patient's body while the upper unit bends away and conforms to the image intensifier. In addition, the Flag can have vertical supports throughout. The supports contain a hinge or spring apparatus to allow the Flag to bend in the vertical plane. This allows the Flag to conform to other radiation absorbing material, allowing the Flag continues to form a shell around the patient to continue blocking the radiation scatter. Because the Flag has elastic properties, when the image intensifier moves away from an interfering position, the Flag returns to its initial position, preventing gaps in the shielding where radiation may be emitted towards the HCW.

In one embodiment, the Flag has asymmetric curves that contour to a patient body habitus in the lower functional unit to maximize radiation protection to the HCW.

This novel invention contrasts with current devices, which are pushed out of the way by the image intensifier or the HCW to prevent getting in the way of the HCW being able to work with catheters etc.

The invention allows the lower portion of the flag to stay in place without moving away and also adds the ability of the upper functional unit to continue to offer radiation protection. This combination minimizes or eliminates the interference to the HCW work flow and allows them to continue their procedure uninterrupted.

The third functional unit in the current embodiment includes a contoured lateral unit which has a vertical articulation with the upper and lower units of the flag. The lateral unit curves towards the patient to block the radiation that currently reaches the HCW due to the wide gap between the floating ceiling-mounted shield and a lateral shield sometimes used by HCWs. The vertical articulation also allows for the flag to conform with the lateral wing described previously. In addition, there are also cut out areas along the lower border of the lateral and lower functional units to contour to the patients forearm and the groin area to allow for maximal visualization.

The radioabsorbent barriers on the top or bottom of the Flag can be composed of multiple overlapping material, such that an object displacing one piece of material would not displace the adjacent section. This would improve radiation protection.

The flag units can be constructed of radioabsorbent fully or partially transparent material or could have a radioabsorbent clear window in portions to allow for optimal patient visualization. The Flag also can hold a patient instruction and or entertainment window where a screen could be placed.

In another embodiment, the flexible portion of upper part of the radiation shield is composed of multiple rigid elements that are attached to the shield with at a hinge. The elements absorb x-ray and can flex at the hinge point passively as the x-ray detector pushes them. The hinge can be a simple spring hinge that rotates in one plane or a ball hinge that rotates in two planes. It is recognized that many types of hinges could provide a rotating mechanism. An advantage of multiple hinged shields is that only a portion of the shield will be displaced, improving radiation protection of the operator and also reducing the force needed to move the portion of the shield that obstructs the x-ray detector. An additional benefit is the transparent shielding material, which is inherently inflexible, can be incorporated into the shield. This has the advantage of allowing the physician to see the patient through the flexible shield.

In another embodiment, the multiple rigid elements are composed of a mixture of flexible and in flexible material. For example, leaded glass can be combined with a flexible polymer material, such that a portion of the individual element is flexible and a portion is rigid.

In another embodiment, the multiple element shield can be attached to the workbench, such that the element rotate from the workbench, which serves as a supporting member.

The Flag is anchored to the mattress or patient table, to another free standing mechanism or to a wall or ceiling with features that allow for rapid stowage. The Flag has freedom to rotate on 3-axes and also has spring loading mechanisms built in such that it assists the HCW in moving the flag with minimal use of force and allows for the flag to return back to a neutral position or to another position between neutral and extreme flexion or extension to contours to the patient and the equipment in the room as closely as possible.

Invasive angiography and other medical procedures and operations are often performed on patient lying on support structures known as operating tables. In some patients, the upper extremities are instrumented, particularly the radial artery in the wrist. The arm usually rests on an arm board that is attached to the operating table. The arm is often abducted to allow better access to the wrist or antecubital fossa. The arm board holding the abducted arm often pivots away from the operating table to support the abducted arm.

In procedures where catheters or other medical instruments extend from the arm in a caudal direction there is no supporting surface on which the catheter or instruments can lie. As a result, the physician either holds the catheter manually or drapes it over the operating table by curving the catheter or instrument. This leads to catheters or instruments falling off the table or diminishes the physician's ability to manipulate the catheter or device. The problem is particularly present in patients undergoing radial artery catheterization, where multiple catheters and guidewires can extend out of the radial artery for over a meter in length.

There are support surfaces that attach to operating tables or are positioned partially between the mattress and the operating table. Although helpful, the attachment point is below of the surface of the mattress and the tables must be removed during patient transport. In addition, these tables are simple surfaces, some with x-ray absorbing capacity but no ancillary capabilities to manage the catheters and wires emanating from the patient or attachment of devices to supply inductive power to the sterile field.

The invention described here is a generally rectangular table that can be attached to the procedure mattress, usually by attaching to a rail on the mattress. One feature of this board is the ability to attach clips to hold catheters or wire. Another feature is the presence of an induction coil to transfer power to devices in the sterile field. Yet another feature is a quick release mechanism. Another feature is a mechanism to fold or rotate the table against the operating table to allow for the transport of patients on and off of the operating table and mattress.

In another embodiment, the outer ridge of the outer shell is hinged such that it can be folded over to the outside of the mattress, creating a flat structure that extends from the mattress outward. This flat surface can then serve as a table for the physician to use during the procedure.

The ability to clip or hold catheters and guidewires in place would improve procedure safety, free the surgeon's hands for other tasks, and facilitate faster catheter exchanges over the guidewires. The problem with clips is that the operating table is typically covered with a sterile drape. The drape is loose fitting and moves. To solve this problem, two methods are described for attachment of devices to hold wires or catheters. In one embodiment, magnets (such as NdFeB) are placed at or within the surface, at certain spots on the board. Wire or catheter holders on the top of the sterile drape mate with the magnets. The holders have either oppositely polarized magnets or a magnetically attractive material (such as steel or iron). This allows them to hold position through the drape material. In addition, the use of two oppositely polarized magnets on one side prevents movement further. In another embodiment, the clip holder has the magnet and the board has areas of magnetically attractive material, (either discrete areas, tracks, or the entire board). Alternatively, the wire holder could be a simple magnet or magnetic material that is designed to mate with the magnets embedded within the surface of the patient mattress. The intravascular device such as a wire or catheter is placed on the drape atop the magnet, and a magnet or magnetic material covered in a soft polymer such as silicone is placed on top of the wire or catheter. The magnetic attraction between the two components will apply pressure on the wire or catheter, and the combination of the pressure and the coefficient of friction of the polymeric material will prevent movement of the interventional device. The soft polymeric material will also prevent damage to the sometimes fragile interventional device.

Another embodiment of a connector from the sterile field to the table is a clip. The clip is typically attached to the table. The opening is wide enough to allow the drape to lie within the clip. A wire or catheter holder then sits on top of the drape. It has a configuration that mates with the underlying holder, reversibly locking the upper holder to attach to the table.

In another embodiment, an adhesive pad attached to the underside of the drape or the surface of the table holds the drape to the table. The wire or catheter holder is attached adhesively to the attached drape.

Another embodiment of a clip mechanism that provides for simple attachment and release may be constructed of a highly compliant material such as silicone rubber or foam with a magnetic component in the base to affix to the table surface as described above. This compliant component has a notch or space in which the interventional device to be held will reside. Manual compression of the edges of the device compress the notch and grip the device. The deformation of the device by the act of compression causes clips mounted on either one or both sides of the non-compressed axis to extend beyond one end of the device and lock the device in the closed configuration. The ends of the clips on the non-attached side of the device extend beyond the compressible component of the device. Compression of these clip ends lever the locking end of the clips and release the compression. In this way, the locking can be effected using two fingers in compression on the complaint material and unlocking can be effected by using two fingers to compress the clip ends. The combination of the use of a simple attachment and release mechanism and highly compliant materials provide for a highly effective and easy to use component that is protective of the potentially fragile devices used in interventional procedures.

It is recognized that a combination of the attachment mechanisms could be used together.

Delivering electrical power to devices in a sterile field has always been difficult. Typically, the power is provided by sterile batteries or by a wire that is wrapped in a sterile drape. In this aspect of the invention, an induction coil is located within the operating table or side table. The induction coil sits in the non-sterile part of the field and is attached at one end to a power source and at the other end to the coil. Typically, the coil is mounted on the table in plane and at or near the surface of the table. A sterile receiving coil is placed over the coil, above the sterile drape. There is a mechanism for fixing the position of the receiving coil relative to underlying coil. These mechanisms include: adhesion of the receiving coil to the drape and drape adhesion to the table, magnetic connectors as described above, and clip connectors as described above.

In another embodiment, the inductive power source is used to control a medical device through changes in the power delivered. For example, the power to a motor used to drive an ultrasound probe to spin within a catheter can be adjusted to control the rate of spin and the position of the ultra sound generating element within the log axis of the catheter in the patient.

A table described above must be able to be moved out of the way in order for a patient to get onto the operating table. The table described herein can be attached through a quick-connect. In addition, it is anticipated that one could fold the table against the operating room table side.

Another type of work surface that may be used in conjunction with the mattress is a workbench that resides over the patient on the table, particularly over the lower legs of the patient. This device provides radiation protection, improves workflow, provides equipment storage, can easily be draped with a sterile bag, provides access for vascular catheter access, and can easily and quickly be removed from the operating field. In addition, one embodiment facilitates application of pressure to the body to reduce bleeding.

This device component consists of a horizontal tray that curves downward on the end facing the operator. The tray is positioned across the patient's body. The tray is composed of a radio-opaque material that blocks x-radiation. The radio-opaque material absorbs x-ray photons emitting from the patient while the patient is undergoing an x-ray imaging procedure. The curve of the tray blocks radiation emitting from the side or legs of the patient. The operator radiation exposure is therefore reduced.

The tray is connected to an attachment apparatus to then connect the device to a supporting structure (such as a bed or x-ray table). The attachment apparatus is fastened to the mattress or table that the patient lies on or a side-rail. A mechanism in the attachment apparatus allows the tray to rotate around the axis of the attachment apparatus, to flip up toward the attachment apparatus, and to tilt with one edge of the tray closer or farther away from the patient. The attachment mechanism itself can travel in a vertical up and down motion to move the tray above the patient and to lower the tray to the patient's body. This allows the tray to be positioned across and just above the patient easily, which allows the device to accommodate patients of different body shapes. It also allows for the tray to be removed up and out of the way quickly in case of emergency.

In another embodiment, the tray is a laminar construct with one or more layers of radio-opaque material and one or more layers of material with minimal x-ray absorption. In another embodiment the tray is composed a clear x-ray absorbing material such as a clear plastic polymer with a high content of an x-ray absorbing material (such as boron, beryllium, barium). In another embodiment, the tray has attachments that do not absorb x-rays, such as a piece that connects to the attachment apparatus and the tray. In another embodiment, the tray has a forward edge that curves upward to more comfortably rest against the patients belly to further block radiation from the body.

In another embodiment, the tray is attached to a free standing device.

In another embodiment, the dimensions of the tray are adjustable to fit different patient sizes. Since the tray is connected to an attachment device, the distance between the attachment device and an anatomical landmark (such as the femoral artery) needs to be adjustable so that the functional aspects (such as the cutouts for access to the femoral artery) can be located over the appropriate body location. Additionally, the tray functional aspects might need to be placed over two or more body areas. The tray can also have multiple sliding or rotating adjustable surfaces o fit the body dimensions of the patient. On mechanism is one or more sliding elements. Another mechanism in a rotation of two elements on a swivel hinge.

The tray has cut outs to facilitate access to parts of the body, such as the femoral artery and vein, while minimizing x-ray transmission. In addition, radio-opaque flaps or barriers attached to the access sites can be opened and closed to allow access when the x-ray is off. In addition, ridges near the access site block x-ray photons that are directed at the operator's position.

The tray has attachment devices to hold sterile surgical instruments, imaging devices, or supplies. These attachments allow the operator to have free hands for other tasks, such a puncturing an artery while the attachment holds an ultrasound probe to visualize the artery through the skin. In one embodiment, the attachments are connected to the tray underneath the sterile barrier or surgical drape and in another embodiment, the instruments are attached over a sterile barrier or surgical drape.

The tray also has indentations that provide storage areas for surgical devices and supplies, such as needles, guidewire attachments, gauze, suture, and sterile fluids. In addition, the tray has spring clips and other attachment devices to hold catheters and wires emanating from the body. This stabilizes the positions of the catheters or wires and frees up the operators hands.

A light may be attached to the tray illuminates the surgical area. The light may be controlled by a switch on the tray or by a remote device (such as a wireless device). The light can provide general lighting to the procedure area or a focused light on a particular area of interest. The lights are often dimmed in the x-ray imaging rooms and white light can interfere with the operators viewing of procedure monitors. In one embodiment, lights of different colors are used to provide lighting that optimizes the viewing of x-ray and vital sign monitors.

In another embodiment, advantage is taken of the position of the tray over the body. During some types of surgical procedures, pressure needs to be applied to the body, for example, to stop bleeding or compress a hematoma. This can be challenging when the bleeding occurs next to the surgical site. The operator needs to be manipulating catheters or surgical devices and cannot press on the body at the same time. An assistant's hands in the field obstruct the operator's hands. A balloon or active device under the tray can be inflated or activated to produce pressure on the body. When a balloon is employed, the balloon can be inflated by an electric pump, a manual pump operated by an assistant outside the sterile field, a manual pump pumped through the drape by the operator. Alternatively, a simple broad foot can be extended mechanically (such as a ratchet mechanism) down from the lower surface or side of the tray and mechanically locked into place.

Other balloon compression or mechanical compression devices exist. A balloon device is employed in a band that surrounds the patient. Mechanical C-clamps are used with one portion of the C-clamp under the patient and a compression foot is over the body. These devices are difficult to employ during a sterile procedure and require contact with the posterior and anterior aspects of the patient.

A key feature of this device is that it is used during sterile procedures. The asymmetrical connection to the attachment device permits easy draping with a sterile pouch or cover that covers both the upper side of the tray (where the gloved operator touches) and the lower side of the tray that meets the patient's sterilely prepped skin or the sterile drape covering the patient. In an alternative embodiment, the entire tray is delivered sterile and attached to the attachment mechanism by a gloved operator. In yet another embodiment, the attachment mechanism and the tray are sterile and are attached to the mattress, rail, table or freestanding device by a globed operator.

Another embodiment includes a dedicated mount that attaches to the bed or tray, to which an IV pole or other device (infusion pump, etc) could be mounted. The device has flexibility of position so that it can be pivoted to multiple positions or otherwise moved out of the way if necessary.

Devices are described that are usable to attach a catheter, wire, or other medical device to an operating table. The device has an attachment mechanism whereby the holder can be affixed to a drape or operating table (with or without a sterile drape), as described above. The holder is type of clip device, where the inner surface of the clip is covered with an elastomeric material or a material treated to facilitate attachment to a medical device by a friction fit. On example of an elastomer is a foam material. Another is silicone. Another is a gel material. An example of a friction enhancing material is silicone, certain rubbers, and materials where the surface is treated. Surface treatments include grit, ribs and grooves.

Measurement of blood pressure in a clinical environment typically is done using a cuff that surrounds the arm and a pressure gauge. The cuff contains an air bladder that can be reversibly pressurized using a pump. The air bladder is connected to a pressure gauge. The cuff containing the air bladder is typically a strip a long rectangular shape that can be wrapped around a arm or leg and fastened with a variety of fasteners (such as Velcro, hooks, or buckles) to approximate the air bladder to the size of the arm. The air bladder is typically pressurized to a level that arterial blood flow to the arm is obstructed by the pressure of the bladder encircling the arm. As the pressure is let out of the bladder, blood will flow into the arm intermittently when the encircling pressure falls below the systolic blood pressure. Flow will become continuous when the pressure falls below the diastolic blood pressure. The occurrence of intermittent and continuous flow can be determined using several methods, most often by listening for Karotkoff sounds using a stethoscope or using the oscillometric method.

One problem with the measurement of blood pressure using a cuff is that the cuff must be placed circumferentially around the arm. This requires the person applying the cuff to use two hands to apply the cuff to the arm. In addition, creating a cuff that automatically attaches to the arm has been difficult.

Provided is a clamshell-like device containing an air bladder that reversibly attaches to the arm or leg. The advantage of the device is that a blood pressure cuff can be attached easily using one hand, without the need to circumferentially wrap the bladder around the arm or leg. In addition, the clamshell device can be attached to a surface and provide an automatic attachment by the motion of the arm into the open clamshell. The force of the arm into the clamshell activates the closure of the clamshell by mechanical means or by triggering a switch that secondarily cause closure (such as using a motorized closure).

Factors that affect pressure measurement by the oscillometric method are the housing around the air bladder, the completeness of the encircling air bladder, and the elasticity of the encircling air bladder. In testing, it was found that a rigid outer constraining device causes more discomfort and changes the oscillatory changes in pressure relative to the blood pressure. In one embodiment of this invention, the outer housing of the air bladder is a rigid hemi-cylinder and interposed between the rigid outer housing and the air bladder is an elastic material that is compressed as the air bladder is pressurized. This allows the airbladder to pulsate as the pressure is reduced to less than systolic, but higher than diastolic pressure during blood pressure measurement. The material could be a foam or could simply be an air void where the bladder is attached to the rigid structure along its edges.

The two edges of the encircling housing may be attached securely in order to apply circumferential pressure to the limb. One method of fixing the clamshell into a closed position around the arm is to employ a spring mechanism, biasing the clamshell in the closed position. It was found that this type of configuration had two drawbacks. First, the spring constant required for effective closure was very high and posed problems for a user to open the clamshell with one hand. Second, the spring altered the oscillation of air bladder pressure relative to the actual blood pressure, making measurement of blood pressure less accurate. Closure of the clamshell at the parting line was much more effective. This can be accomplished using a number of methods, such as a magnetic attachment, a hook or clasp, a releasable ratchet mechanism, or a pin and receptacle releasable lock. In one embodiment, the attachment and release is performed with one hand.

The housing for the air bladder may be composed of a rigid shell, such as a metal or polymer. This provides the easiest manipulation of the device. Alternatively, the outer housing can be made from a flexible material (such as cloth, polymer, or foam) with a support skeleton compose of a more rigid material, such as steel, nitinol, or rigid polymer. In another embodiment, a rigid foam material can be used without the need for internal support. The advantage of this embodiment is that the inflation of the bladder causes less discomfort.

In one embodiment, the clamshell device is attached to a medical procedure mattress, arm board, chair or other surface. In one aspect of the embodiment, the air tubing to connect the air bladder with the pressure gauge is integral to the surface on which the cuff is mounted, that is, the tubing is attached to the mattress arm board or chair, or in a channel within the supporting devices.

In another embodiment, tubes emanating from the airbladder attach to the supporting structure by means of a valved or non-valved plug-in connection.

In another embodiment, the parting line is not closed for the measurement of blood pressure (FIG. 4d). The clamshell is bias-closed by a spring type mechanism (including a spring or compressible air reservoir). A sensor measures the angle at the hinge point of the clamshell, which can be converted to a cross-sectional area described by the inner diameter of the clamshell. The pulsation of blood in the limb will cause the angle to fluctuate. In another embodiment, a detector can be mounted on the parting line to detect fluctuation in clamshell dimensions. A Hall Effect sensor is an example. Another example is a laser sensor to detect distance.

In another embodiment, the distance between two levers attached to the clamshell measured by any of a variety of means (such as a laser) measured over time describes the change in clamshell cross-sectional area. An air bladder in the clamshell is inflated until the inner cross sectional area no longer fluctuates because the inflow of blood has stopped. As the air bladder increases in size, the clamshell is expanded open against the spring type device near the hinge point, increasing the nearly circumferential pressure around the limb until blood flow into the limb ceases. The pressure in the air bladder is then reduced slowly. When the fluctuation in clamshell dimensions appears, the pressure in the air bladder is assumed to be the systolic blood pressure. As the pressure is reduced further, there will be a reduction in pulsation as the blood flow becomes continuous when the pressure in the bladder is less than the diastolic pressure. This will be the diastolic blood pressure, which can be displayed. In another embodiment, there is no air bladder. Instead, the spring pressure is increased to increase the closing pressure of the clamshell. The spring pressure can be increased by a number of mechanisms. For example, the spring can be turned manually or using a motor to increase spring tension. An air bladder can be inflated under or over the spring. Electromagnetic force can be applied by energizing a magnet or bringing it into opposition with an oppositely polarized magnet. Alternatively, a constraining cable can be placed on the spring and the length of the cable (or constraining device) can be increased to "unleash" the closing force of the spring.

Patients undergoing medical transport or procedures often lie on a mattress. Described above is a mattress with cabling where medical wires or other sensor conduits are routed through the patient mattress. The specific type of monitoring equipment needed for individual patients varies from person to person. In addition, the site of attachment may vary from person to person. For example, the blood pressure may be taken from either arm or leg, depending on the patient's injury or anatomy. Similarly, a pulse oximetry may be attached to the fingers, toes, ears or other body parts. Electrocardiographic leads may be attached from 2 to over 12 locations.

Herein described is a medical device consisting of a support structure that patients can lie, sit or stand on, where there are multiple attachments for sensor leads, such as electrocardiogram leads, pulse oximeter leads, ultrasound transducer wiring, or blood pressure cuff air tubing channels. In this invention, the leads can be reversibly attached from one or more of two or more ports, such that the unattached ports will be automatically inactive by virtue of the receiving port not having a sensor input attachment.

In the case of a blood pressure measurement system, at least two ports in the support structure are available for sensor attachment. For example, in an oscillometric method blood pressure cuff the sensor is attached to a pressure gauge by tubing so that the oscillation in pressure in the cuff can be measured and the blood pressure can be calculated. Since the blood pressure cuff could be attached to the right or left arm or leg, it would be advantageous to have a receiving port at multiple points in the support structure. An open tubing system with multiple openings would vent the system to ambient air pressure, eliminating the signal from the air bladder in the blood pressure cuff. A one end the tubing is connected to the air sensor. At the other ends, the tubing branches into multiple outlets. In the first embodiment, a valved system is provided which is bias-closed, whereby the insertion of the tube from the blood pressure cuff into the receptacle opens the valve and connects the cuff bladder to the sensor. The other ports remain closed because of the bias-closed valves. In one embodiment, the valves are passive. In another embodiment, the valves are active, such that opening of one valve closed the others. The active valve can be driven by electricity and can communicated with each other wirelessly or by conductors.

One potential problem with the tubing system connected multiple ports is that the air volume of the tubing system increases. That could make oscillometric blood pressure detection more difficult. The problem is solved by creating an internal valving system that closes the unused ports from the main tube to the sensor, unless the receiving port is activated. The connection between the active receiving port and the remainder of the tubing system can be accomplished by fixed wire or through a wireless signal. In another embodiment, all tubing leads directly to an individual sensor such that the tubing is not interconnected and where the presence of an oscillating air pressure is sensed and the sensor is activated.

In an alternate method, the system may be valved so that all tubing lines run through a multi-port rotational valve. This valve may be controlled so that only one pressure cuff may be activated at a time as the others are shut off. Orientation of this valve may be manually controlled, or automated by sensors that indicate which port is in use to select valve orientation.

Patients undergoing a variety of medical procedures have electrical current passed through the body for diagnostic or therapeutic purposes, such as defibrillation of the heart, electrocautery for surgery, or radiofrequency ablation of tissue for heart rhythm problems. In most cases, a ground wire is attached to the patient. The wire is usually mounted to a broad conductive member and coupled to the patient using a conductive gel. In this invention, a conductive element is described that is integral to the procedure mat, such that no additional ground is required. The patent is coupled to the ground upon lying on sitting on the device.

Similarly, electrodes for an electrocardiogram or electroencephalogram are attached to the skin using a conductive gel and adhesive agent. Electrodes may be imbedded into a part of a procedure mattress, chair or head covering, whereby the coupling occurs without the need for external wires or cables. In an alternative embodiment, the electrical signal is sensed using capacitive leads that are integral to the mattress, chair or head-covering. The leads are connected to a monitoring device or display by mean of a cable that attaches to the mattress, through radiofrequency or other forms of wireless transmission, or where the monitoring device is a part of the mattress.

In another embodiment, the mattress is foldable. The foldable mattress will facilitate its use in emergency patient transport where the rescuer can rapidly transport the mattress to the patient's location, unfold it, and immediately obtain physiologic information from the patient and begin to apply therapy.

Therapeutic hypothermia has been used to improve the outcome of patients suffering cardiac arrest or circulatory collapse. By slowing metabolism and oxygen consumption, organ salvage and survival is enhanced. One problem is that cooling in the field has been difficult and cooling in the hospital is often delayed by the time it takes to apply the cooling equipment. In addition, cooling of the brain, an essential organ very vulnerable to hypoxia, is slowed by the skull, which is a heat sink. A head apparatus is provided with one or more thermistors to sense the cutaneous temperature of the skull. In addition, the body of the apparatus contains one or more cavities. The cavity(s) are connected to a pressurized gas reservoir and an exhaust canal. A pressured valve can be actuated, whereby the pressurized gas flows into the cavity(s) and due to the rapid pressure fall, the cavity is rapidly cooled.

In one embodiment, the thermistor(s) control the flow of gas to the cavity(s) individually or together by use of a feedback loop, whereby the gas is controlled to achieve a set temperature. This will prevent freezing of the scalp while achieving maximal cooling. In another embodiment, a thermistor sensing core temperature would also provide feedback to the regular valve(s) to reduce flow when a set level of core or brain temperature was achieved. Core temperature thermistors can be located in the rectum, blood vessels, ear canal (as a tympanic membrane sensor), and eyes (as a retinal temperature sensor, esophagus or other locations.

In another embodiment, the head covering would also cover the neck. The neck contains the blood vessels leading to and coming from the brain. Cooling the neck to aid in brain cooling.

In another embodiment, the gas flow chambers could be perfused with a chilled fluid, with similar controls by the thermistors feedback loop(s).

A guiderail is described that attaches directly to the patient mattress rather than its supporting structure. This guiderail allows for equipment to be fixed to the mobile mattress, so that when a patient is transferred from table to table, the mattress may be moved along with the associated equipment without the need for shifting leads or monitors. In one embodiment, the rail itself contains electrical power, pressurized gas, and data communication/control access that can be accessed through attachments to the rail. This allows the development of ancillary devices that need not have large batteries or connections to electricity through a long cable to a point outside the operating table area. Moreover, creating a common standard for electrical power (for example 24 volt direct current) would help standardize medical devices attached to patient care beds. The access to data communication cables would allow for control of remote devices or remote control of devices mounted to the rail.

It is anticipated that this rail attached to the mattress may have communication with the mattress either through a dedicated bridge or through the structural attachments to the mattress. The mattress body can contain electrical power source from a battery, generator or connection to a power source outside the mattress. Typically such connections are direct current. Power outlets located on or near the rail provide a place for the connection for a variety of medical devices, including a heart pump, resuscitation devices (such as a device that administers chest compression), a defibrillator and intravenous infusion pumps. In addition, computer processing units located in the rail provide the electronic means of signal processing for physiologic signals, control of medical devices within or attached to the mattress, and for routing of electronic or optical signals in the rail or mattress. An advantage of placing the processing units in the rail is that they are easily accessible, they can have control surfaces on the rail, and there can be an associated battery in close proximity in the rail.

Similarly, the mattress can have a supply of gas within the mattress body or a supply of gas from a source outside the mattress. The gas source is within the bed mattress, within or attached to the rail, or from an outside source that attaches to the rail by tube or other conduit. The outlet for the gas is also positioned on the rail. Examples of outlets are simple nipples for attachment of tubing and quick connect valving. Control of gas flow occurs either at the outflow site, the inflow site or within the rail using standard regulators and gas control valves. In one embodiment, the valving apparatus is controlled by a motor or magnets and can be actuated wirelessly or using a control cable to a remote switch within the rail.

Data communication for the cable attachment in the rail can be transmitted wirelessly to a control unit not on the rail through a transmitter in the rail or to the mattress (by wire attached to the mattress or wirelessly). In another embodiment, power and data cable could be directly attached to the rail from an outside source (such as hospital line current with or without a power supply and isolation source), or hospital computer network, or directly to a device not mounted onto the rail. Additionally, data transmission between devices mounted on the rail can be communicated though the rail communication system.

It is also anticipated that the rail would be used to help people or machines transfer patients from one supporting structure to another. In particular, the rail can be designed such that it mates with an automated patient transport device, where the mechanical attachment is matched to the transport device configuration. In addition, it is anticipated a wireless radio signal or signals, or other positioning apparatus (such as a magnetic field), or a radiofrequency identification device (RFID) located within the rail or attached mattress could facilitate localization of the mechanical attachment of the transport system to the mattress and the identification of the specific mattress. The geometry of the mattress rail may be such that it allows for quick connection and disconnection of monitors or other equipment.

In this invention, a system is described for providing radiation protection of the personnel in the room of a patient undergoing a radiographic examination. X-rays directed at and through patients for medical procedures (such as angiography, transcatheter therapy, and orthopedic operations) cause backscatter radiation as the x-rays are deflected by the patient's bones and tissue. This backscatter radiation is hazardous to personnel in the environment. Shielding systems have been developed for personnel, but they have significant drawbacks that have limited their use or effectiveness. Wearable body shields are heavy and only provide protection of the covered body parts. The arms, lower legs, head and neck are often exposed. Skull caps and glasses have limited effectiveness. Fixed shields mounted to x-ray table or the procedure room ceilings are bulky and inconvenient. Although the above described shielding systems such as wearables or fixed shields are commonly in use, there are only a few systems that address personnel exposure by efficient anatomic shielding of the patient's body. These include mats of various size that are positioned on some parts of the patient's body to reduce scatter radiation. However, these disposable mats offer limited scatter protection, frequently fall of the procedure table during table or patient movements and are impractical to use to cover large areas of patients anatomy.

Shielding has been limited somewhat by the need to move the x-ray tube and detector all around the patient in order for the physician to examine the body from different angles. Here, an x-ray shielding system is described that is comprised of an elastic member with radiation attenuating properties that is mounted to or on the table or procedure mat the patient is on, such that the system can easily be pushed aside by the x-ray system.

In one embodiment, the system in composed of a foam material, with or without a support layer to allow shape retention in its natural state but allow distortion with minimal force. The foam is loaded with radiation attenuating material, such as BaSO4 or boron species.

In one embodiment, the radiation protection shield is attached reversibly to the arm board of the patient table or mattress. In another embodiment it takes the form of a drape over the patient with a reflecting member that rises in a vertical manner. The combination of these two embodiments provides a radiation blocking box around the radiated area, such that the operator located inferior to the patient's shoulders would receive less radiation backscatter.

In another embodiment, a radiation attenuating shield is integrated into a roller mounted along one side of the mat or procedure table, rail or another object adjacent to the patient. A plurality of rollers is envisioned of multiple widths and radiation protecting characteristics to be used to cover various parts of the patient's body. In one embodiment, once the patient is positioned on the mat or procedure table, the radiation shields at the appropriately desired levels are pulled over the patient's body. The free edge of this roller sheet is expected to mate with the opposite side of the mat or table or rail or another object adjacent to the patient via a securing mechanism that could include magnetic contacts or hooks or another mechanism that would be easy to detach intentionally. These rollers could vary in width depending on the patient's anatomy, such that a wider band might cover the patient's limbs and abdomen and a narrower band might be used in other areas such as the neck. The rollers also could be oriented horizontally or in a vertical or oblique plane such that they could easily be pulled over the patient and also easily retracted at the end of the procedure or also during the procedure if a need arises to visualize areas covered by the roller. In another embodiment, the radiation shields have areas of differential radiation attenuation characteristics. Areas of minimal or low radiation attenuating properties over portion of the body expected to be required for visualization and adjacent areas on the shield that have high radiation attenuation properties for areas of the body that generally do not require visualization during the procedure. This ability to customize level of attenuation offers the advantage of achieving higher degree of scatter radiation protection than currently being used in clinical practice. In addition, the radiation shields could have openings located in certain areas to allow the operator access to areas of the patient's anatomy (such as the femoral artery for percutaneous vascular procedures). These openings when not required could be covered by radiation attenuating flaps or another similar mechanism that would allow easy repositioning to create openings in the radiation shields. FIGS. 1 and 2 show two versions of the radiation protection offered by the roller system. In one embodiment of application of these rollers, a patient is positioned on the mat with the operator performing a cardiac procedure. The roller is deployed to cover the patient's abdomen and shows two circular openings for accessing the femoral artery. The detachable flap over the right opening is removed and the operator is using this opening to access the right femoral artery, the left opening overlying the left femoral artery has a radiation attenuating flap in place that has not been removed.

In another embodiment, the operator is at the head end of the patient performing a procedure which requires access to the heart from the neck. There are two vertical rollers and a horizontal roller that cover the right and left chest and upper abdomen while leaving the access area and area of the heart requiring visualization exposed. This detachable roller system also has the advantage of being brought into use outside the sterile field and applied to offer highly efficient radiation protection by customizing the areas of the patient's anatomy that would require to be seen by the operator while eliminating or drastically reducing the radiation from the patient's anatomy that does not require to be visualized.

In another embodiment, there is a hollowed outer member of roller sheet and a separate radiation attenuating mobile inner member that could be extended and retracted into the outer member based on the extent of radiation protection coverage required by the operator. In one embodiment shown here, the outer member of the roller is drawn across the patient's abdomen and pelvis, but the radiation attenuating inner member is only extended over the right half of the abdomen and pelvis as the operator is accessing the left sided femoral artery. Once the need for accessing the artery is completed, the operator can fully extend the inner member to provide complete radiation attenuation over the abdomen and pelvis for scatter protection. The inner member can be moved inside the outer member via various mechanisms. One such embodiment envisions the inner member to have magnetic properties such that it could easily be moved forward or backward in the outer member by application of an external magnetic force. Similarly, the inner member could also be extended via a motorized fashion. This system offers the advantage of being able to not break the sterile shield but at the same time offer customizable radiation protection by mobilizing the inner member.

In another embodiment that there could be a spring-loaded roller sheet that can drop down from the table to the floor and can be pulled back in as needed to get out of the way of the X-ray apparatus.

Cleaning of the radiation shields housed in the rollers is required to be able to reuse them and to prevent the potential spread of infectious agents from one patient to another. One embodiment envisions the application of UV C light housed in the opening of the rollers such that they would sterilize the radiation shield as it is rolled in or out of the housing before and or after each use. The UV C light would simultaneously be directed to the top and bottom surfaces of the shield while it is rolled into or out of the housing. Another embodiment envisions use of a sterilizing liquid in the roller housing.

Electrocardiogram leads are typically connected to a patient at specific locations on the body. In the most common ECG, a total of 10 leads are connected to the body, six of which are at specific locations on the chest, defined by anatomical landmarks (specifically, the sternum, ribs and clavicle). Typically, a disposable conductive patch is adhered reversibly to the patient's skin in each location desired for lead attachment. A conductive lead is then attached to the patch by a variety of mechanisms, including snaps and clasps. Attachment of wire leads to these location is clumsy and prone to error because the wires can be attached to the wrong leads. In addition, the labor of attaching multiple leads adds to cost.

Previous solutions described include integrating all the electrodes into one single larger strip or a pad like structure which is then attached to the patient's body as a single piece with integrated cable or lead connections to minimize connection errors and also ease placement. However these systems have not gained much acceptance as they are large and unwieldy or do not overcome the problems posed with poor adhesiveness of the patches to the patient's body or fully account of variations in patient's anatomy (such as the need for multiple sizes to accommodate for smaller or larger patients or needing to alter electrode placement to individualize for patient anatomy).

Described are methods for attaching leads using a disposable conductive patch placed on the skin of patients at the location desired to have an ECG lead and a roller similar to that described for radiation protection, where the inner surface of the roller contains a grid of electrically conductive material that is attached to an electrically conductive pathway to an ECG machine or to an electronic processing unit. In one embodiment, electrically conductive patches would adhered to a patient's skin at the points where an ECG lead is desired (typically, left and right arm, left and right leg, and six leads on the chest). A conductive gel with a surrounding adhesive material on the skin side is one type of conductive patch. The rolled lead array has a first end that is rolled on a spool and a second end that can be pulled to unroll the lead array from the spool. The rolled up lead array and enclosure are typically located to the patient's right or left and affixed to a fixed object, such as a table rail. The second end is unrolled across the chest or body. The second end is attached to a fixed object on the other side of the patient, typically the opposite table rail. The roller has areas of conductivity (such as a layer of electrically conductive metal or polymer) that are closely spaced. Each conductive areas (or cells) are connected in an isolated track that may be electrically shielded by a second or third layer of conductive material. The other end of the roller sheet could be secured to the opposite end of the table or could be envisioned to have some weight or spring force which allows it rest on the electrodes while providing the mild compressive force to secure them. Alternatively there could be a magnetic attachment mechanism between the electrodes and the cables.

In one embodiment, an opposite end of the tract is connected to an electrical processing unit. The electrical processing unit (EPU) detects if the cell of each lead is substantially in electrical contact with the body, which occurs when the cell is placed into contact with a chest patch that is conductive. Electrical contact of each cell is detected if the cell has a fluctuating voltage consistent with an ECG signal. Alternatively, the resistance between the lead and a ground lead connection to the patient can identify a cell that has electrically active contact. The electrical processing unit, then determines the identity of each lead by an algorithm using the cells position on the roller grid. For example, the right arm chest lead is always the lead most to the patient right upper side. Lead V1 is the next lead to the left at mid position on the grid, and so on. The identified leads are then routed to the appropriate lead connections on the ECG processing and/or display device.

It is anticipated that more than one cell could be in contact with a conductive pad. In that case, the EPU would group signals from adjacent pads that were in substantial electrical connectivity with the body. Alternatively, the cell with the greatest voltage fluctuation, lowest resistance to the ground, or other connection detection method could be selected as the primary or only lead cell used in the contiguous area.

The roller sheet can be spring loaded, similar to a window shade. The roller sheet is connected to the display system using standard connections or wirelessly. The system can be modified to include radiolucent electrodes and radiolucent integrated leads in the roller sheet for applications that require the use of the EKG monitoring in procedures requiring the use of x-rays. One example of radiolucent leads is a radiographically homogeneous grid, such as an aluminum foil or a fabric or loymer loaded or coated with conductive material.

It is also anticipated that the roller lead array could be combined with standard ECG leads wired to the patient.

In another embodiment the roller sheet has an integrated stretch or motion sensor that monitors respiratory rate and quality of the respiration or change in quality of the respirations based on the excursion of the patient's chest wall or via an acoustic sensor detecting air flow through the airways.

Operator could be alerted when the patient might be breathing too slowly, rapidly, too shallow or having apneic spells.

Most modern x-ray units have what is referred to as automatic brightness control, where the x-ray dose (in terms of photon number and energy) is controlled by a feedback loop from the detector to the x-ray source, such that the dose is increased to provide a set level of x-ray intensity at the detector. The importance of this is that elements in the x-ray field that homogeneously absorb x-ray may not appear visible to the operators. Therefore, a radio-opaque electrical conductor that homogeneously covers the radiographic field would appear to be invisible to the operator. If that material was interposed between the x-ray source and the patient, the dose to the patient would be unaffected.

Conduction of electricity in a conducting agent occurs more on the periphery of the conductor than in the core (the so-called "skin effect"), especially when high frequency electrical signals are conducted. Therefore, maximizing the ratio of the conductor surface area to the total cross-sectional are could be advantageous. The invention described here incorporates the principles of homogeneous conductors within the x-ray radiographic field that have a very flat profile which results in low radio-opacity and a very high surface area to cross-sectional area ratio. Additionally described is a simple manufacturing method to make a set of shielded conductors with the described attributes. These conductors are used to conduct signals for medical monitoring. They are nearly invisible to x-ray imaging and carry high current load with wire bandwidth.

Thin aluminum strips increase the surface area/cross-sectional area ratio and the "skin" effect for conduction. Aluminum strips (typically less than 0.003 inches thickness) and of any width, but typically 2-10 mm, are mounted onto a radio-lucent insulating material. The material is applied to both sides of the strips. When shielding is required, a second layer of thin aluminum material (typically less that 0.003 inches thickness) is mounted onto each side of the insulated strip. The shields are connected to provide a 360 degree shield. Multiple conductor ribbons can be mounted in parallel to the insulating layers. The insulating layers can be joined between each conductor or left open, where insulation between conductors is obtained by lack of contact due to the fixation to the insulating material. Similarly, the shield can be connected on the sides of each conductor or only on the sides of the conductor ribbon array.

The conductor starts with a sheet of foil, typically less than 10 thousandths of an inch thick. The conductor may be aluminum because it has less radio-opacity, although any conductor would suffice (such as copper, iron alloys, gold, platinum, conductive polymers, and carbon-based conductors). The roll of foil is divided along its long axis into conducting tracts by cutting the foil with a knife, laser or other means. The tracks are separated slightly and mounted onto a non-conductive material, such a polypropylene. This could occur as a continuous automated process. Then, a non-conductive material is mounted to the opposite side of the conductor, isolating the tracts electrically from each other and from adjoining conductors. This could also occur as an automated process, and also nearly simultaneously to the cutting and first side application of the non-conductive material. Then, a foil of conducting material, ideally aluminum, is applied to both the top and the bottom of the enclosed conductor ribbon and joined at the edges to create an electrical shield. This action could also occur as an automated process at a similar time to the cutting, and application of the non-conductive materials. Finally, a layer of insulating material may be applied over the shield, as needed. That material could consist of polymer, fabric or any flexible insulating material and could occur as part of an automated process.

In an alternative manufacturing process, strips of thin foil precut to a desired dimension, could be joined to a non-conductive surface instead of cut foil. In addition, the shield material could be joined between conductor members to shield each conductor or set of conductors individually. In addition, a single sheet of foil could be placed around the insulated conductive ribbon and joined to create a shield.

In another embodiment, fine wires arranged along the same plane and positioned in contact with each other, or flat wire could be used as the conductors.

In another embodiment, the insulating material is a non-conductive paintable or spray-on material such as the array of flat conductors could be coated and then placed directly on the shield material.

In another embodiment, a pattern can be cut into the conductor foil such that the conductors turn corners for connections or to fit the contour of the housing into which it is placed. In a further embodiment, the width of the tracts could be varied based on the anticipated electrical signal to be carried by the conductor. In a further embodiment, more than one layer of divided foil conductors could be mounted on top of each other, preserving the relative homogeneity of the x-ray absorption.

In a further embodiment, connection between conductors within one foil or between foils would allow creation of electrical circuits where on conductive track is connected to another. The connection between conductors from one sheet to another can be accomplished though a foil conductor. One problem encountered when monitoring patients undergoing x-ray or MRI procedures is that the wires are visible to x-ray or the electromagnetic field can induce heating or current within the wire. Carbon nanotubes or variants have been developed to provide electrical connections in the environments. These conductors, however, and very expensive and provide poor shielding from electromagnetic fields. In addition, they tend to have poor conductivity, which is import when the conducted signal is of low power.

In yet another embodiment, the conductors may be printed in an array on a radiolucent insulative material, or both the radiolucent material and the conductors may be printed in a manner that lays down the insulative layers, conductive layers and shielding layers to prevent cross-talk and create a single wiring array construct.

One problem with reusable devices is contamination with biologically active agents, such as bacteria, fungi, or viruses. One method to reduce the burden of biologically active material is application of certain frequencies of photons, such as ultraviolet light. In this invention, a mattress is described where a light source inside the mattress is used to sterilize the mattress surface, by shining the light through a light transmitting cover.

In one embodiment, the light emitters are fiber optic strands woven into the cover. The strands have a removal of the cladding at areas where the mattress needs to be sterilized. In one embodiment, the cladding is removed preferentially on the side to provide lateral photon dispersion, but no allow photons to escape to the mattress foam, which might be damaging, or outside the mattress. In another embodiment, to limit the radial movement of the optical fibers and to improve durability, a bundle of two or more fibers are contained in a jacket and woven into or adhered to the mattress. In another embodiment, the jacket around the optical fibers allows differential photon passage, such that UV C light can be directed to the area that requires sterilization, but blocked to areas of the mattress that are sensitive to UV C or outside the mattress where it might damage bystanders.

UV C can be quite toxic to tissue and the present invention has an integral sensor to determine if a person or object is on the mattress. Such a sensor can be a weight or distortion detector, such as a piezoelectric detector, a light based detector that measures surface distortion, an infrared detector that detects body heat, or a surface laser light device that detects the presence of an object on the mattress surface. In another embodiment, a motion sensor is used to detect people in the room and to interrupt the photon emission. The motion detector is attached to the mattress in one embodiment. In another embodiment, the motion detector is remote from the mattress and communicates wirelessly or by conductors. The motion detector can employ any of a number of previously described methods, included sound or light reflection.

Another means to sterilize the surface of patient mattresses is the application of intense heat for a short period of time, similar to Pasteurization of dairy products. In this invention, the surface of the mattress is loaded with resistive heating wires located close to each other. With the application of current through the wires, the mattress surface heat rapidly. When on or more thermistors located within the mattress reach a pre-specified temperature, the current is reduced or interrupted. As an alternative, a combination of temperature and time could be used to signal that maximum effect had been achieved and effect a reduction or elimination of further heating.

In an alternative embodiment, the heating elements are attached to or layered under a heat conductive cover. This cover can be composed of a metal, such as aluminum or a polymer, glass, or fabric loaded with a heat conductor. The heat source would provide heat energy and the conductor facilitates a more even spread of the heat. This reduces the peak temperature and time needed to treat because the heterogeneity of heat distribution is reduced.

Alternatively, other heat sources can be used, such as a heated fluid or air, and exothermic chemical reactions.

Safety measures similar to those described for use with UV C sterilization may also be employed to prevent the activation of the heat mattress disinfection when a patient or operator is in contact with the mattress.

Determination of tissue oxygenation and blood flow has been described and performed using a variety of methods, included pulsed oximetry and laser Doppler methodology. Its application in a medical and non-medical environments has allowed for monitoring of patients in hospitals and clinics, and for monitoring of sleep apnea and exercise performance. Monitoring requires the user to attach a sensor to the skin. The sensors are usually handheld or fixed to the skin with adhesive.

In this embodiment, a sensor is mounted in a mattress or other device that people sit or lie on. The sensor sends and receives its signal through a transparent window in the device onto the subject body.

In a related device, the subject also wears a specialized clothing that also contains a window for transmission and reception of the signal, such that the signal can be transmitted through the mattress or other device and then through the wearable clothing.

Another embodiment is aimed at preventing pressure sores and ulcers related to prolonged compression of skin and muscle while laying down or sitting. Lack of blood flow leads tissue ischemia and eventually necrosis. This embodiment includes a mattress containing a multitude of sensors for oxygen concentration and/or tissue blood flow. The sensors are located below the surface of the device, but send and receive their signal through the surface of the device in contact with the patient. The output from these sensors is displayed visually on a monitor. In one embodiment, the display is a color or greyscale coded picture of the support structure, where the color or grey scale correspond to a range of values from the sensor. In further embodiment, a similar display shows a calculated value derived from multiple patient values. For example, the product of blood flow and oxygen saturation. In another example, a user or computer entered value such as the patient's hemoglobin concentration or body surface area, would be used in the calculated value that is displayed. In another example, the calculated value could result from a calculation of one or more user or computer entered values (such as height and weight), and one or more sensed valves.

Patient undergoing medical procedures or surgical operations usually lie on a mattress or sit in a chair. They are frequently deeply sedated or completely unconscious for the procedure. The head is often instrumented for placement of sensors (such as EEG leads, temperature probes, and pulse-oximeter leads), control of respiration using an endotracheal or endonasal tube, and various devices that cannulate the stomach or esophagus (such as endoscopy catheters, trans-esophageal ultrasound transducers or nasogastric tubes). In some cases the head is covered by a sterile drape, making access to the head and communication with the patient cumbersome. Moreover, the head is poorly supported, leading physicians to tape the head to the operating room table or mattress.

The invention described here is a molded head support that stabilizes the head and neck, while at the same time providing a platform for the mounting of sensors (such as EEG, temperature, pulse oximetry, ECG, video observation of the eyes and airways, exhaled CO2), attachment of probes and tubes (such as endotracheal tube, endoscopic devices, ultrasound devices, and tubing for medical gasses), and communication with the patient (speakers and microphone). The wires or fiberoptic connection to the sensors are passed through the head support. In one embodiment, cables to external devices are attached to the head support. In another embodiment, the head support contains a radio transmitter that transmits the sensor signal to the remote display device. In another embodiment, the head support is attached by a cable or optical fiber to the mattress, operating table, or rail attached to the operating table or mattress.

Therapeutic hypothermia has been used to improve the outcome of patients suffering cardiac arrest or circulatory collapse. By slowing metabolism and oxygen consumption, organ salvage and survival is enhanced. One problem is that cooling in the field has been difficult and cooling in the hospital is often delayed by the time it takes to apply the cooling equipment. In addition, cooling of the brain, an essential organ very vulnerable to hypoxia, is slowed by the skull, which is a heat sink. One embodiment includes a head apparatus with one or more thermistors to sense the cutaneous temperature of the skull. In addition, the body of the apparatus contains one or more cavities. The cavity(s) are connected to a pressurized gas reservoir and an exhaust canal. A pressured valve can be actuated, whereby the pressurized gas flows into the cavity(s) and due to the rapid pressure fall, the cavity is rapidly cooled.

In one embodiment, the thermistor(s) control the flow of gas to the cavity(s) individually or together by use of a feedback loop, whereby the gas is controlled to achieve a set temperature. This will prevent freezing of the scalp while achieving maximal cooling. In another embodiment, a thermistor sensing core temperature would also provide feedback to the regular valve(s) to reduce flow when a set level of core or brain temperature was achieved. Core temperature thermistors can be located in the rectum, blood vessels, ear canal (as a tympanic membrane sensor), and eyes (as a retinal temperature sensor, esophagus or other locations.

In another embodiment, the gas flow chambers could be perfused with a chilled fluid, with similar controls by the thermistors feedback loop(s).

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which FIG. 1—Image of the patient mattress showing the configuration of the mattress components with a single arm board and radiation shield installed.

FIG. 15—Image of an alternate embodiment of a clip that uses a mechanical ratchet to hold the clip closed on a guidewire or catheter on the table.

FIG. 16—Image of an alternate embodiment of a clip that uses a ball and socket attachment mechanism in conjunction with a magnet to mount to the patient mattress or work table.

FIG. 34—Image showing a top view of the mattress with rails, showing a gas line connection to the rail.

FIG. 35—Image showing a top view of the mattress with rails, showing a gas system integrated into the rail.

FIG. 36—Image showing a top view of the mattress with rails, showing a gas system integrated into the mattress.

FIG. 37—Image showing a top view of the mattress with rails, showing a data and processing system integrated into the rail.

FIG. 38—Image showing a top view of the mattress with rails, showing a data and multi-processing system integrated into the rail.

FIG. 39—Image showing a top view of the mattress with rails, showing a data and processing system integrated into the rail with wireless communication and a CPU integrated into the mattress.

DESCRIPTION OF EMBODIMENTS

Figure 1:
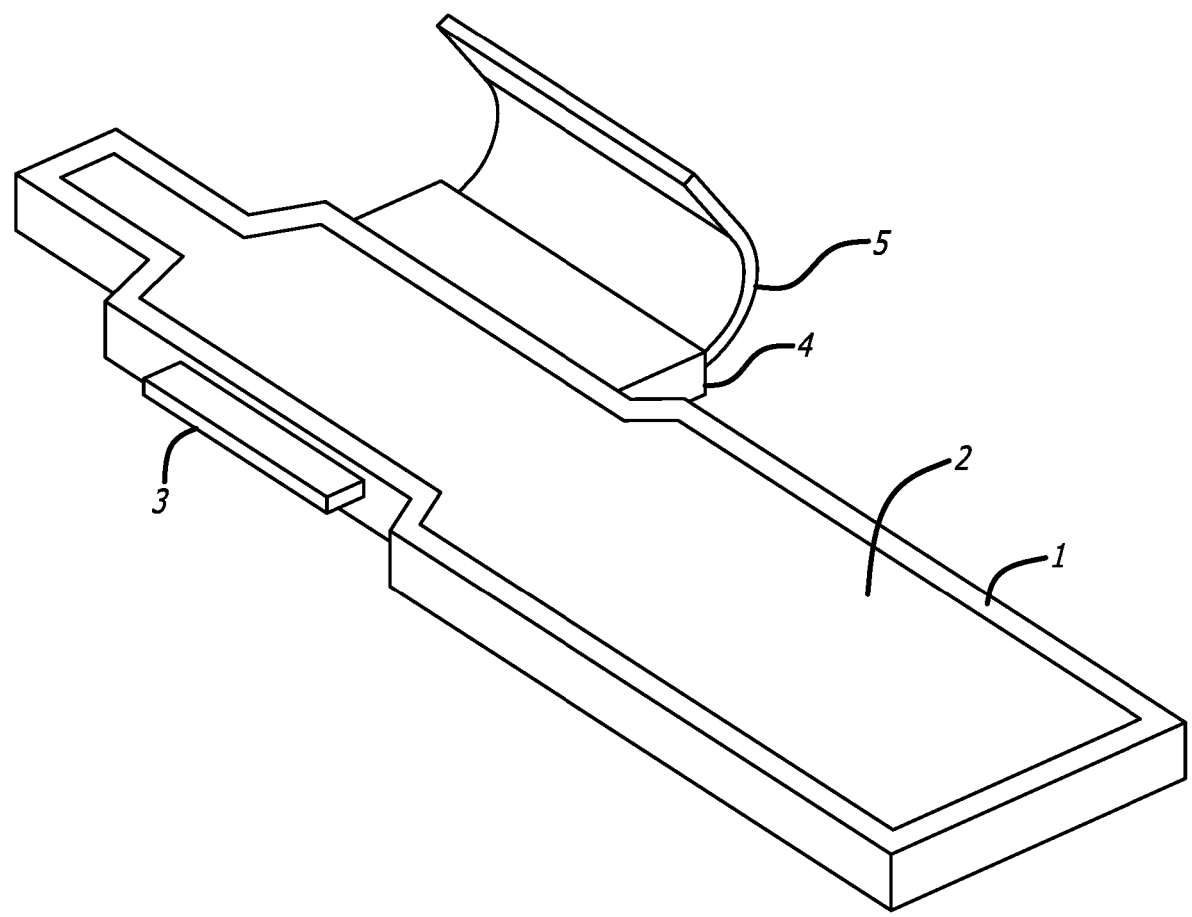

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

FIG. 1 describes the configuration of one embodiment of the mattress. There is a comfort foam component 2 housed within a relatively rigid outer shell 1. Under the torso of the patient is a more rigid component 3 that may be used to support chest compressions. The ends of component 3 may also be used to mount additional items to the mattress. In this embodiment, removable arm boards 4 are designed to be placed on the ends of component 3. A radiation protection wing 5 may be mounted to the arm board 4 to prevent backscatter radiation from reaching the staff in the cardiac catheterization laboratory.

Figure 2:
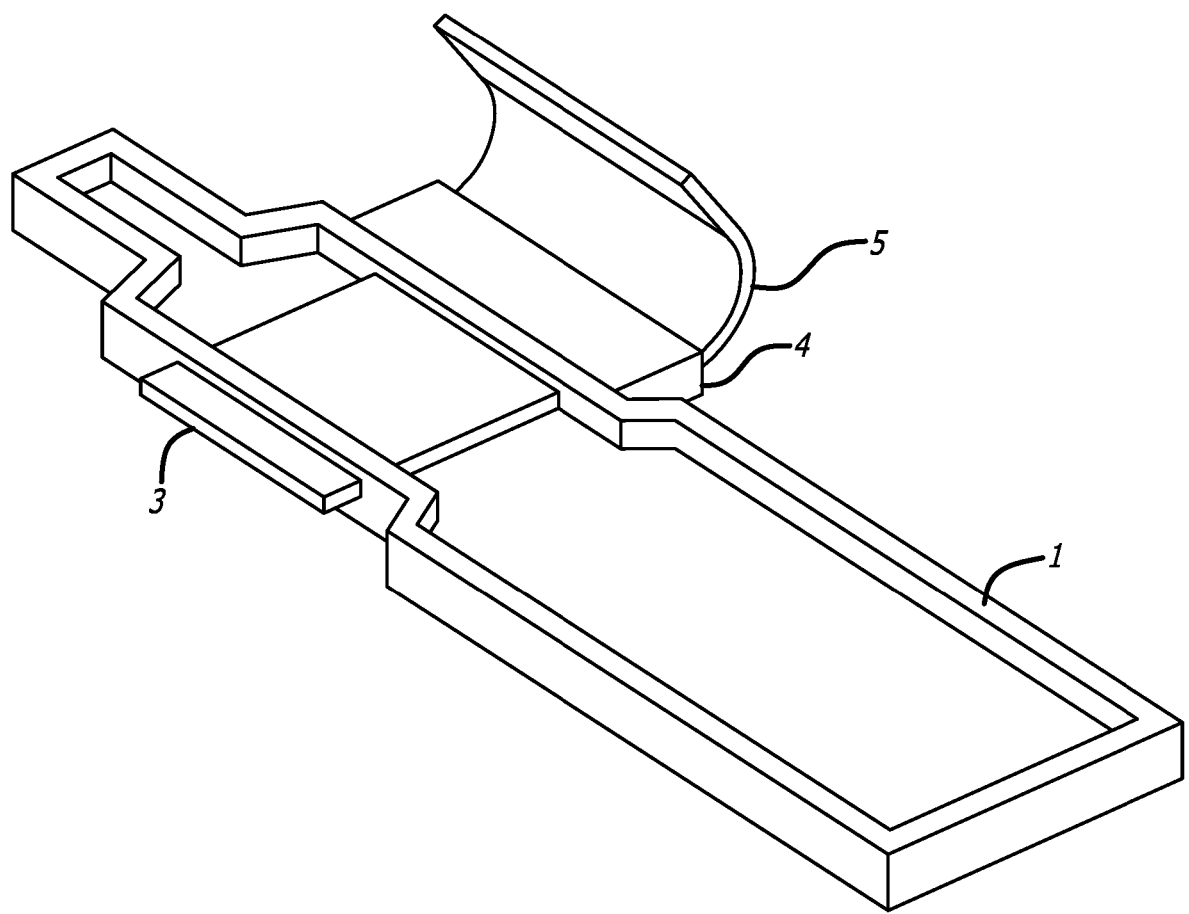
FIG. 2—Image of the patient mattress with the inner comfort foam component removed, revealing the rigid chest support component.

FIG. 2 shows the mattress shell 1 with the patient comfort component 2 removed. This demonstrates the location and orientation of the rigid torso component 3.

Figure 3:
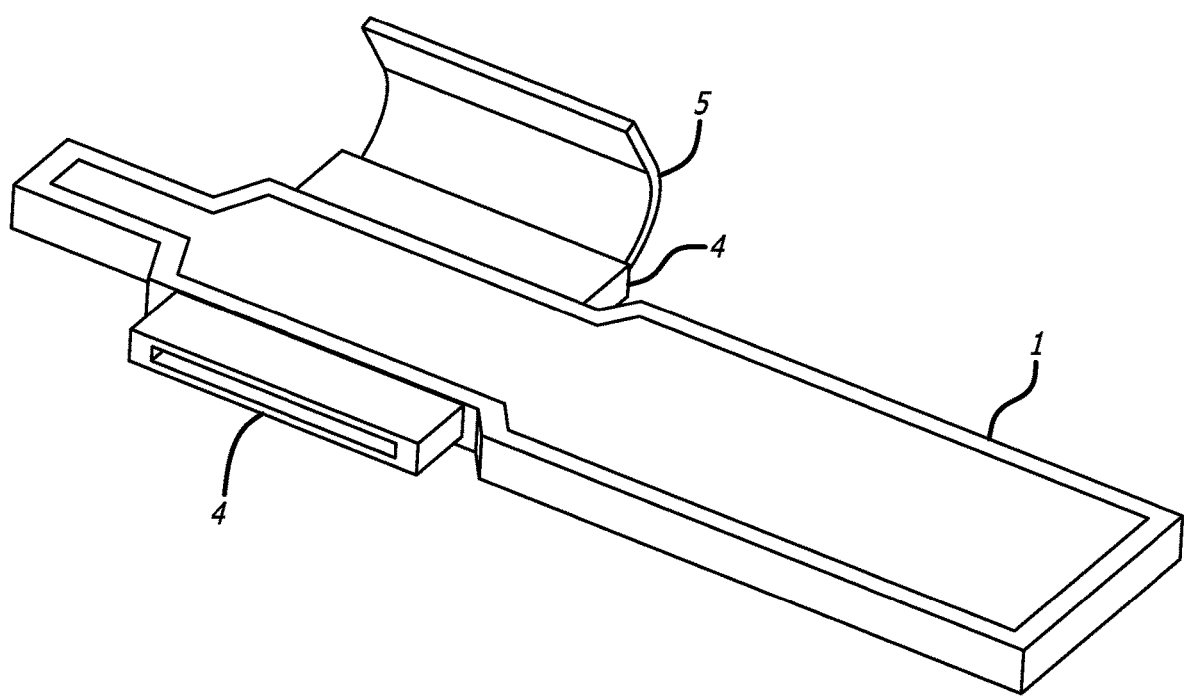
FIG. 3—Image of the patient mattress with both arm boards installed.

FIG. 3 shows the patient mattress with a second arm board 4 mounted to the rigid component 3.

Figure 4:
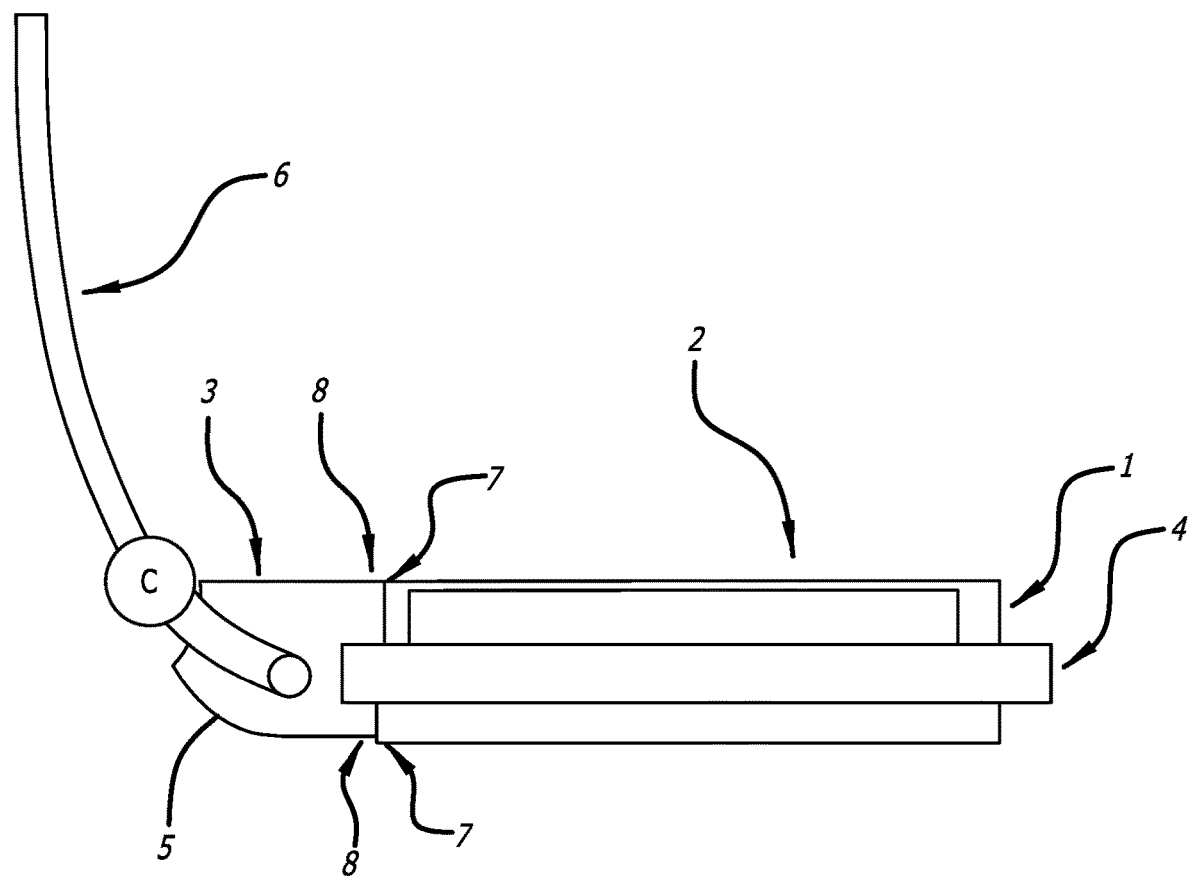
FIG. 4—Cross-sectional end view of the patient mattress demonstrating one embodiment of the component assembly.

FIG. 4 shows a cross-sectional view of the mattress that demonstrates one embodiment of the component assembly. The patient comfort component 2 resides within the rigid shell 1. The rigid torso component 3 crosses through the shell 1 and may be used to mount the arm board 4 to the mattress assembly. The radiation protection wing 5 is mounted to the arm board 4 using the receiving slot 6, which holds the wing 5 in place with either a friction fit or through the use of magnets or some other engaging mechanism. Magnetically sensitive material or a magnet 7 on the arm board 4 can also be used to affix the arm board to the side of the rigid shell 1 with a mating magnetic surface 8.

Figure 5:
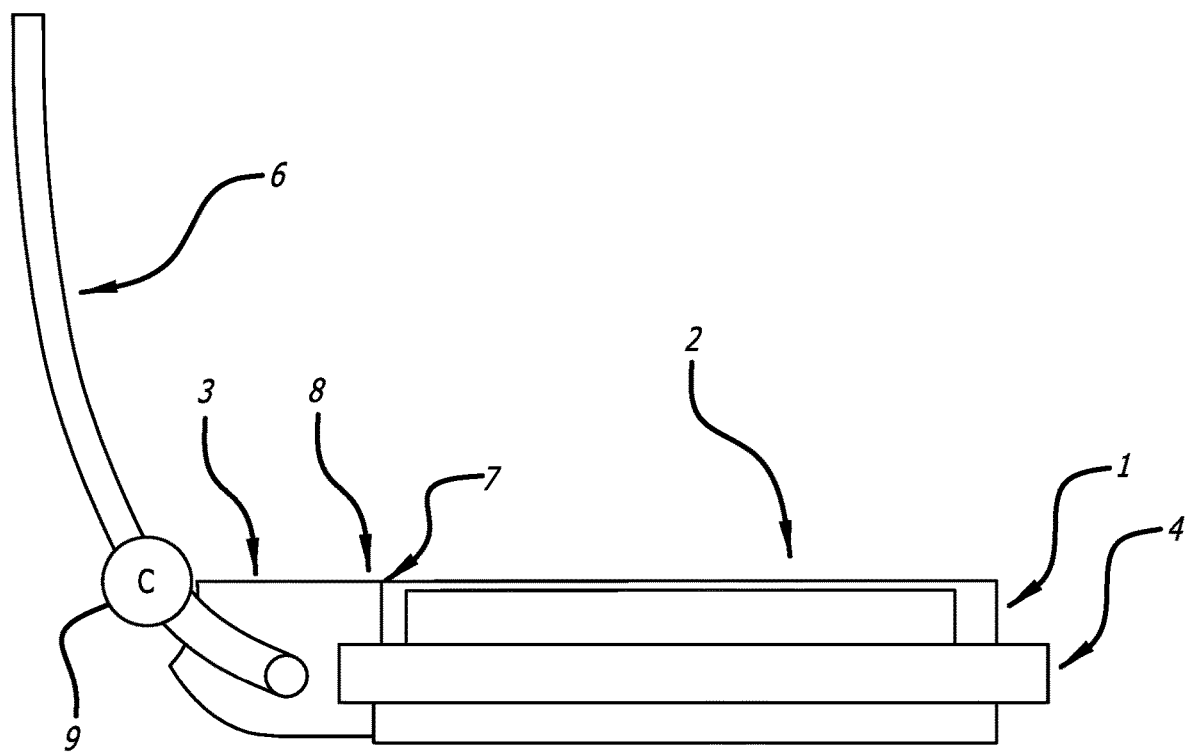
FIG. 5—Cross-sectional end view of the patient mattress demonstrating another embodiment of the component assembly that includes a hinged radiation shield.

FIG. 5 shows a cross-sectional view of the mattress similar to that of FIG. 4. In this case, the radiation protection wing 5 contains a spring loaded hinge 9 that will aid in the flexion of the wing away from the mattress if a component of a fluoroscopy unit comes into contact with it.

Figure 6:
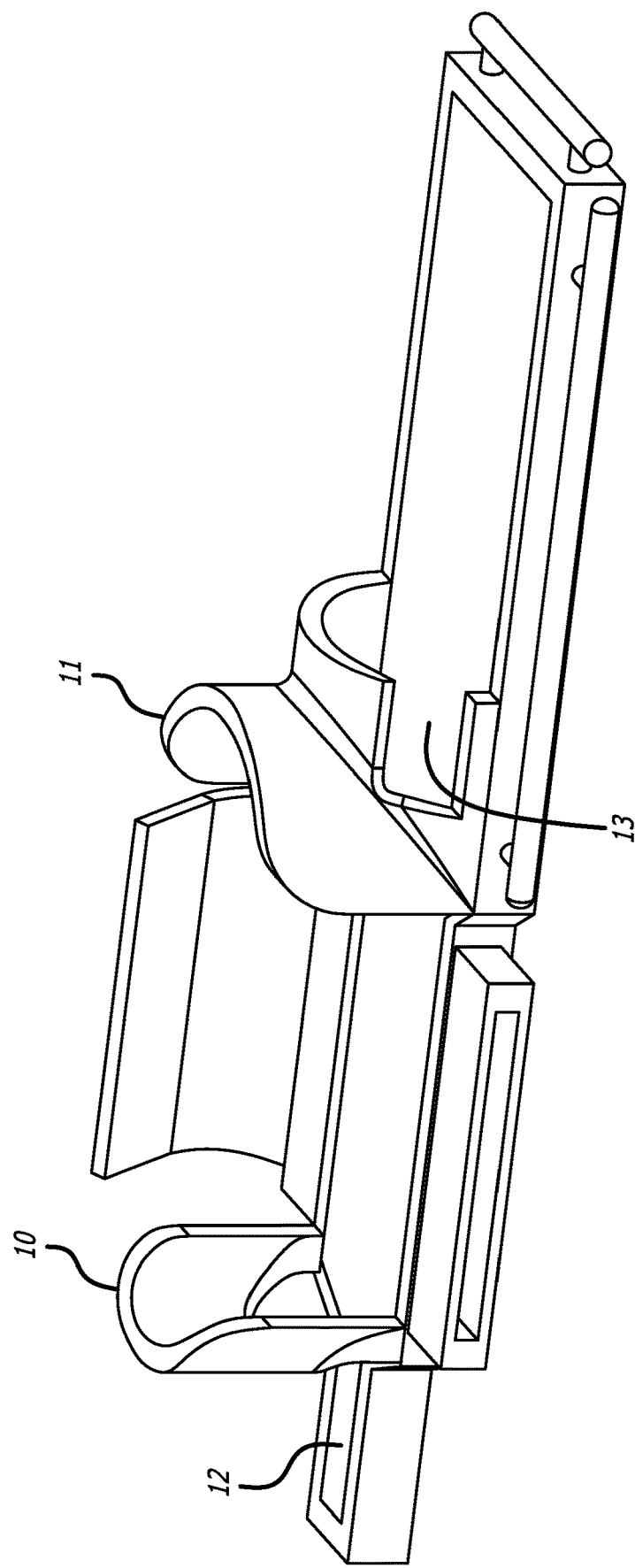
FIG. 6—Alternate embodiment of the patient mattress describing a neck and waist radiation shield component.

FIG. 6 shows additional components that are added to the mattress to provide additional radiation protection. The neck protection component 10 is placed near the head of the patient, and contains a neck cutout 12 to provide for access to the jugular vein for interventional cardiology procedures. The waist protection component 11 is placed at the waist of the patient, and may contain a femoral cutout 13 to allow for access to the femoral arteries or veins in the groin.

Figure 7:
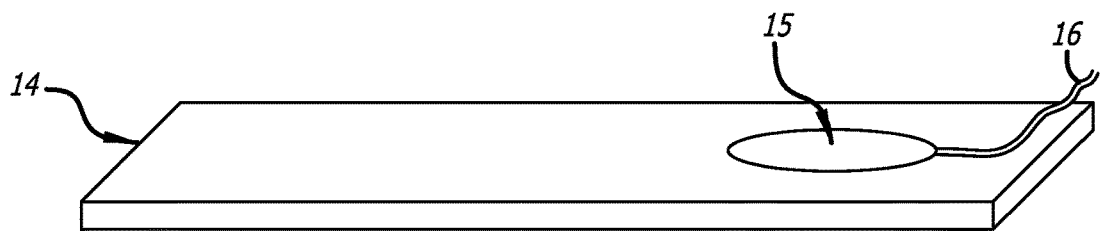
FIG. 7—Image of an integrated induction coil used to power devices placed on the table.

FIG. 7 shows an induction coil 15 that can be mounted to any working surface on the mattress, particularly the work table 14. The induction coil 15 is powered through an integrated cable 16.

Figure 8:
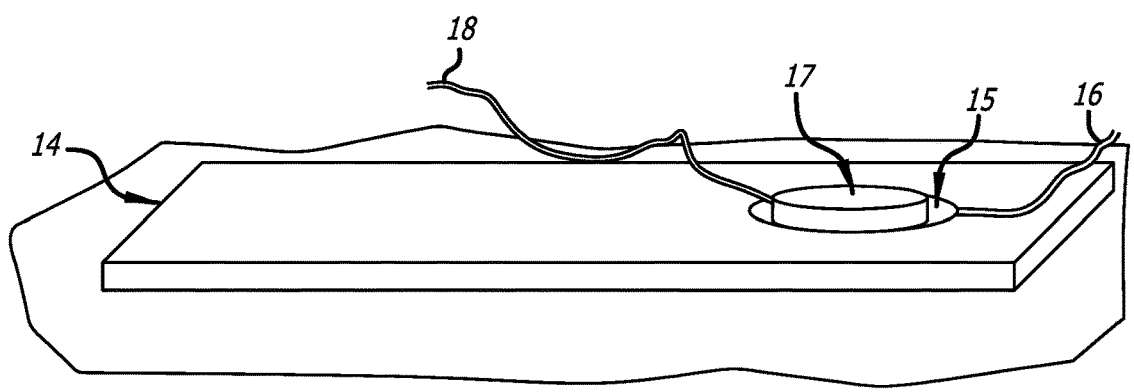
FIG. 8—Image of an integrated induction coil as used in a sterile field.

FIG. 8 shows a similar image to that of FIG. 7. A device power source 17 is placed on a sterile drape 49 over the induction coil 15. The system is designed to power that device via a power cable 17 that is designed to be within the sterile field.

Figure 9:
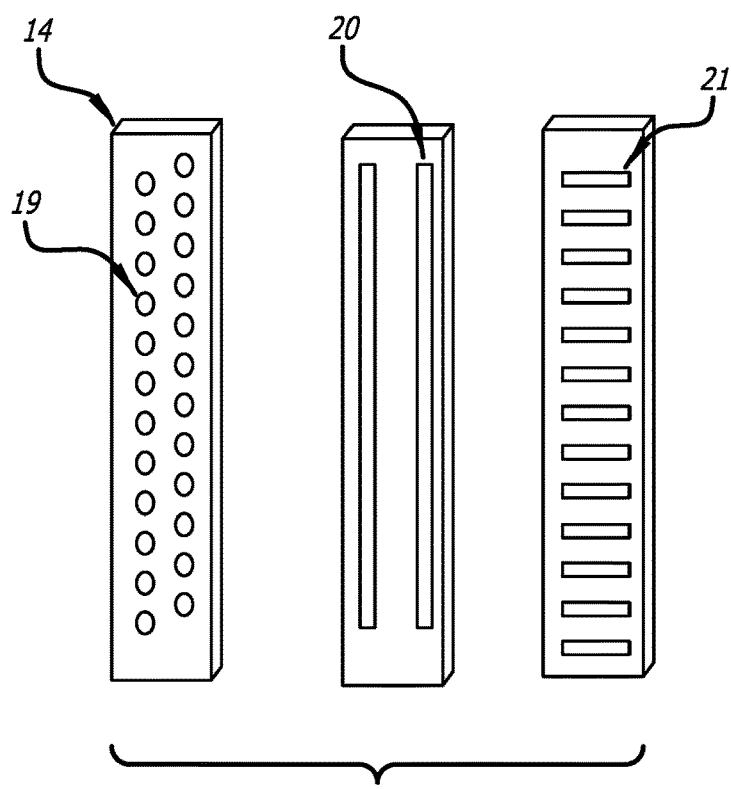
FIG. 9—Image of the work table with magnet configurations used to hold devices within the sterile field.

FIG. 9 demonstrates magnet patterns that may be used in conjunction with the table 14. Individual magnets 19 may be embedded in or fixed to the table 14. Magnetic bars 20 may also be used in a similar manner. Dipole magnetic bars 21 may be also used to ensure correct orientation of devices with similar magnets that are affixed to the table 14. These magnets are all designed to hold sterile components to the table 14 through a sterile drape 49.

Figure 10A:
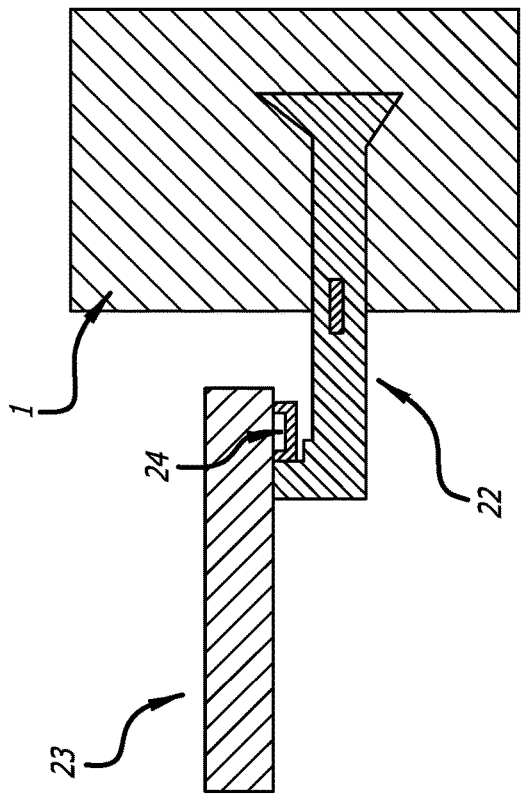
FIG. 10—Cross-sectional end view of mattress demonstrating attachment mechanisms used to connect radial table to patient mattress.
Figure 10B:
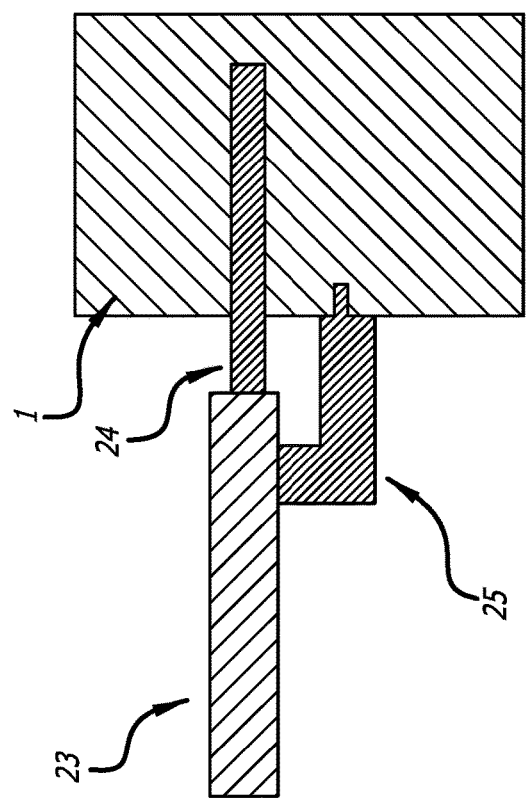

FIG. 10 describes mounting mechanisms to hold a work table 14 or radial board 23 to the edge of the rigid shell 1. A rail 22 mounted to the edge of the rigid shell 1 provides an attachment surface that can be used as an attachment point. A latch and release mechanism 24 can be used to reversibly attach the radial board 23 to the rail 22. The latch and release mechanism 24, along with the attachment surface of the guiderail, are constructed and arranged, in one embodiment, such that accessories equipped with the latch and release mechanism, such as a table, arm rest, instrumentation, radiation shields, monitors, and other equipment, may be easily attached to the guiderail and slid down the length of the guiderail to an optimal position before being locked in place. Additionally, a secondary support mechanism may be used to provide additional support to carry loads on the radial board 23.

Figure 11:
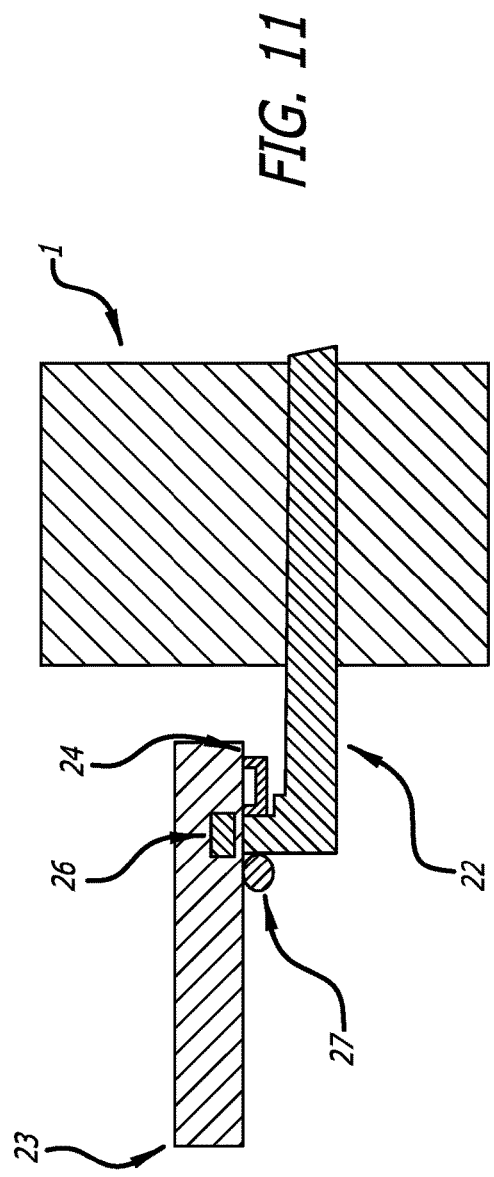
FIG. 11—Cross-sectional end view of mattress demonstrating attachment mechanisms used to mount a rotatable radial table to patient mattress.

FIG. 11 describes a similar configuration to that of FIG. 10, with the addition of a hinge mechanism 27 which allows for the radial board 23 to be rotated downward for stowing when not in use. The hinge mechanism 27 is activated by pressing or pulling the release mechanism 26.

Figure 12:
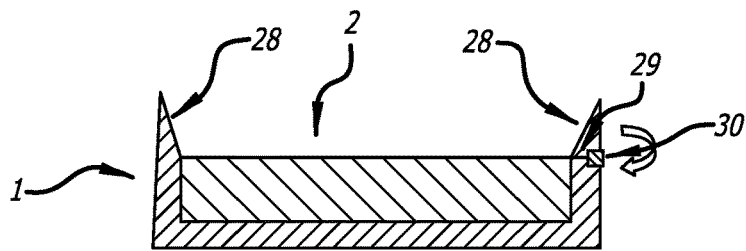
FIG. 12—Cross-sectional end view of mattress assembly demonstrating raised edges to prevent patient falls.

FIG. 12 demonstrates a mattress configuration to aid in patient transfer and to prevent inadvertent patient falls from bed. The rigid shell 1 has raised edges 28 and 29 that will resist a patient fall. These edges may be of flexible material and be able to flex out of the way, or be more rigid and have a parting line 30 where the material can more easily displace.

Figure 13:
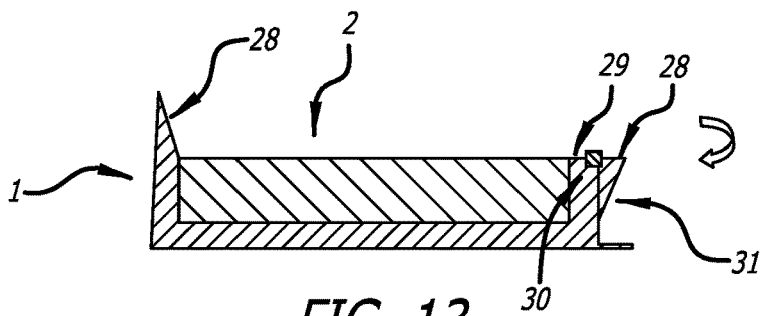
FIG. 13—Cross-sectional end view of mattress assembly demonstrating deflectable raised edges that may be used to aid in patient transfer.

FIG. 13 describes a similar configuration to that of FIG. 12, with the addition of a locking mechanism 31 that can be used to hold the displaced edge of the rigid shell 1 during patient transfer. This locking mechanism 31 holds the edge 29 in a lateral position to facilitate sliding a patient onto or off of the mattress 2 from a gurney.

Figure 14:
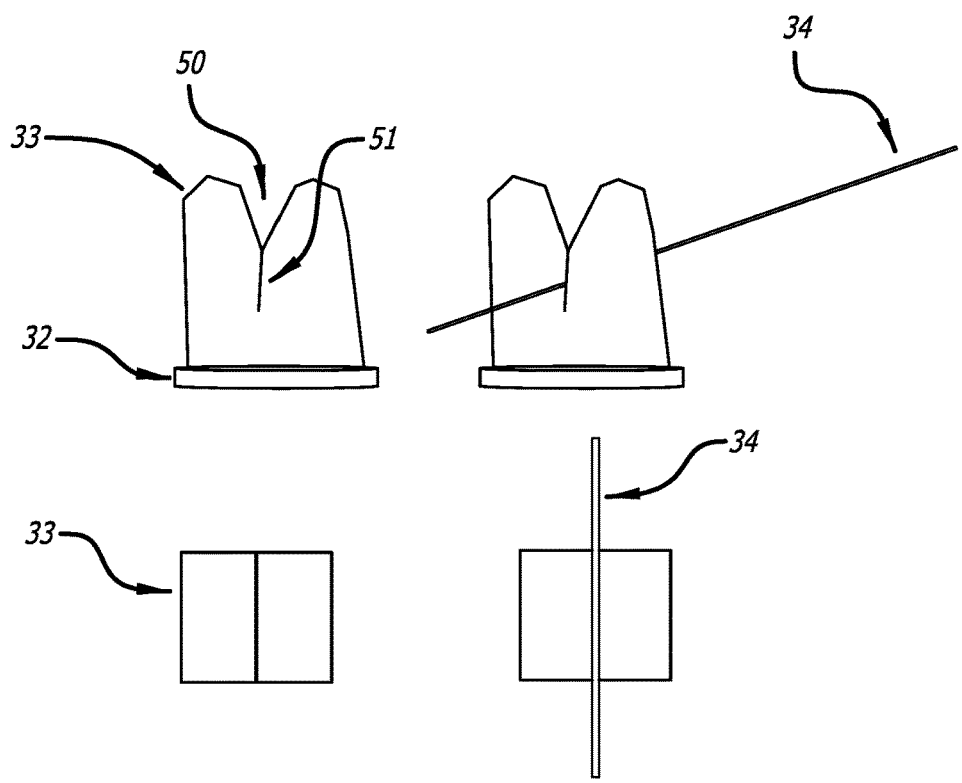
FIG. 14—Image of a deformable clip that can be used to hold guidewires or catheters in a steady position on the table.

FIG. 14 describes one embodiment of a clip used to aid in holding guidewires or catheters during interventional procedures. The body of the clip 33 is an elastomer that is partially split. The gap 50 created by the split and the slit 51 may be used to hold a guidewire or catheter 54 in a defined position. A magnetic base 32 is affixed to one surface of the clip to allow the clip to be reversibly attached to a work surface beneath a sterile drape within the sterile field of a catheterization procedure.

Another embodiment of a clip mechanism is shown in FIG. 15. In this embodiment, a first half 35 and a second half 36 are mounted to a magnetic base 32. Embedded in or attached to each half is a supporting post 37 that is mounted to the base 32. This mounting mechanism may include a hinge 38, or the posts may be of a flexible material that allow for bending. A ratchet mechanism 39 bridges the gap between the first half 35 and the second half 36. A guidewire or catheter 34 may be placed within the gap 50 between the first half 35 and the second half 36. When the first half 35 and the second half 36 are pressed towards one another, the ratchet mechanism 39 engages, holding the halves together and holding the position of the catheter or guidewire 34.

In yet another embodiment of a clip mechanism shown in FIG. 16, a secondary attachment mechanism may be used to supplement or replace the magnetic base 32 of the clip. A post containing a ball 40 may be mounted below the magnetic base 32. This ball 40 can be reversibly inserted into a receiving cup 42 on a work surface 41. This construct allows for rotation of the entire clip assembly 52, to better align the clip to a catheter or to manipulate the position of the holder during use.

Figure 17:
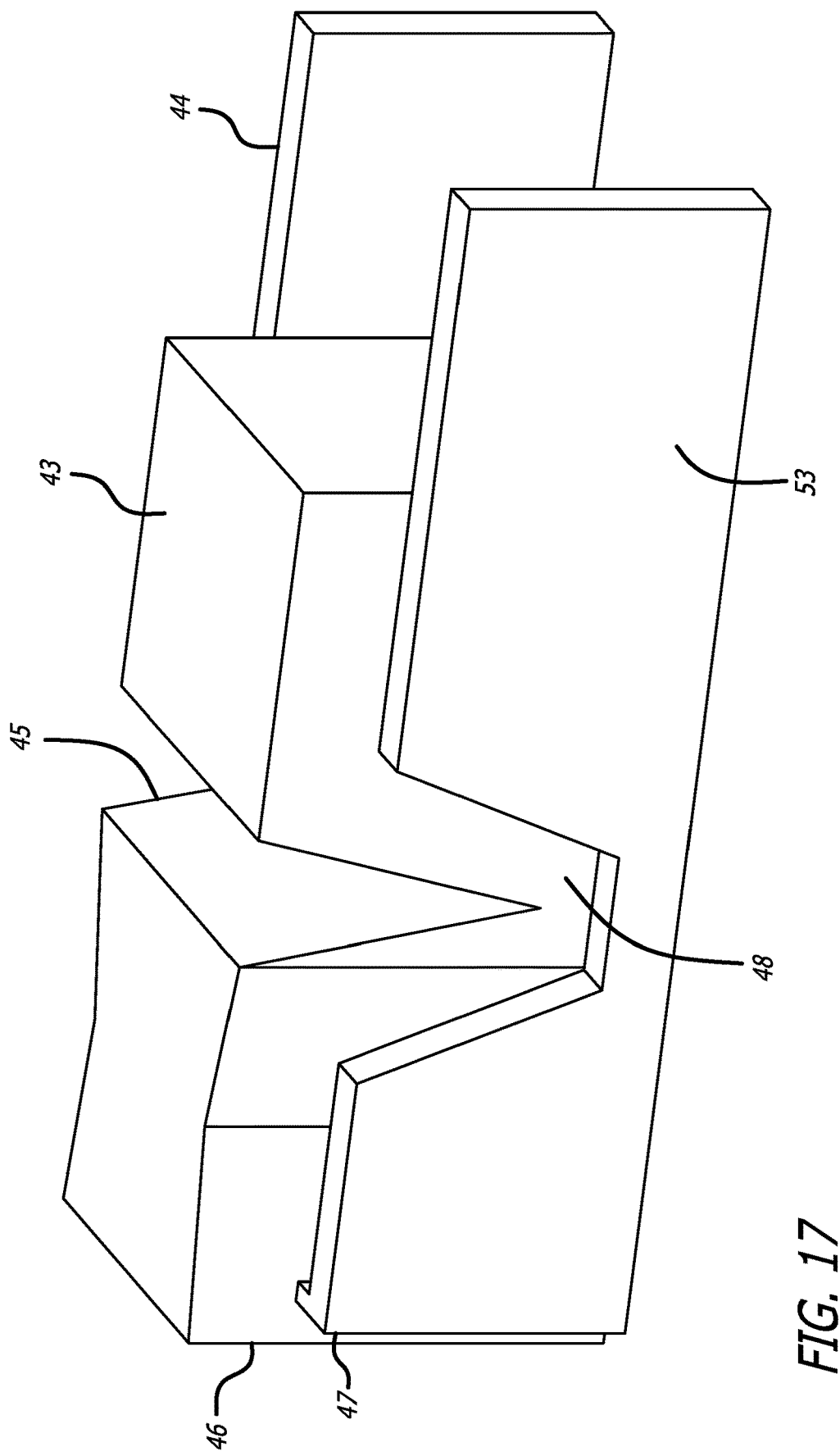
FIG. 17—Image of an alternate embodiment of a clip that uses a compressible block with retention clips to hold a guidewire or catheter on the table.

FIG. 17 describes another embodiment of a clip mechanism. A compressible block 43 contains a slit 45 for receiving a guidewire or catheter 34. Two lever arms 44 and 53 are mounted to the sides of the compressible block 43 that each have a clip lock edge 47 for engagement with the tapered block surface 46. The lever arms contain cutouts to allow for the guidewire or catheter 34 to sit in the bottom of the slit 45.

Figure 18:
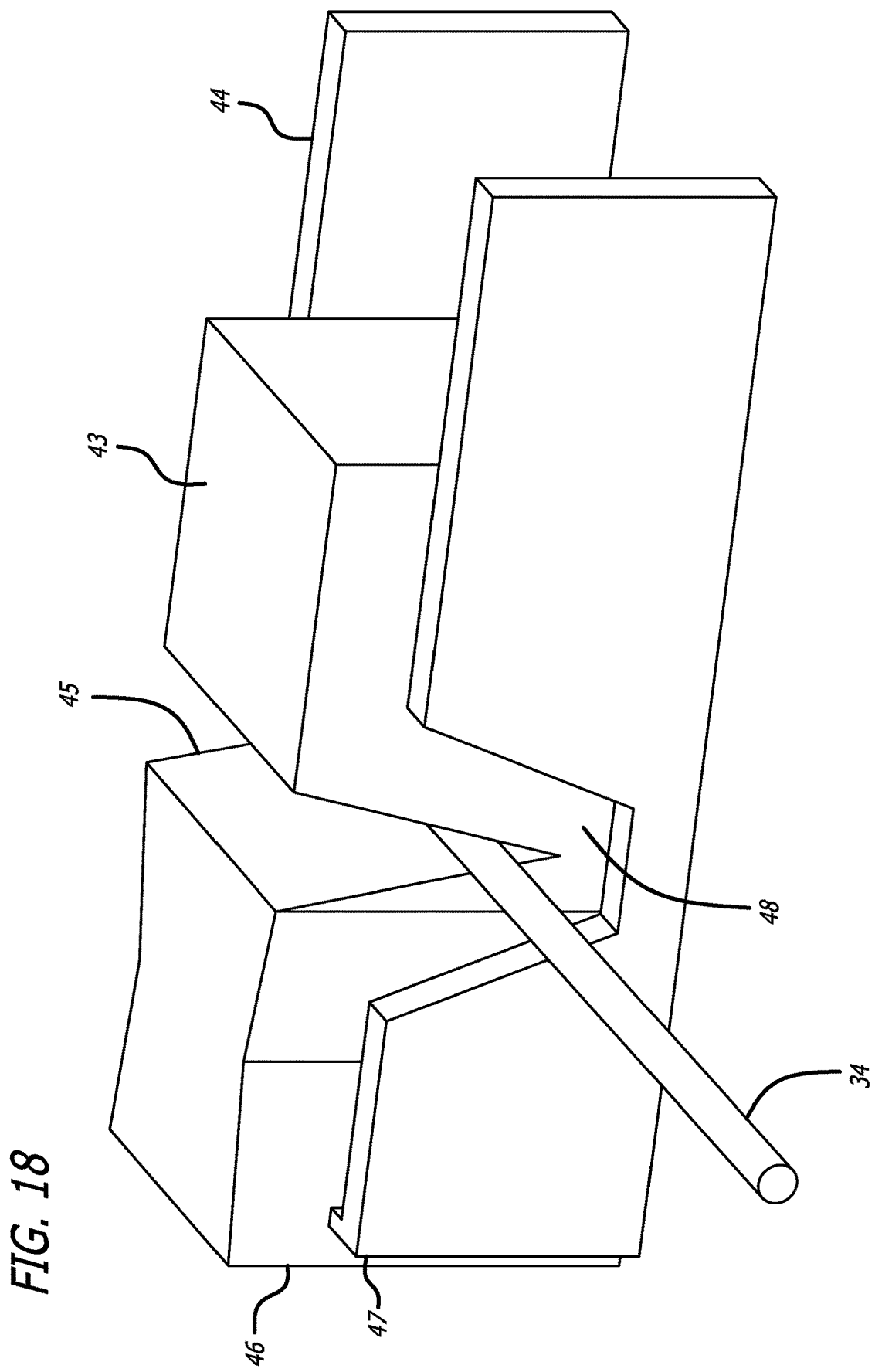
FIG. 18—Image of an alternate embodiment of a clip that uses a compressible block with retention clips to hold a guidewire or catheter on the table, shown open over a guidewire.

FIG. 18 shows the guidewire or catheter 34 placed within the slit 45, prior to engagement of the lever arm clips.

Figure 19:
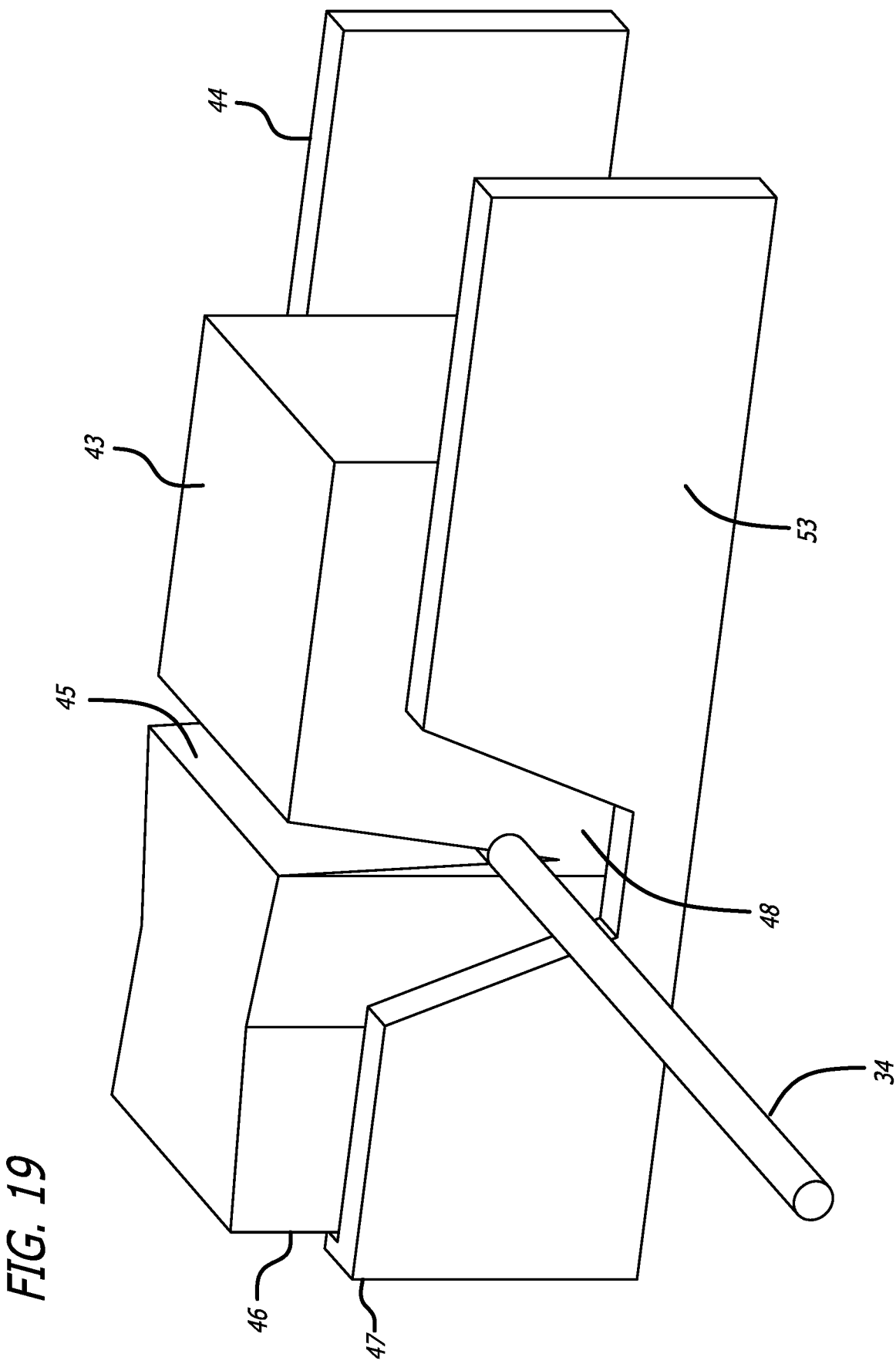
FIG. 19—Image of an alternate embodiment of a clip that uses a compressible block with retention clips to hold a guidewire or catheter on the table, shown closed upon a guidewire.

FIG. 19 shows the engagement of the compressive block 43 on the guidewire or catheter 34. The ends of the compressible block 43 are squeezed towards one another, enabling the clip lock edge 47 of the lever arms 44 and 53 to slide along the tapered surface of the compressible block 43. When the clip lock edges 47 extend beyond the end of the compressible block 43, the clip lock edges latch onto the end of the compressible block and hold it in a compressed position. This compression engages the guidewire or catheter 34 and maintains it in a fixed position. To disengage the clip from the guidewire or catheter 34, the ends of the lever arms 44 and 53 are squeezed towards one another, releasing the clip lock edges 47 from the end of the compressible block 43 and opening the slit 45.

Figure 20:
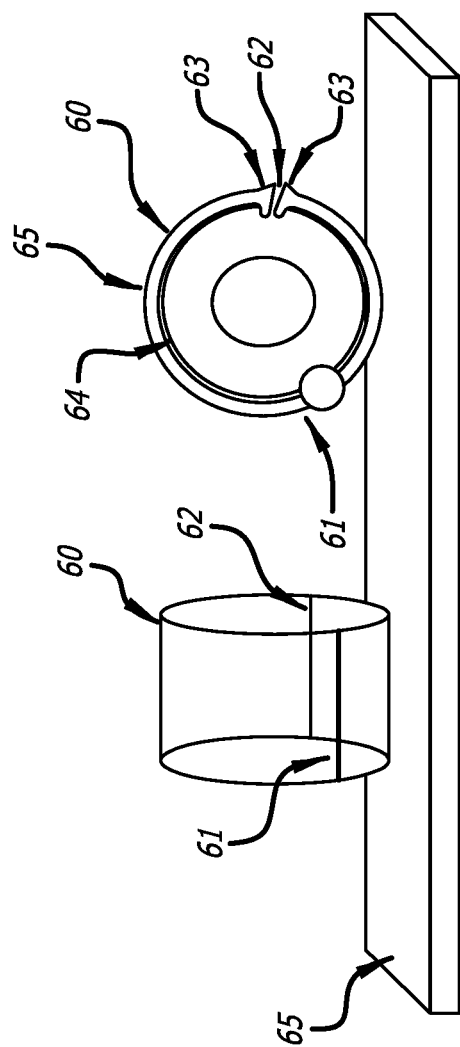
FIG. 20—Image of an integrated blood pressure cuff on the arm board or table.

FIG. 20 shows a blood pressure cuff 68 designed to be added as a component to the patient mattress. The outer shell 60 of the cuff is mounted to the table or arm board 65, and contains a hinge 61 that allows the outer shell 60 to open and close at the parting line 62 in a clamshell fashion to allow the arm of the patient to be inserted without necessitating sliding the device over the hand and arm of the patient. Clasps or magnetic attachments 63 located at the part line 62 hold the outer shell 60 closed after arm insertion. The air bladder 64 is retained within the outer shell 60.

Figure 21:
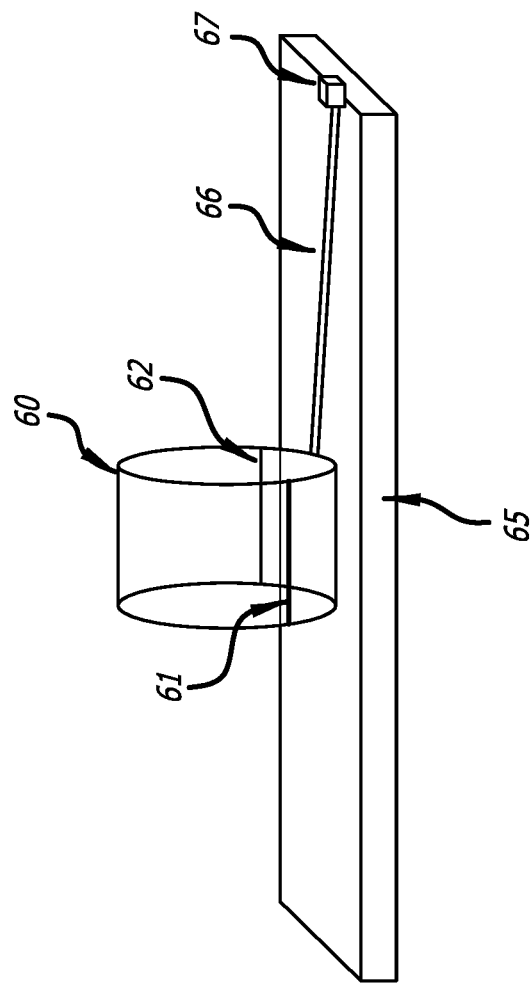
FIG. 21—Image of an integrated blood pressure cuff with tubing connection on the arm board or table.

FIG. 21 shows a side view of the blood pressure cuff 68, with the outer shell 60 mounted to the arm board 65. Blood pressure air tubing 66 is run along the surface of the arm board 65 or embedded within, leading from the outer shell 60 to a tubing connection 67 integrated into the arm board 65.

Figure 22:
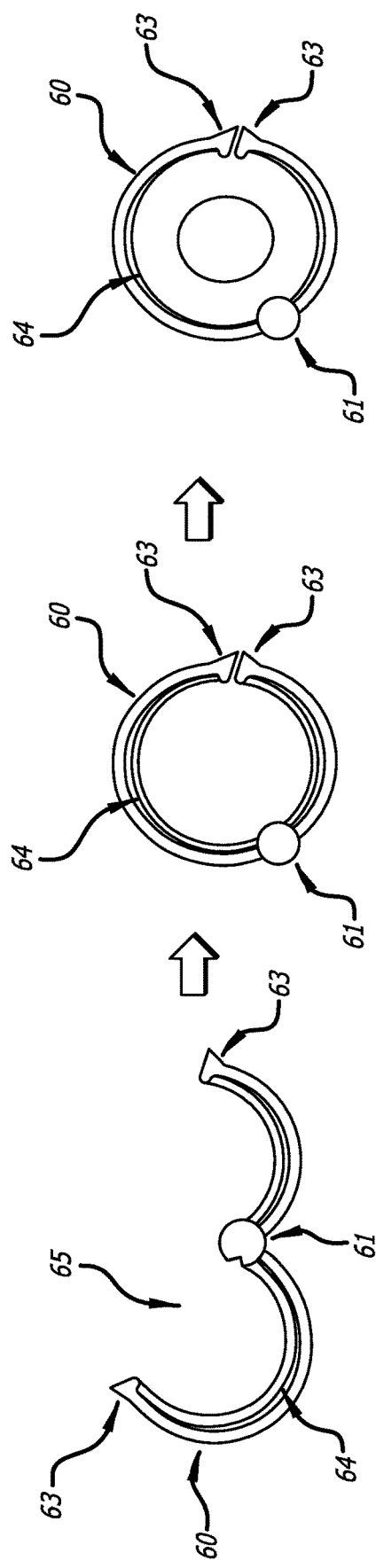
FIG. 22—End view image of a blood pressure cuff open, closed and inflated.

FIG. 22 demonstrates how the blood pressure cuff 68 is used. The outer shell 60 opens in a clamshell fashion about the hinge 61. Once the arm of the patient is inserted into the clamshell, the outer shell 60 is closed and the opposite surfaces of the parting line 62 are affixed to one another with clasps or magnetic attachments 63. Once closed and locked, the air bladder 64 may be inflated in order to obtain patient blood pressure.

Figure 23:
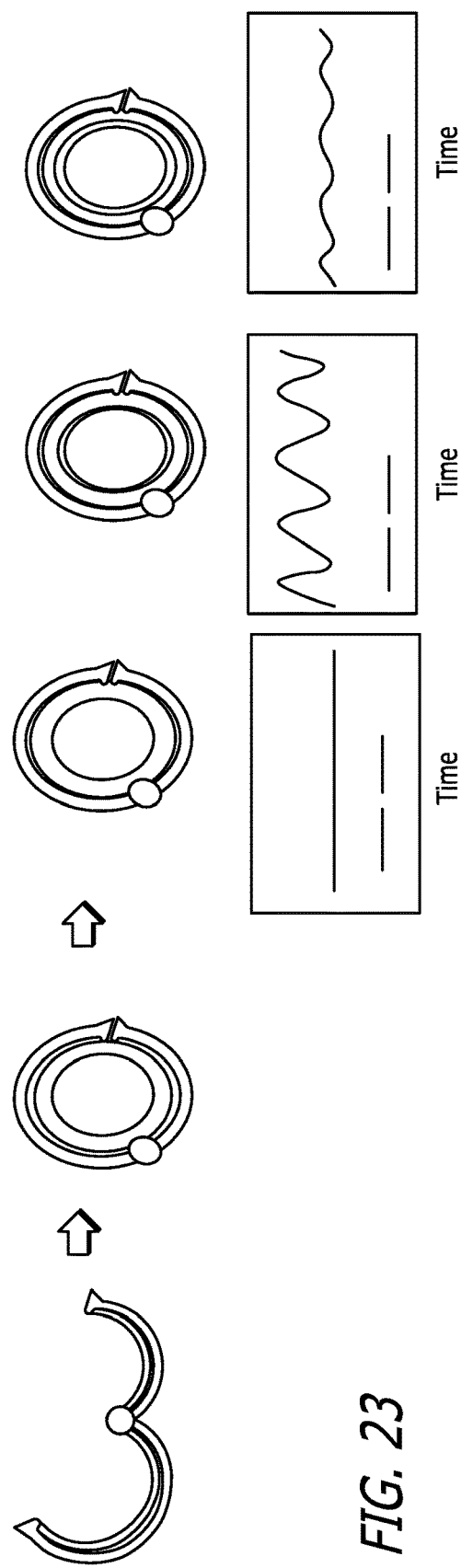
FIG. 23—End view image of a blood pressure cuff during use.

FIG. 23 demonstrates the measurement of blood pressure during the use of the blood pressure cuff 68. When the air bladder 64 is inflated fully, blood flow through the arm is stopped. As the pressure in the air bladder 64 drops below systolic blood pressure, blood flow will begin in an intermittent fashion. The air pressure in the system is then equated to peak systolic pressure. As the air pressure continues to drop, the air pressure in the air bladder 64 drops below diastolic pressure and continuous blood flow is observed. This air pressure in the system is equated to diastolic pressure.

Figure 24:
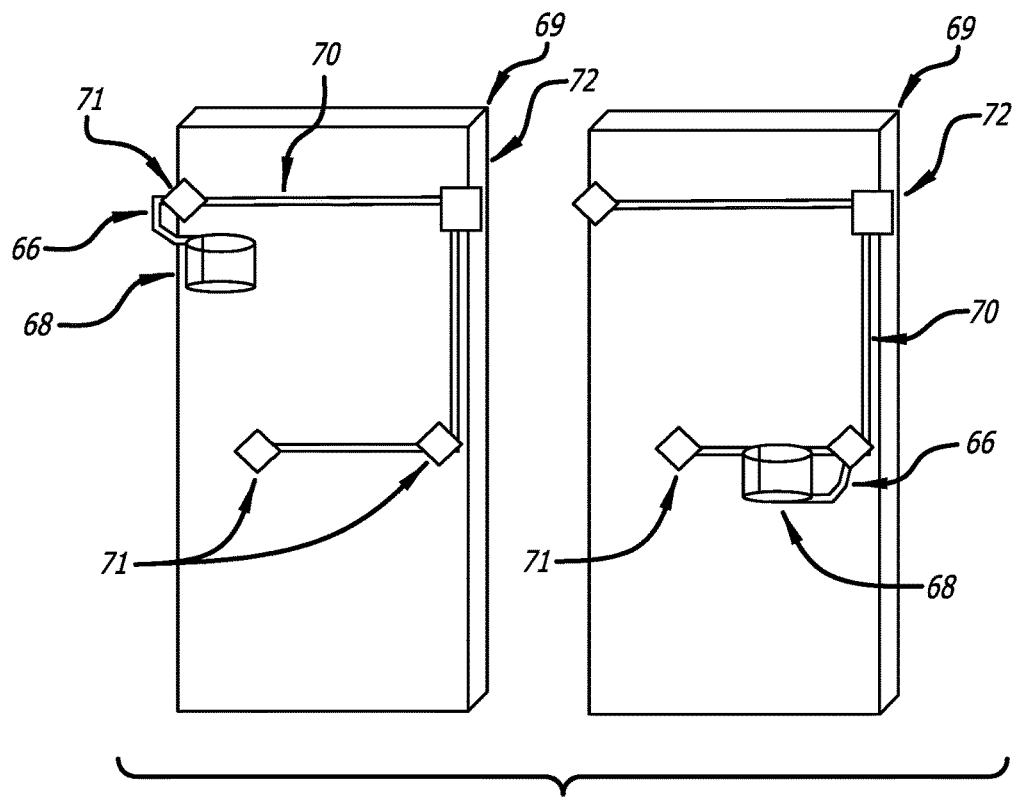
FIG. 24—Top view of the patient mattress with blood pressure cuff positions described in serial fashion.

FIG. 24 demonstrates where these blood pressure cuffs 68 may be integrated into the mattress. Air tubing 70 is integrated into the mattress 69, leading from a junction box 72 that connects to the pump and sensor to the valved receptacle 71 used for connecting the blood pressure cuff 68. These blood pressure cuffs 68 are connected to the receptacle 71 using air tubing 66. Locations of the cuff may be placed such that they can be used for either arm or either leg.

Figure 25:
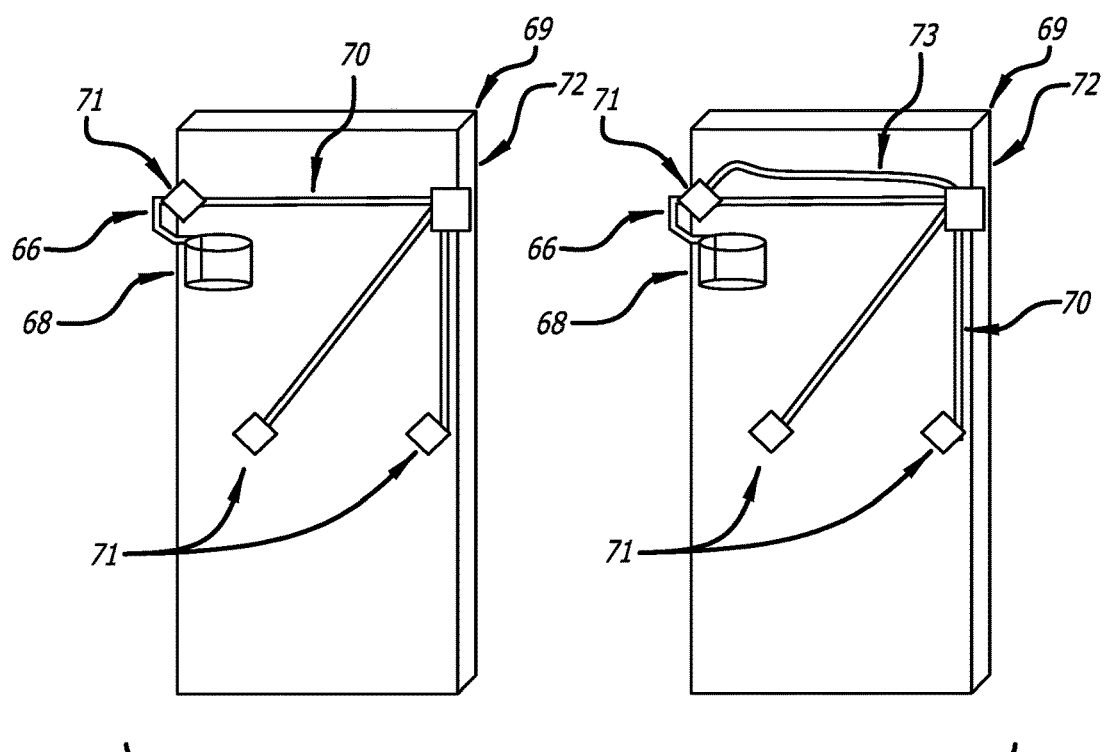
FIG. 25—Top view of the patient mattress with blood pressure cuff positions described in parallel fashion.

FIG. 25 demonstrates how the integrated blood pressure cuffs 68 can be controlled to ensure that pressure is being read from an active location. A pressure sensing control can be integrated into the integrated air tubing 70 such that the junction box 72 will pick up pressure oscillations and open the junction valve to the active tube. Alternately, a conductor 73 may be used at each local connection receptacle 71 to communicate with the junction box 72 that a connection to a pressure cuff tube 66 has been made, activating that pressure line 70.

Figure 26:
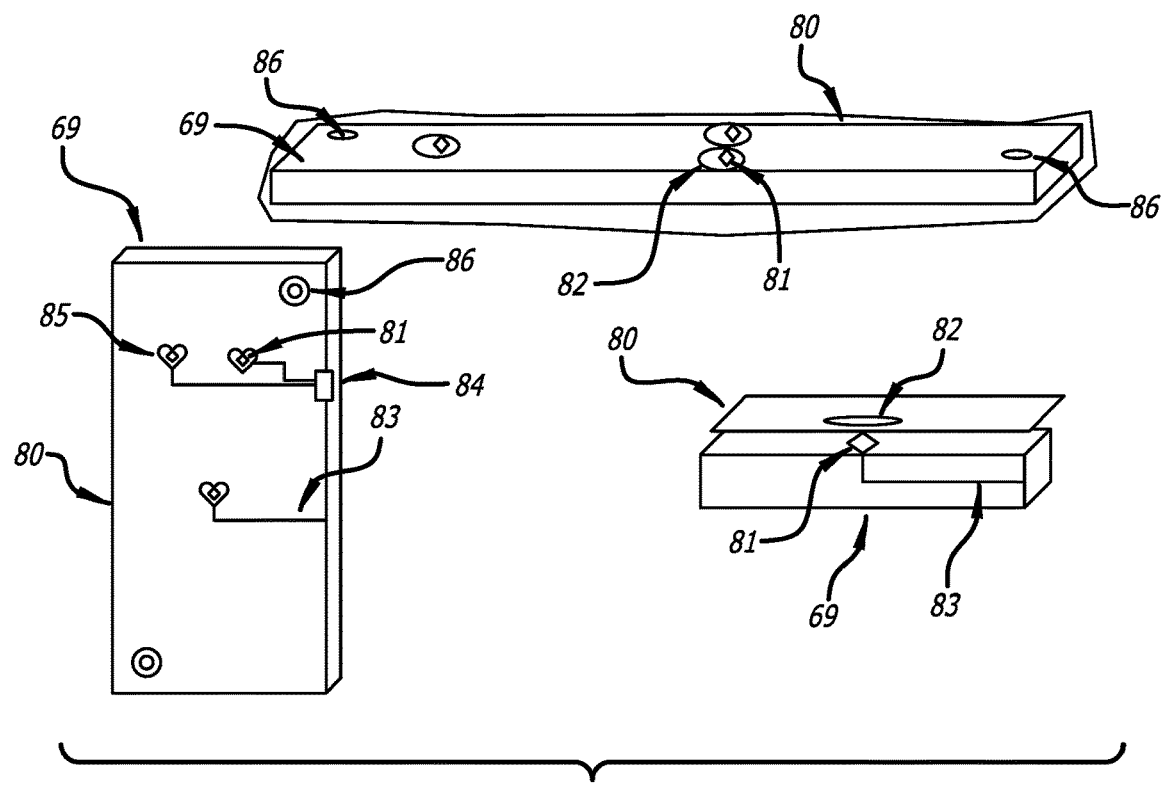
FIG. 26—Image of a mattress with electrically conductive regions or conductors for ECG use.

FIG. 26 shows electrically conductive components integrated into the mattress. The electrodes 81 are embedded into the surface of the mattress 69 with conductive wires 83 running to a junction box 84 for connection to a monitoring system. A drape 80 is placed over the mattress 69, with the drape containing electrically conductive regions 82 through which the electrical connection from the patient to the electrodes 81 may be made. In order to ensure alignment of the conductive regions 82 to the electrodes 81, reference markers 86 are placed at the edges to match up with markers on the mattress 69. Additional reference markers 85 on the drape 80 show the areas where the electrodes 81 are placed, to ensure proper patient positioning.

Figure 27:
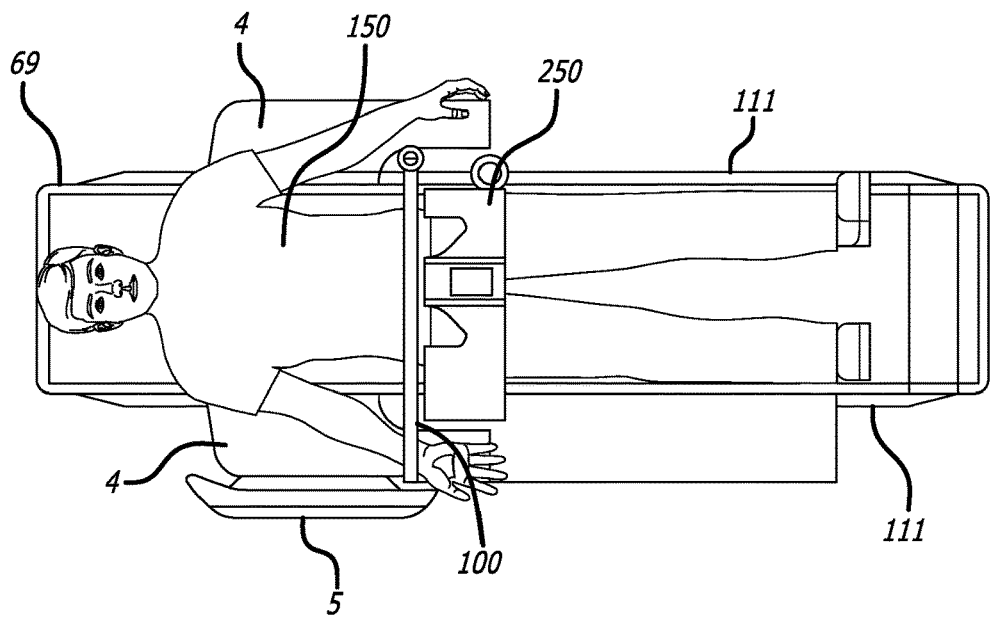
FIG. 27—Image of a rail configuration around the perimeter of the patient mattress.

FIG. 27 demonstrates one embodiment of the patient mattress 69 in which the integrated rails 111 extend the length of the mattress 69 along either side. The wing 5 is attached with the arm board 4 to the rail 111 on the right side of the patient 150. The waist radiation protection component is in the form of a flag 100 that is mounted to the rail 111 on the patient left side. A patient workbench 250 is also mounted to the rail 111 on the patient left side and resides across the waist and groin area of the patient 150.

Figure 28:
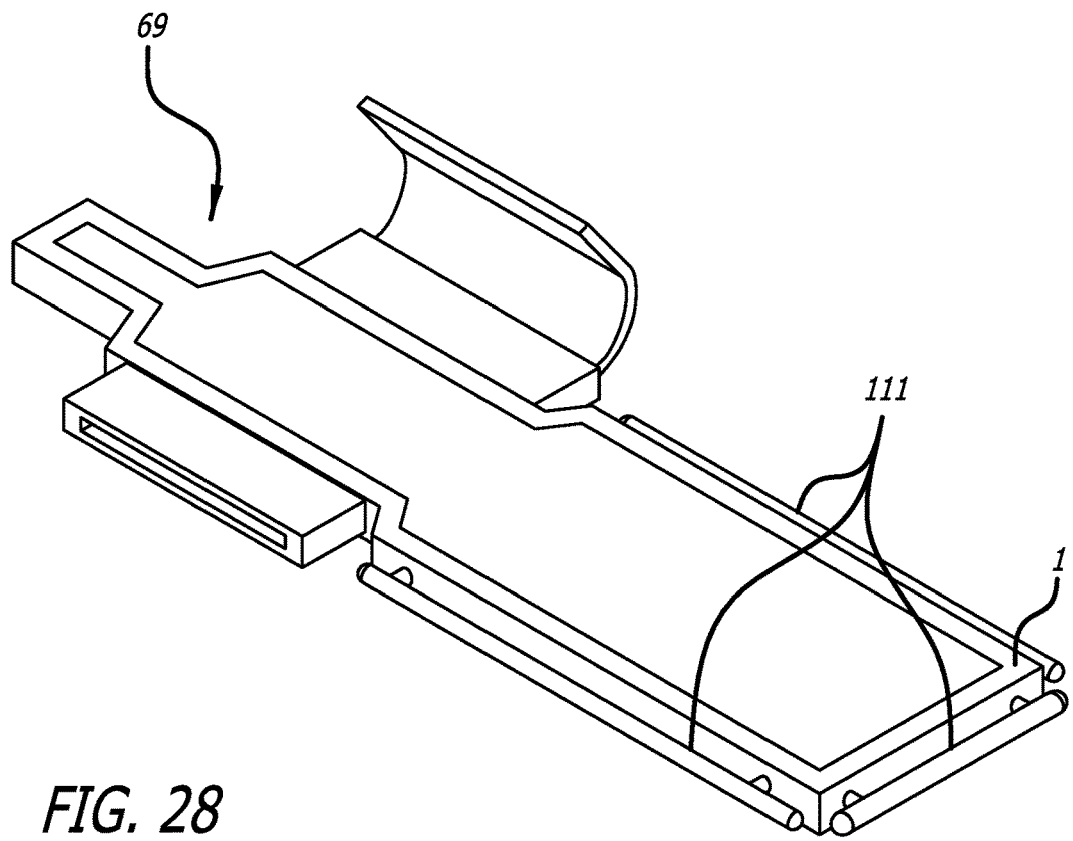
FIG. 28—Image of an alternate rail configuration around portions of the perimeter of the patient mattress.

FIG. 28 demonstrates an alternate embodiment of the patient mattress 69 in which integrated rails 111 are mounted to the sides and end of the outer shell 1.

Figure 29:
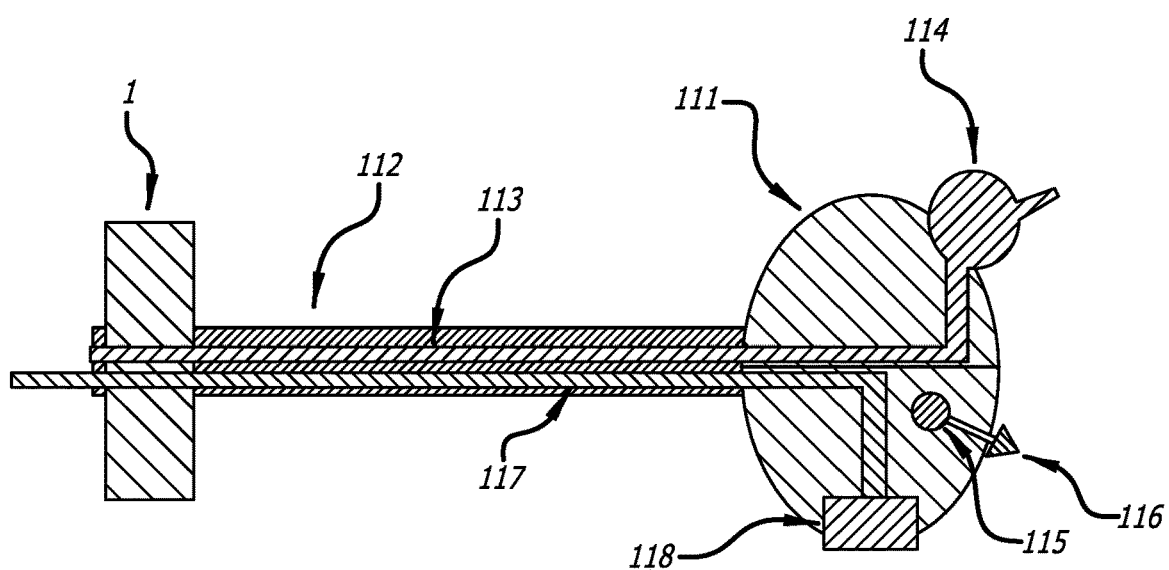
FIG. 29—Cross-sectional view of the rail, demonstrating lines carrying gas, data and power.

FIG. 29 shows a cross-sectional view of the rails 111 integrated with the outer shell 1 via a rigid connector 112. Within the rail 111 and the connector 112 resides a gas line 113 that terminates at a regulator 114 which can communicate with tubing to the patient. Also housed within the rail 111 and connector 112 is a power line 117 that comes from within the outer shell 1 and terminates in a power connection 118 that may be used to power devices for patient monitoring or care. The rail 111 also houses a data line 115 that terminates in a data connector 116 that can be used to transfer data to and from the patient.

Figure 30:
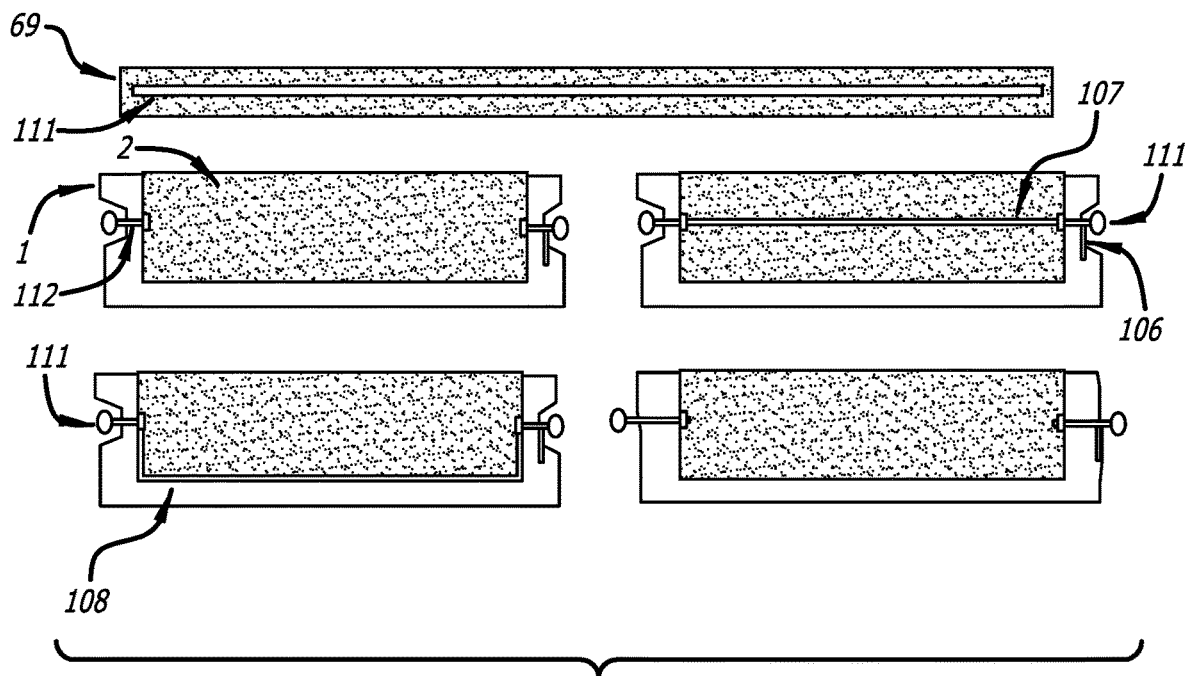
FIG. 30—Cross-sectional view of the mattress, demonstrating alternate rail configurations.

FIG. 30 describes methods in which the rail 111 may be mounted relative to the mattress 69. The rail 111 may be mounted to the outer shell 1 via rail supports 112 that affix to the outer shell 1, with the rail 111 recessed within the body of the outer shell 1. There may also be a lateral support 107 that traverses between rails 111 on either side of the outer shell 1. Alternately, the rail 111 may have a secondary support 106 to the outer shell 1, and may also have a rigid member 108 along the inner perimeter of the outer shell 1 that connects the two rails 111 together. Finally, as shown in this figure the rail 111 may or may not be recessed into the outer shell 1.

Figure 31:
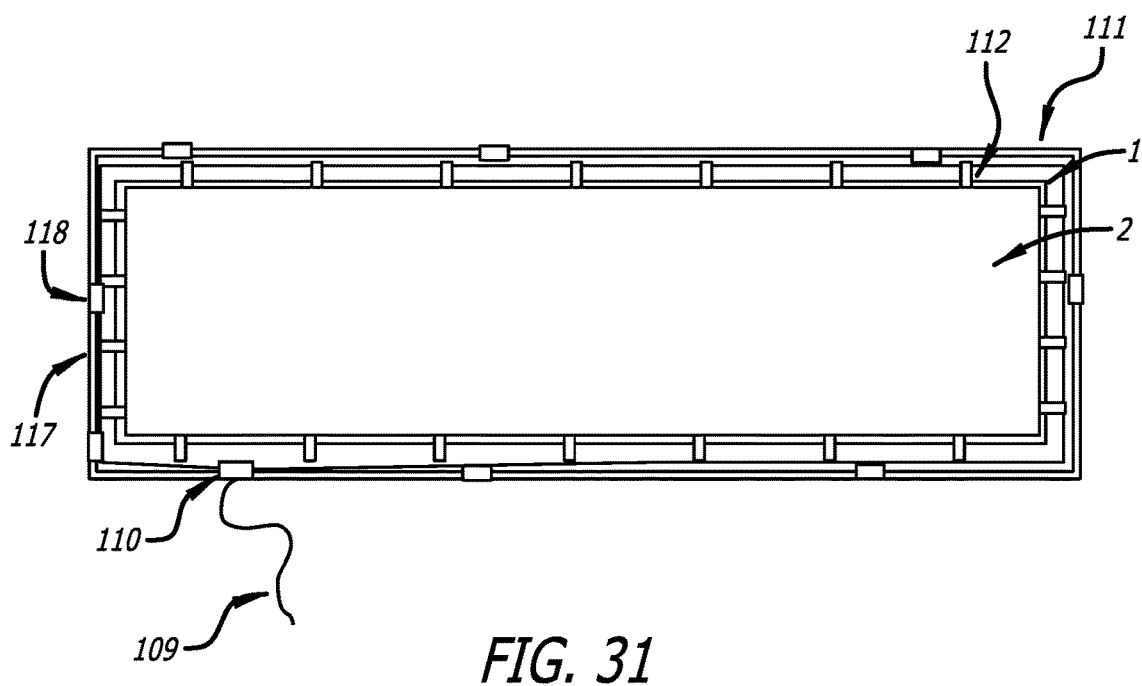
FIG. 31—Image showing a top view of the mattress with rails, showing power connections and isolation locations.

FIG. 31 details a power system that is integrated into the rail 111. The rail 111 is affixed to the outer shell 1 of the mattress system 69 by rail supports 112. Attached to the rail 111 is a power connection 109 to an outside source. Within the rail 111 is a power isolation and conditioner 110 that is used for voltage, polarity or transforming from alternating to direct current. A power line 117 runs through the rail system and power outlet connections 118 are placed in areas of need along the perimeter of the mattress 69 within the rail system 111.

Figure 32:
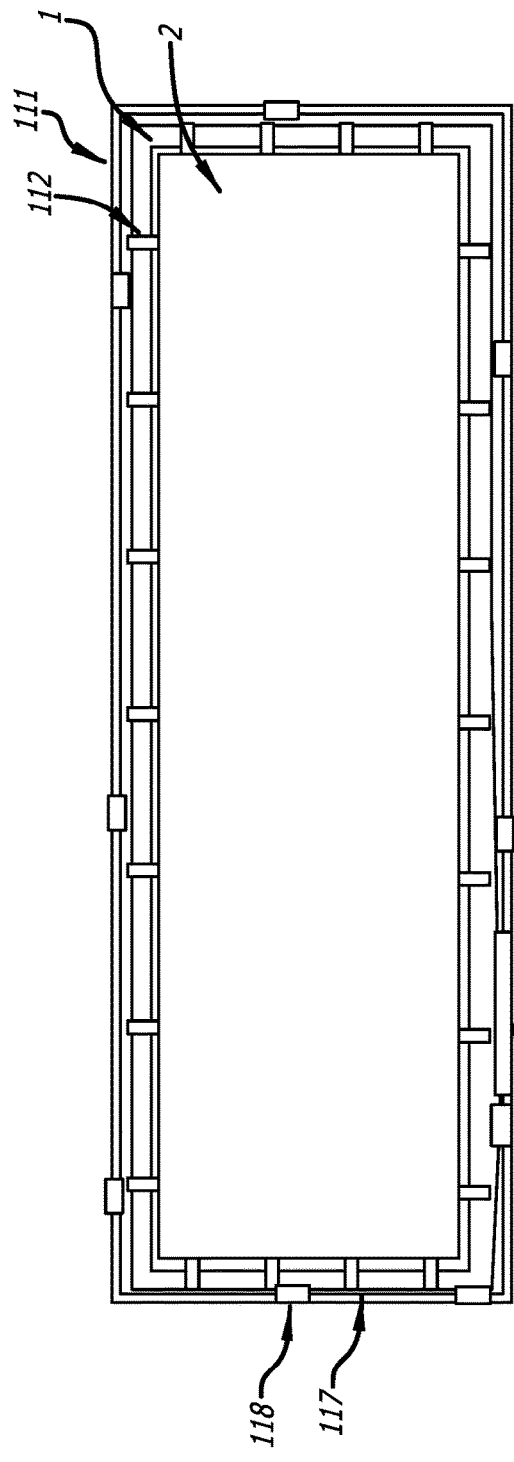
FIG. 32—Image showing a top view of the mattress with rails, showing a rechargeable battery within the rail.

FIG. 32 describes a power system similar to that of FIG. 31, with an internal power supply. A rechargeable/replaceable battery 136 is integrated into the rail in place of the external power connection 109, allowing the mattress system more portability.

Figure 33:
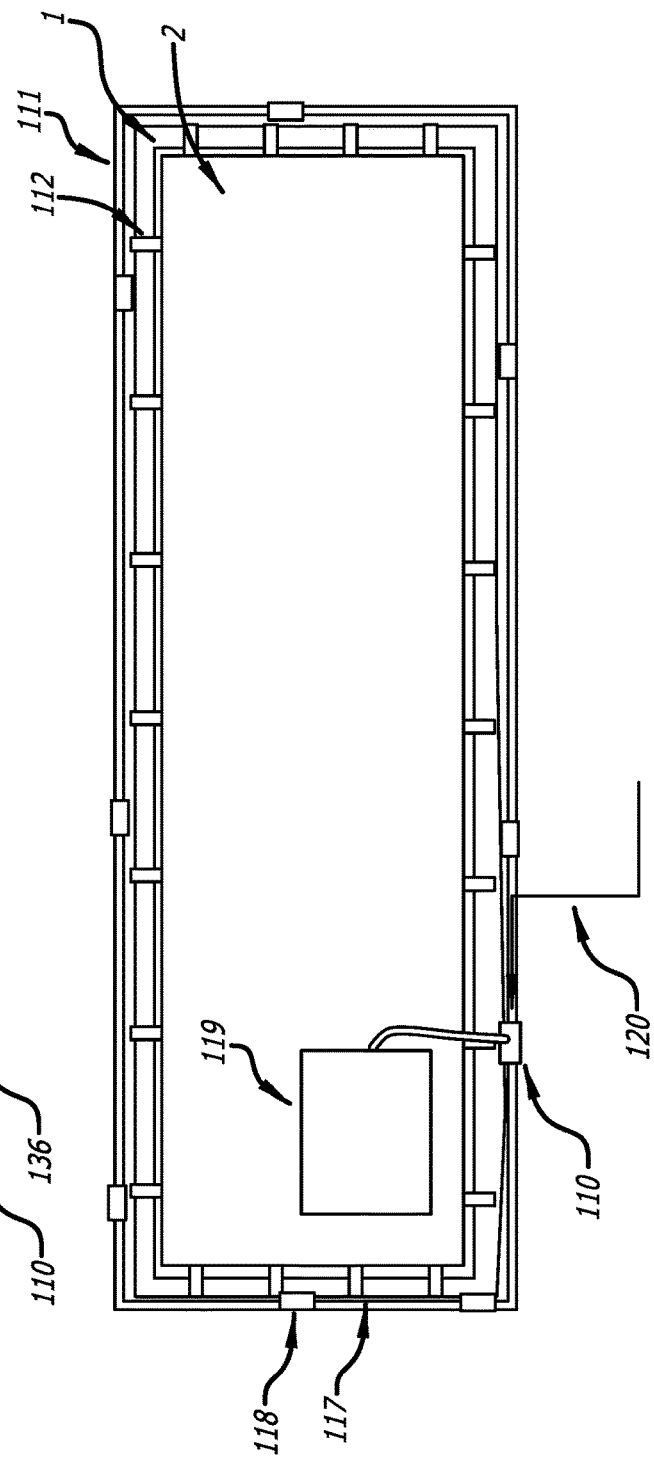
FIG. 33—Image showing a top view of the mattress with rails, showing a rechargeable battery within the mattress.

FIG. 33 describes a portable power system similar to that of FIG. 32, but with a battery 119 that is housed within the inner comfort component 2 of the mattress system 69. A detachable charging cable 120 can provide for the ability to recharge the battery 119 when necessary.

FIG. 34 describes how the rail system 111 can be used to transfer gas to the patient. Gas from an outside source is connected to the rail via the connector 121 and a gas regulator 122 is integrated into the rail 111. A gas line 123 runs through the rail 111 and gas output valves 124 are placed in areas of need along the perimeter of the mattress system 69.

FIG. 35 describes a gas system similar to that of FIG. 34, but with the gas supply housed within or attached to the rail 111 itself. A gas source 125 is mounted within or on the rail 111, with a gas regulator 122 used to manage gas pressure and flow.

FIG. 36 describes a gas system similar to that of FIG. 35, but with the gas source 125 housed within the inner comfort component 2 of the mattress system 69.

FIG. 37 describes how the rail system 111 may be used to carry data. A data connection 126 from an outside source is connected to the rail 111, and a data processing CPU (physiologic monitor, connection to hospital IT or a device controller) is housed within the rail. A data line 128 runs through the rail system 111, and data outlet connections 129 are placed in areas of need around the perimeter of the mattress system 69.

FIG. 38 describes a rail data and processing system with data isolation, multiple processors and a user interface integrated into the rail. Data is connected from an outside source 126, where an electrical isolation 130 and a data processing CPU 127 are mounted. Data is carried through the rail 111 via a data line 128, and data outlet connections 129 are mounted within the rail at locations where needed. A user interface 132 is mounted where accessible by the health care staff, and a second CPU 131 may also be integrated into the rail to provide additional computing power. In addition, devices may communicate with each other directly thought the rail data line. In addition, the user may control devices on the rail data system or send commands to elements connected to the data line 126 through user interface 132.

FIG. 39 describes a system similar to that of FIG. 38, with an alternate embodiment in which the CPU 134 is mounted within the patient comfort component of the mattress 2, and connected to the rail via a data line 135. The data communication to the outside in this embodiment is in the form of a wireless data transmitter and receiver 133.

Figure 40:
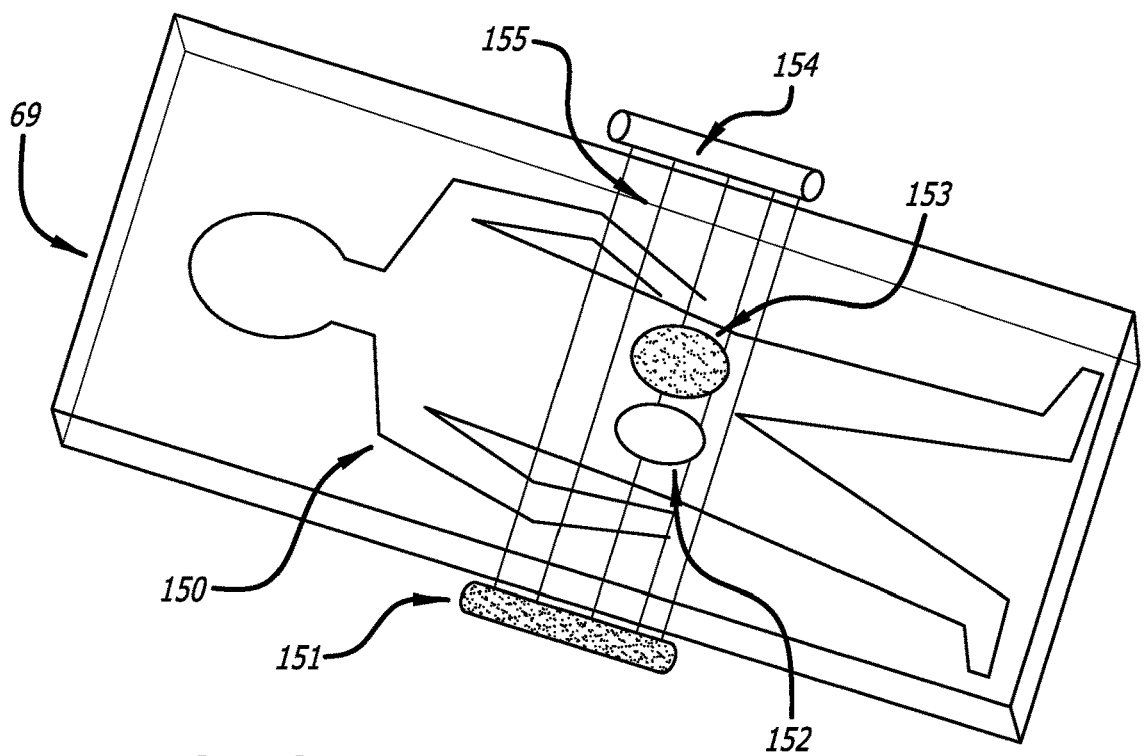
FIG. 40—Image of a patient lying atop the mattress with radiation protection rollers across the waist and groin. Removable cutouts are available for femoral access.

FIG. 40 shows a system of radiation protection integrated into the mattress system 69. A sheet of radiation protective material 155 is draped across a subject 150 lying on the mattress 69. This radiation protective material 155 is housed within a roller 154 when not in use. It is affixed across the table using a connector 151, which may be a hook or a magnetic attachment. Sites for femoral vessel access are placed in the radiation protective sheet 155 at the location of the left femoral 152 and the right femoral 153 arteries and veins. Access sites that are not used for a procedure may be closed off to prevent radiation backscatter from emitting through the access sites.

Figure 41:
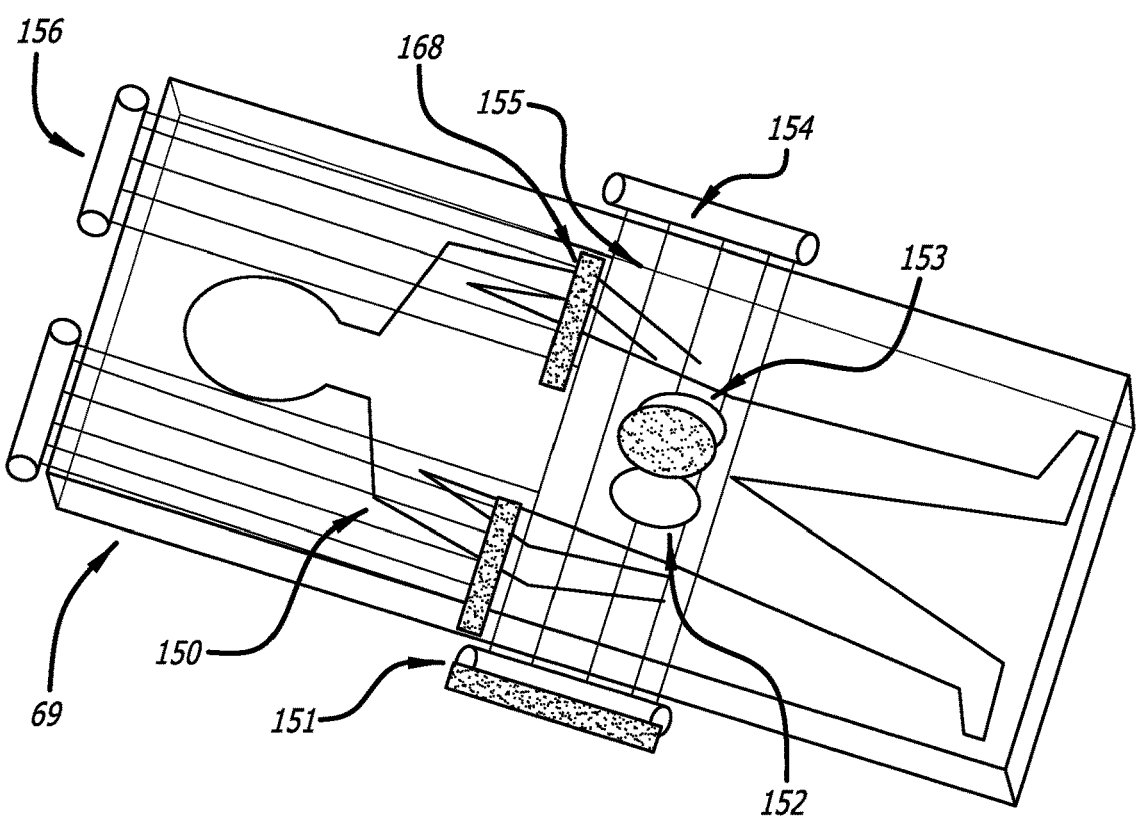
FIG. 41—Image of a patient lying atop the mattress with radiation protection rollers across the waist and groin. Additional rollers provide protection from radiation backscatter from the shoulders and arms.

FIG. 41 shows a system of radiation protection similar to that of FIG. 40, with additional radiation backscatter protection provided by roller sheets of radiation protection material 155 draped over the shoulders of the subject 150 from rollers 156 mounted at the head of the mattress system 69. These may be held in place by weighted pads or magnets 168 integrated into the end of the radiation protection material 155. In addition the shoulder radiation protection sheet may be attached to the femoral roller sheet 155 using hooks, clasps, zippers or magnets.

Figure 42:
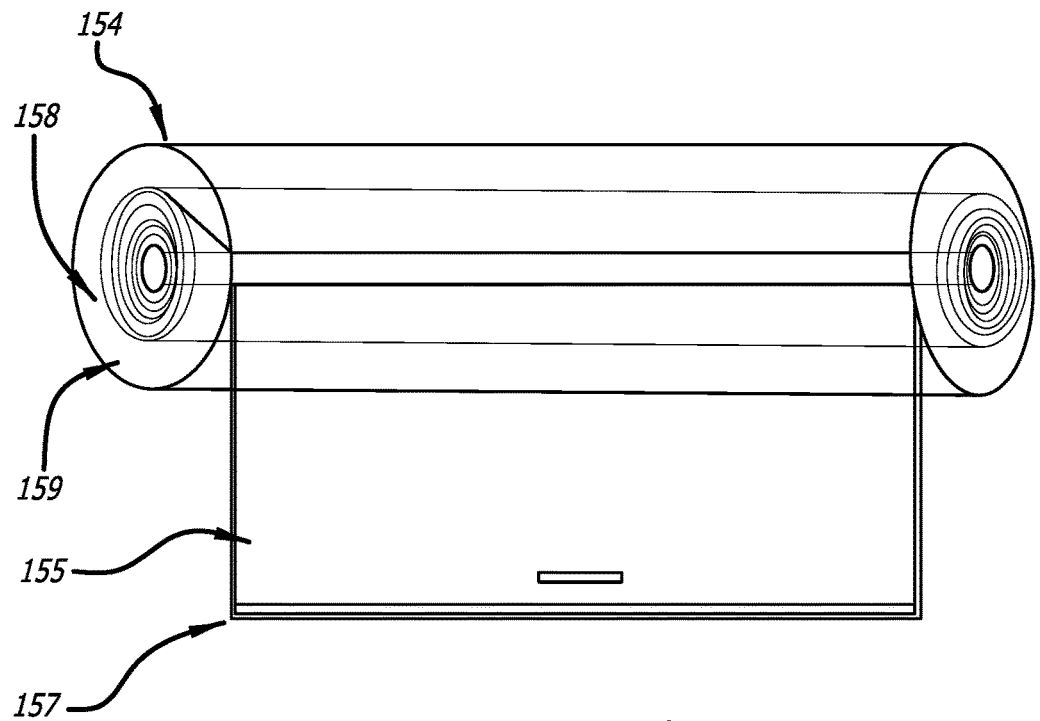
FIG. 42—Image of the roller mechanism and housing.

FIG. 42 shows one embodiment of the roller 154 in which the radiation protection material 155 is stored within a container of sterilization fluid 159 to prevent bacterial or viral contamination from being passed from patient to patient.

Figure 43:
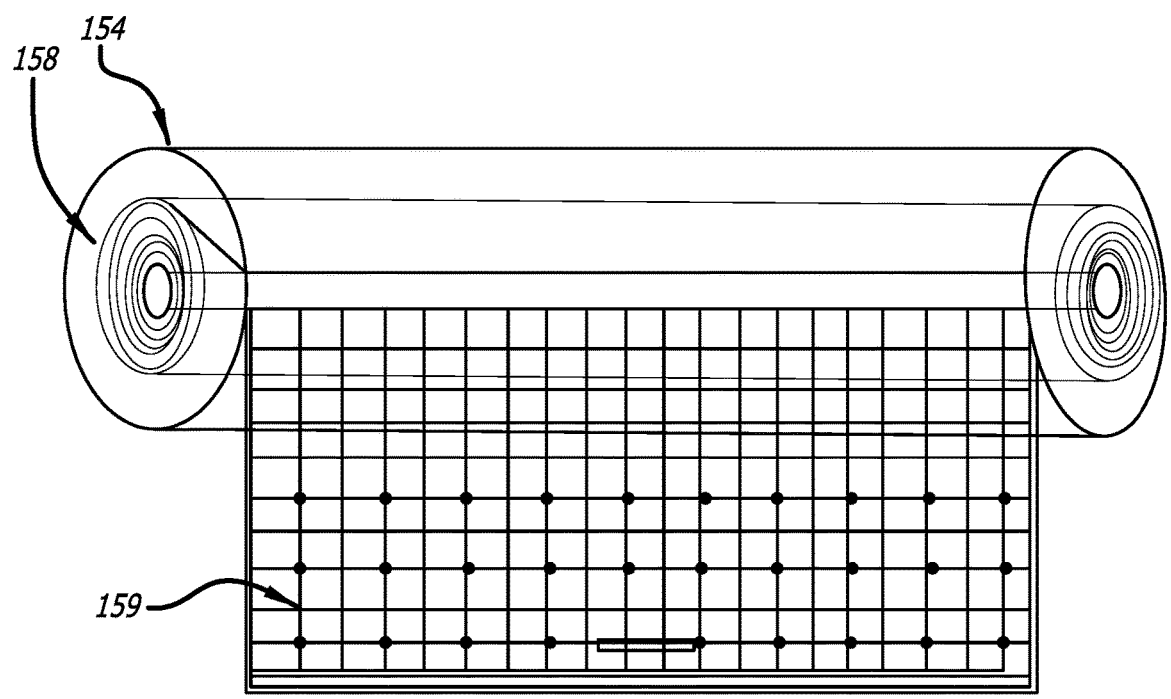
FIG. 43—Image of the roller mechanism and housing, with an integrated grid within the roller to provide for fluoroscopic landmarks.

FIG. 43 shows an embodiment of the roller 154 in which the radiation protective material 155 also contains a grid and dot marker matrix 159 on the sheets which are visible using fluoroscopy so that the grid may be used for reference location or measurement.

Figure 44:
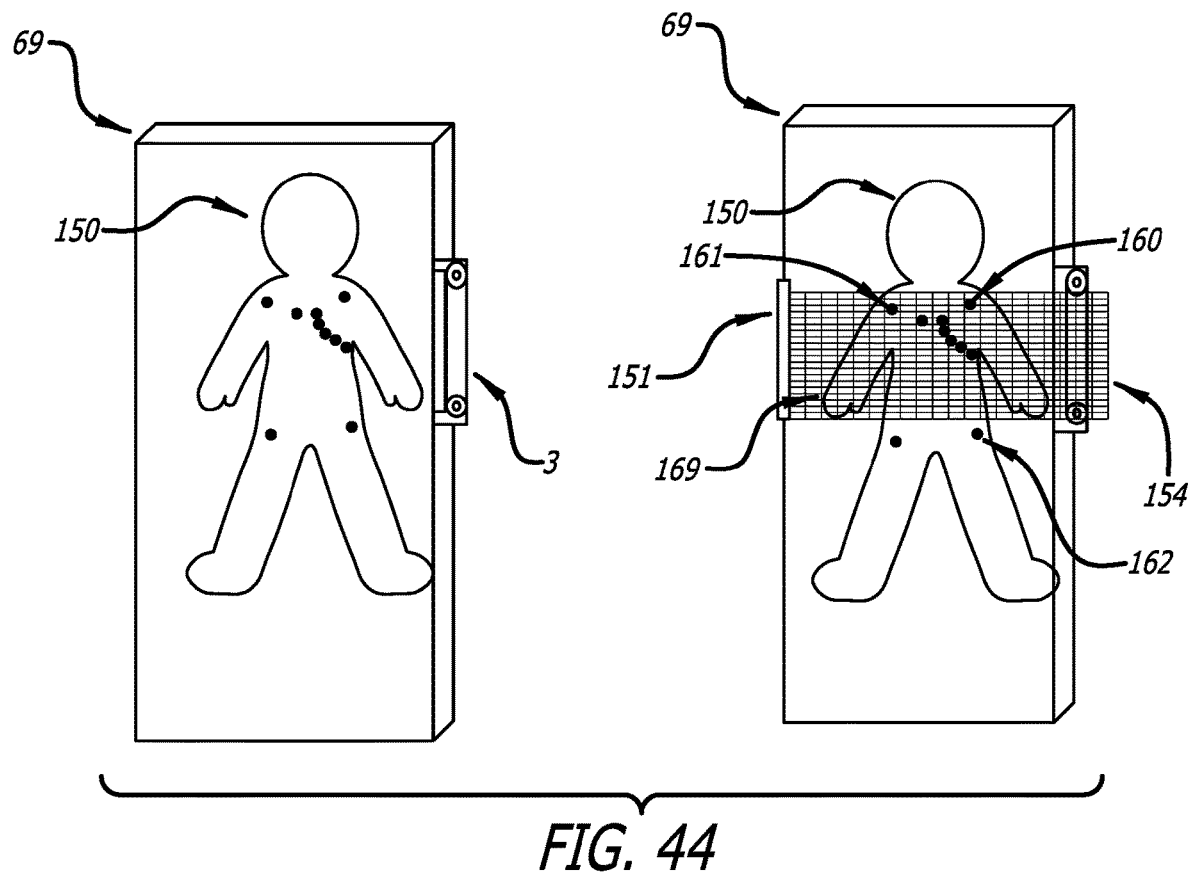
FIG. 44—Image of a roller mechanism used to provide contacts for a 12-lead ECG across the body of the patient.

FIG. 44 shows an embodiment of a roller system 154 in which the material on the roller is not radiation protective 155, but rather an electrically conductive film array 169. The subject on the mattress 150 has conductive patches 160 placed for an ECG in the areas of interest. As the roller material is draped across the subject on the mattress 150 and connected to the far side of the table 151, the conductive patches 160 come in contact with the conductive film array 169. The system senses which areas of the array are receiving an active signal and that data is sent to create the ECG. In another embodiment, the roller shield is both electrically conductive and provides radiation protection.

Figure 45:
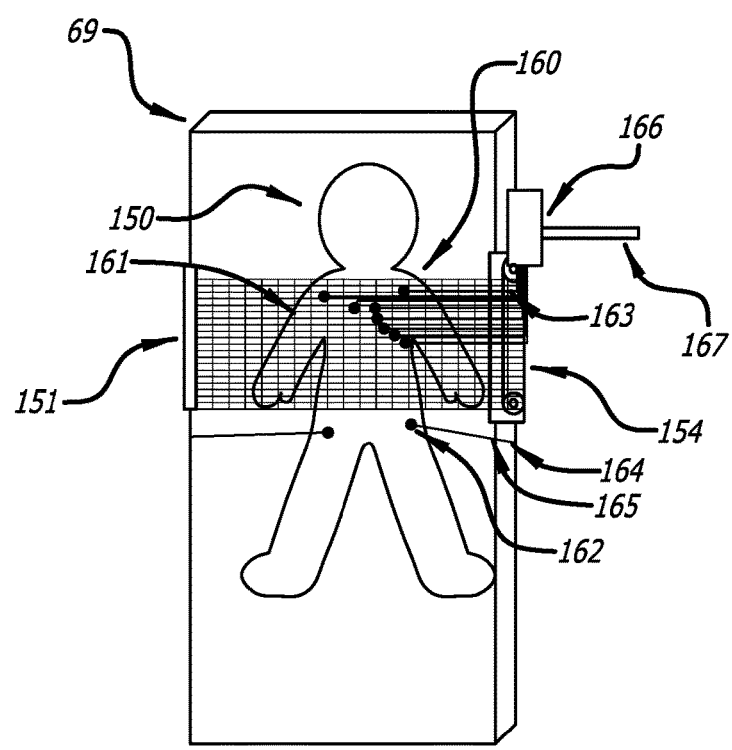
FIG. 45—Image of the roller mechanism with the 12-lead ECG in contact with the patient.

FIG. 45 provides an additional embodiment of the ECG construct. An ECG processing unit 166 is mounted to the mattress 69. The conductive film array 169 communicates with the processing unit 166. Conductive patches 162 that are not in contact with the conductive array film are connected with the processing unit 166 with traditional leads 165.

Figure 46:
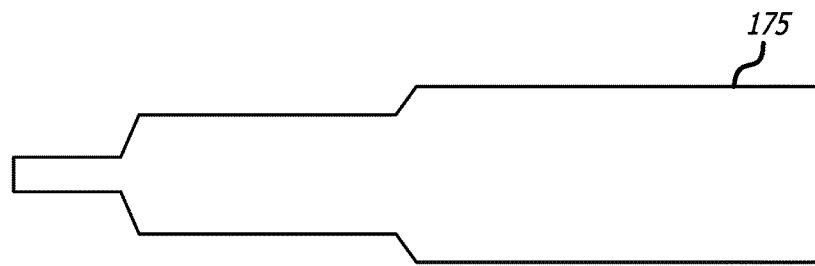
FIG. 46—First insulating layer of a flat wiring system.

FIG. 46 describes the first layer of a flat wiring system for use in a fluoroscopic field. This layer is an insulator 175, preventing electrical contact with adjacent materials. In one embodiment it is a polymeric film. It is shaped to fit the inner surfaces of the outer shell 1 of the mattress system.

Figure 47:
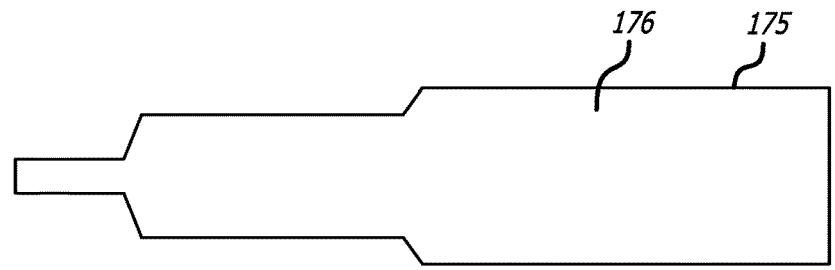
FIG. 47—Second layer of flat wiring system, consisting of film shielding to prevent electrical interference.

FIG. 47 describes the second layer of a flat wiring system. This layer is electrical shielding 176, in one embodiment being composed of aluminum film.

Figure 48:
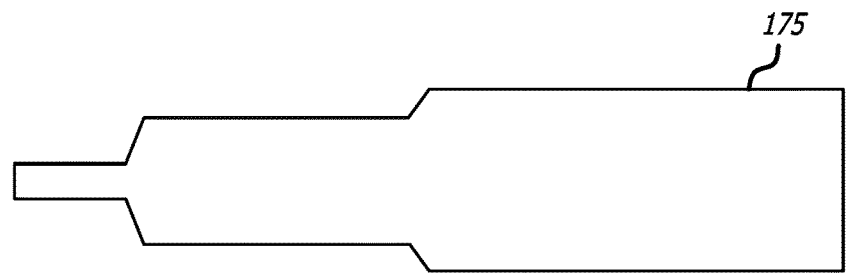
FIG. 48—Third layer of flat wiring system, consisting of a second insulating layer.

FIG. 48 describes the third layer of a flat wiring system. This layer is an insulator 175, preventing contact between the shielding and the conductors.

Figure 49:
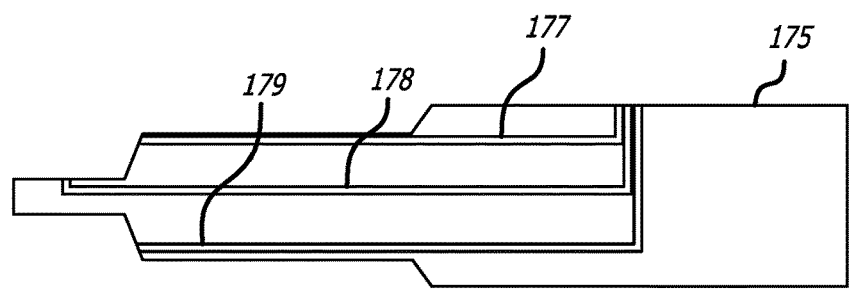
FIG. 49—Fourth layer of flat wiring system, consisting of flat ribbon wires from the point of ECG connection to the mattress to the point of monitor connection to the mattress.

FIG. 49 describes fourth layer of a flat wiring system, including the head side ECG leads. The left 177, center 178 and right 179 leads lay atop the insulator 175 and do not come into contact with each other.

Figure 50:
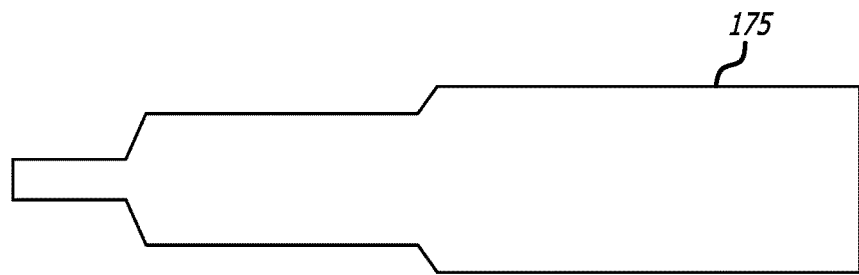
FIG. 50—Fifth layer of flat wiring system, consisting of a third insulating layer.

FIG. 50 describes the fifth layer of a flat wiring system. This layer is an insulator 175, preventing contact between the lead layers.

Figure 51:
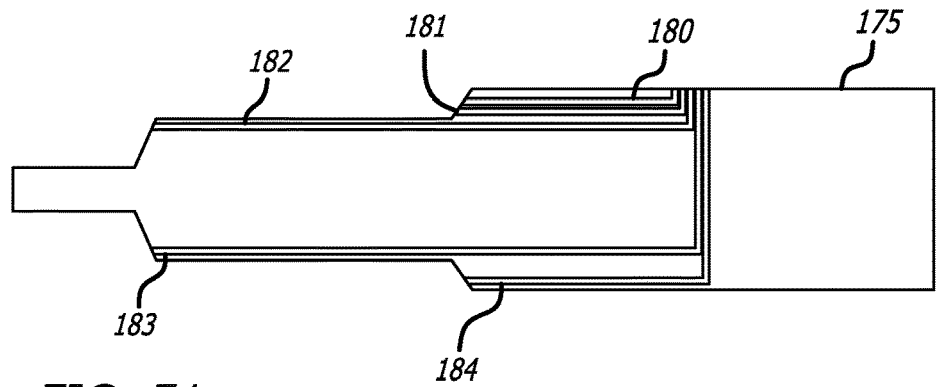
FIG. 51—Sixth layer of flat wiring system, consisting of additional flat ribbon wires from the point of ECG connection to the mattress to the point of monitor connection to the mattress.

FIG. 51 describes the sixth layer of a flat wiring system. This layer contains additional chest leads and arm/leg leads. These leads do not come into contact with each other and terminate at ECG locations within the mattress shell 1.

Figure 52:
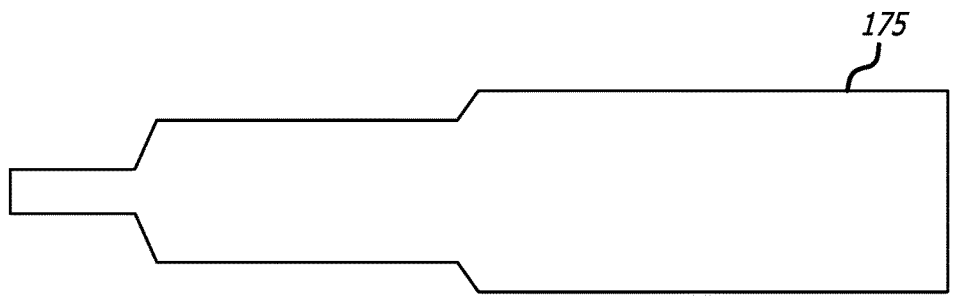
FIG. 52—Seventh layer of flat wiring system, consisting of a fourth insulating layer.

FIG. 52 describes the seventh layer of a flat wiring system. This layer is an insulator 175, preventing contact between the conductors and shielding.

Figure 53:
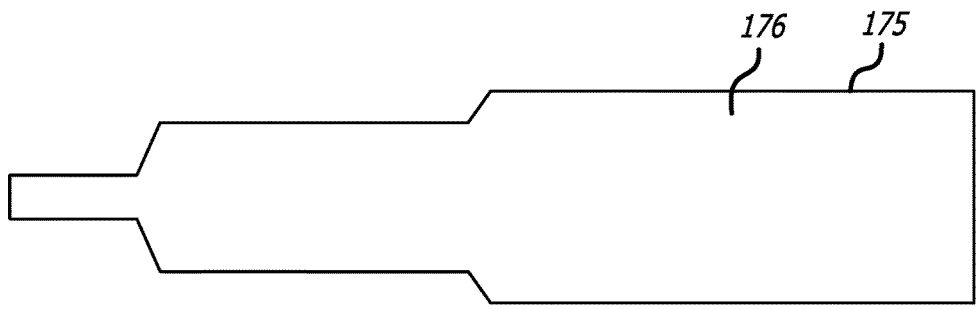
FIG. 53—Eighth layer of flat wiring system, consisting of a second layer of film shielding to prevent electrical interference.

FIG. 53 describes the eighth layer of a flat wiring system. This layer is electrical shielding 176, in one embodiment being composed of aluminum film.

Figure 54:
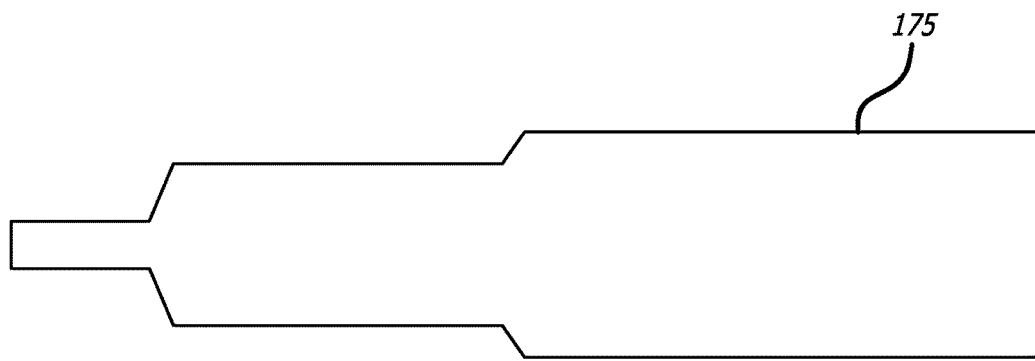
FIG. 54—Ninth layer of flat wiring system, consisting of a final insulating layer.

FIG. 54 describes the ninth layer of a flat wiring system. This layer is an insulator 175, preventing contact between the shielding and adjacent materials.

Figure 55:
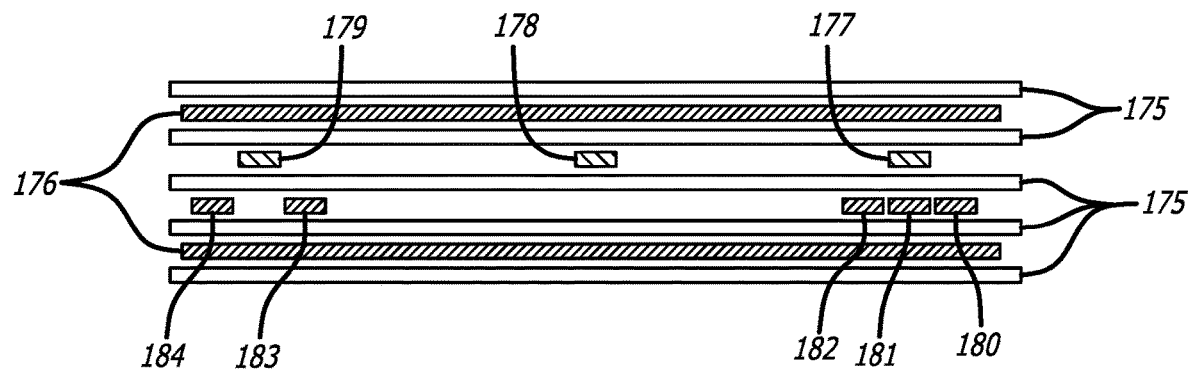
FIG. 55—Cross-sectional view of the wiring assembly, demonstrating the relative position of the layered components.

FIG. 55 is a cross-sectional end view of the flat wiring system, showing the relative positions of the insulation 175, shielding 176 and ECG leads 177-184.

Figure 56:
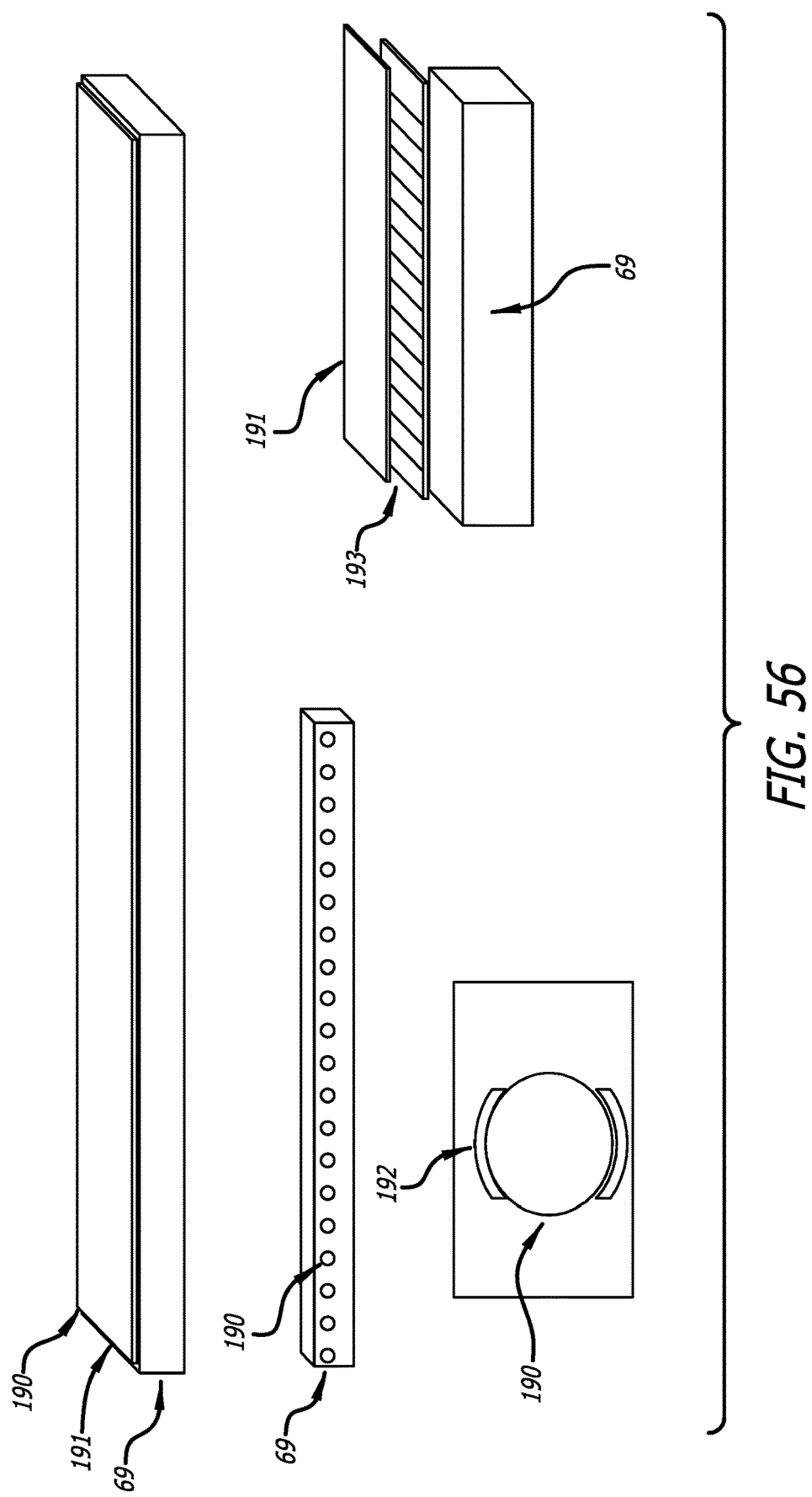
FIG. 56—Image showing the configuration and components of an integrated ultraviolet C system for mattress disinfection.

FIG. 56 describes a system for integrating UV C sterilization into the patient mattress system 69. In one embodiment, optical fibers 190 are interwoven or embedded into the mattress surface with a removable light shield 191 used as one means to protect the health care workers from UV exposure. In another embodiment, the optical fibers are cladded with a shielding material 192, which is partially removed from the fiber in order to provide directional shielding from the UV rays.

Figure 57:
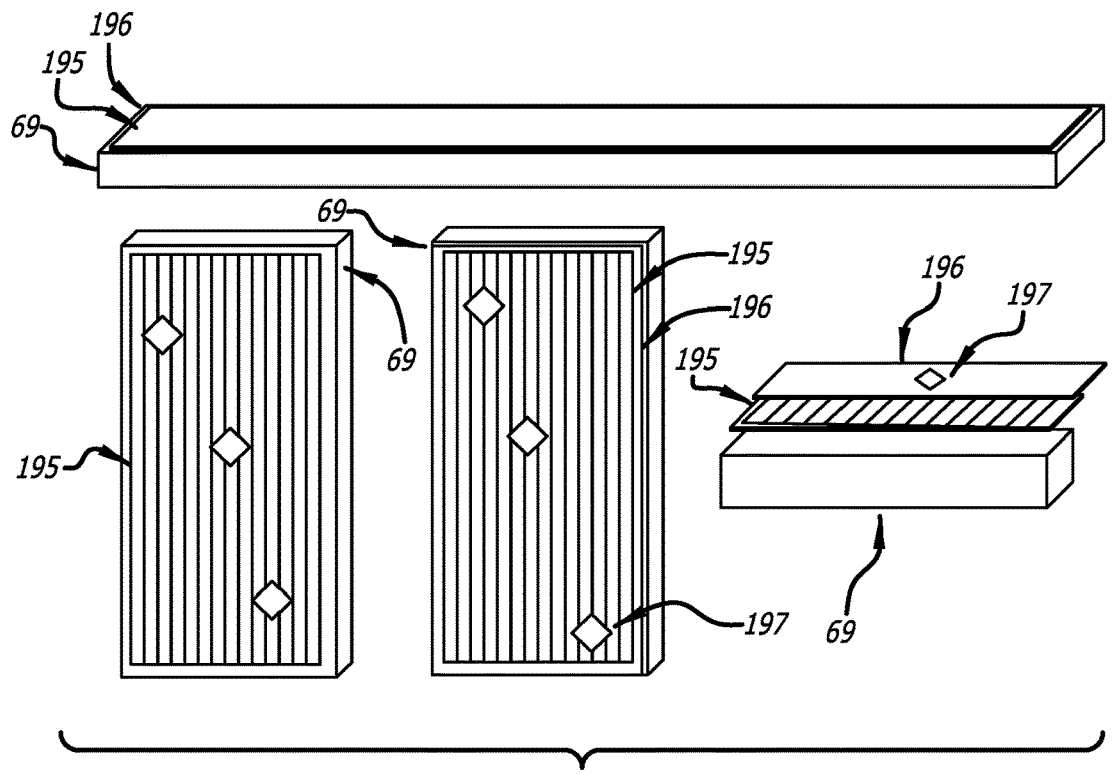
FIG. 57—Image showing the configuration and components of an integrated heating system for mattress disinfection.

FIG. 57 describes a system for integrating heat sterilization into the patient mattress system 69. Heating elements 195 are integrated into the surface of the mattress and a heat conductor 196 diffuses the heat throughout the mattress surface. Heat sensors 197 are used to ensure that the heat is sufficient for sterilization, and provide a safety mechanism to prevent activation of the heating system if a patient is on the mattress system 69.

Figure 58:
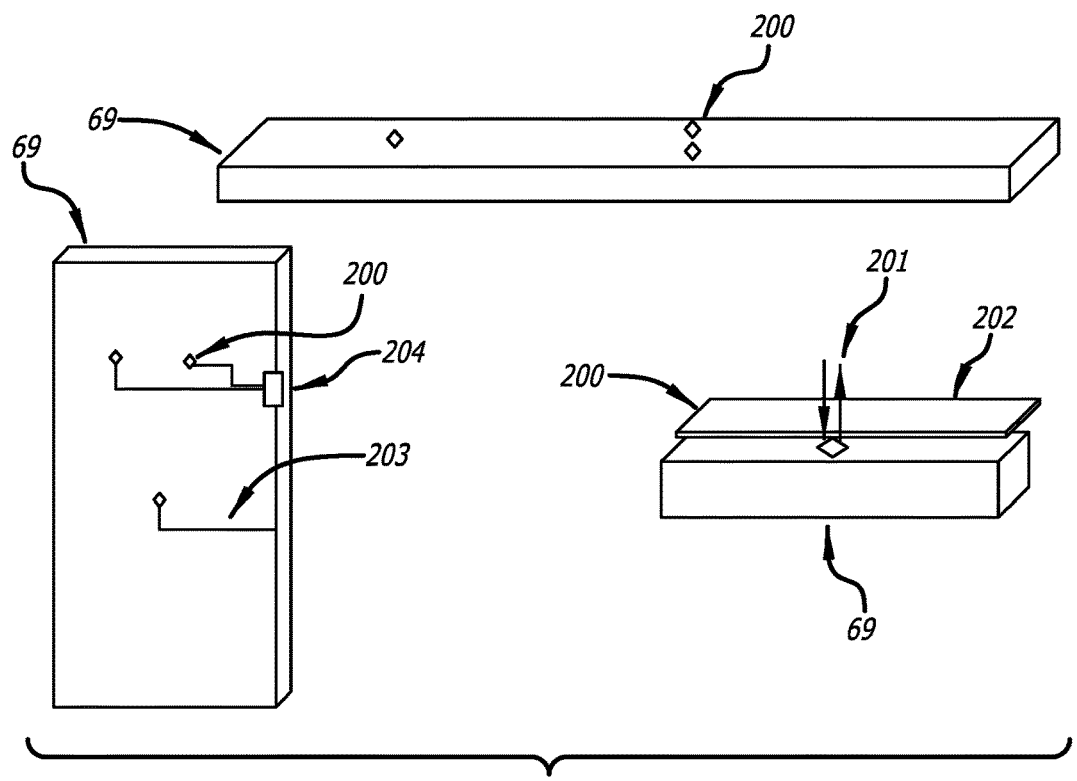
FIG. 58—Image demonstrating integrated pulse oximetry into the mattress.

FIG. 58 describes a system for integrating pulse oximetry into the patient mattress system 69. Pulse oximetry emitter-detectors 200 are placed within the mattress and the mattress system 69 is draped with a clear drape 202. Light 201 is emitted by the emitter-detectors 200 through the clear drape 202 to the skin of the patient and the response picked up by the emitter-detector 200 is used to determine blood oxygen content. In an alternate embodiment, the emitter-detectors 200 emit coherent light where changes in reflected light frequency are used to detect tissue blood flow.

Figure 59:
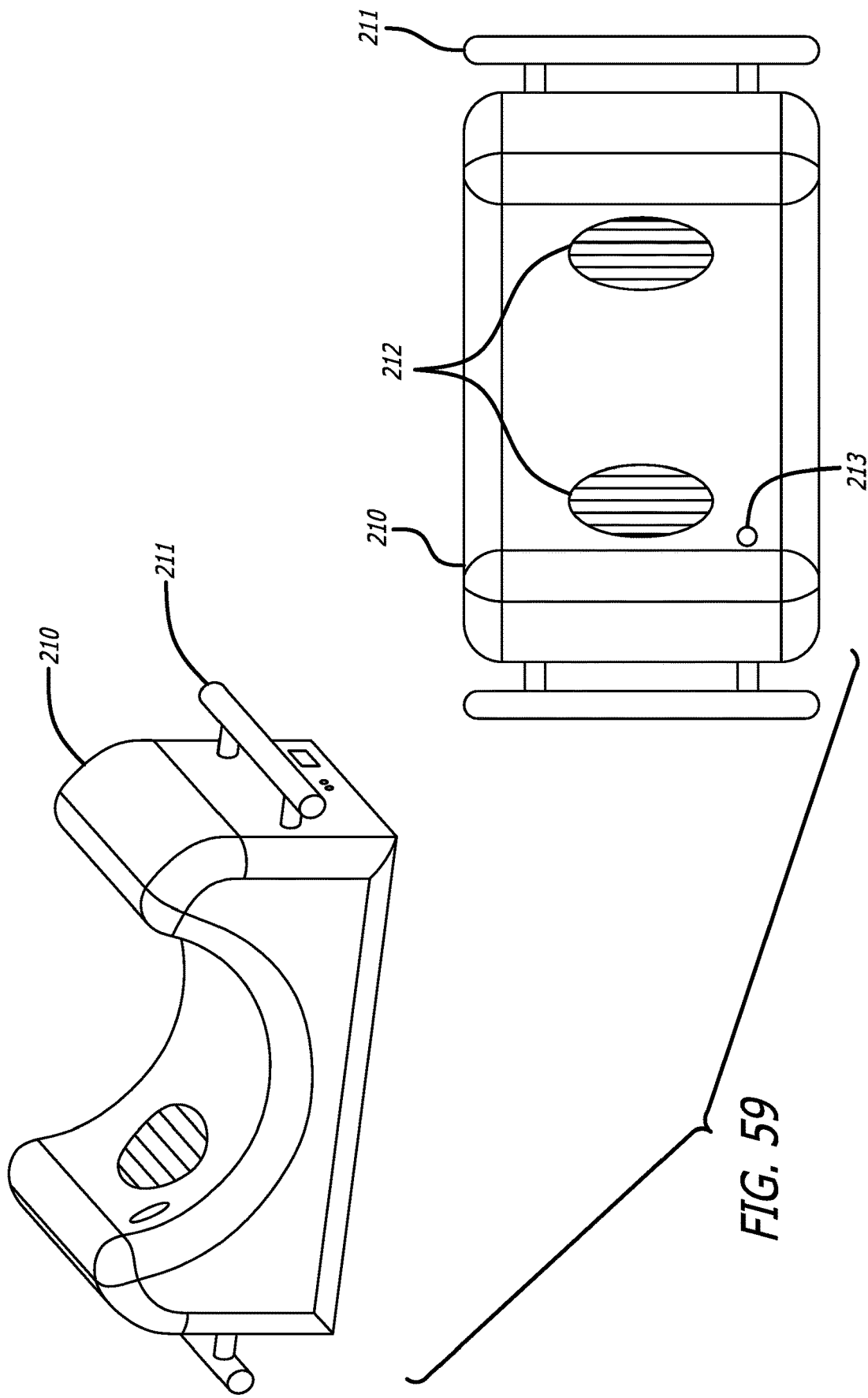
FIG. 59—Image showing the head nest system for the mattress, containing speakers and rails.

FIG. 59 describes a head component 210 to be used with the mattress system 69. This is intended as a type of pillow, with additional functionality for the health care environment. In one embodiment, this head component 210 contains speakers 212 and a microphone 213 for communication between the patient and the health care staff. The head component 210 also has rails 211 affixed to it, to allow for mounting of equipment (EEG, camera, pulse oximetry) near the head of the patient.

Figure 60:
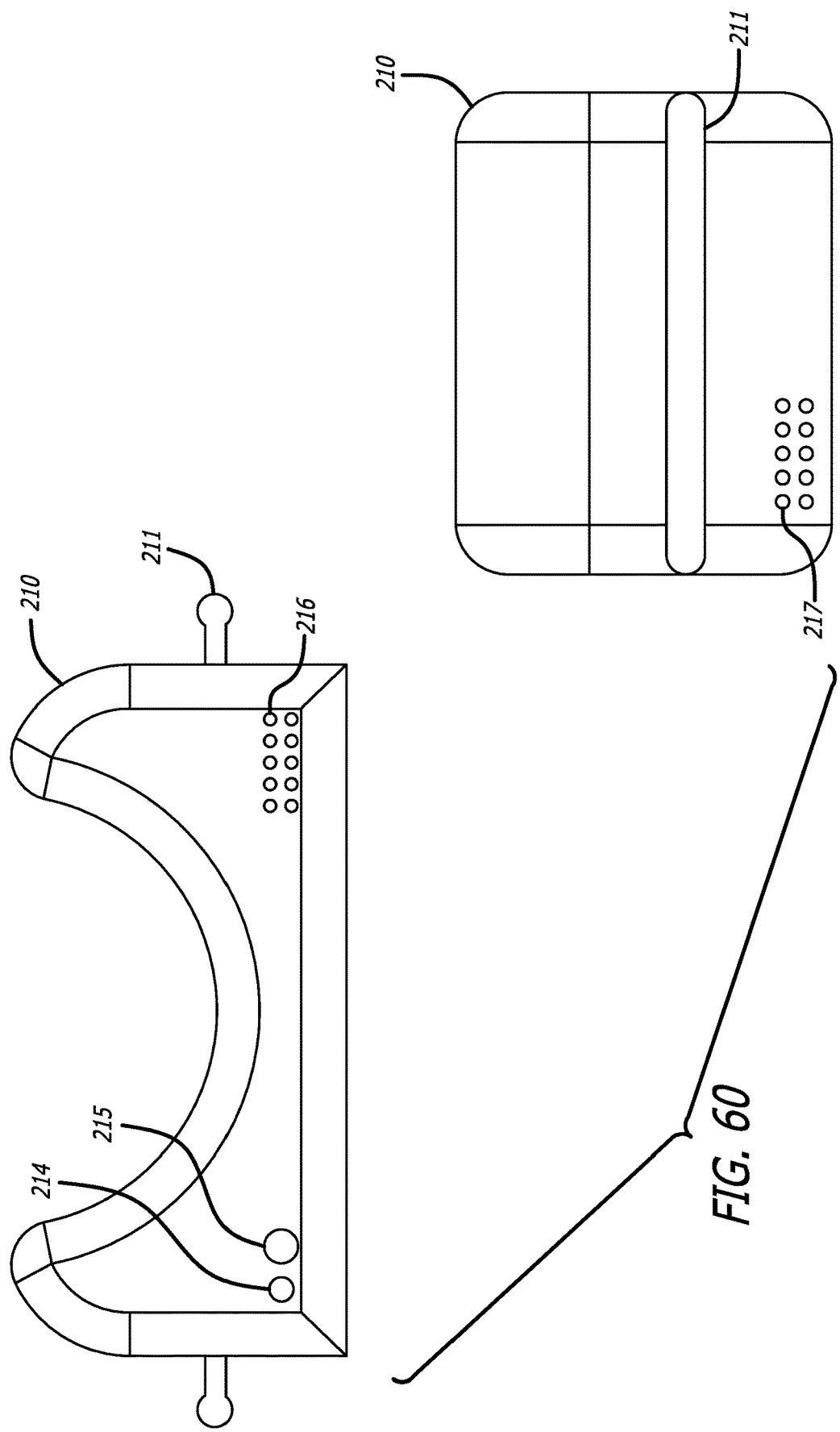
FIG. 60—Image showing pulse oximetry and EEG connections in the head nest system.

FIG. 60 describes further features of the head component 210. There are EEG lead connection sites for input 216 and output 217, as well as pulse oximetry input 214 and output 215 locations.

Figure 61:
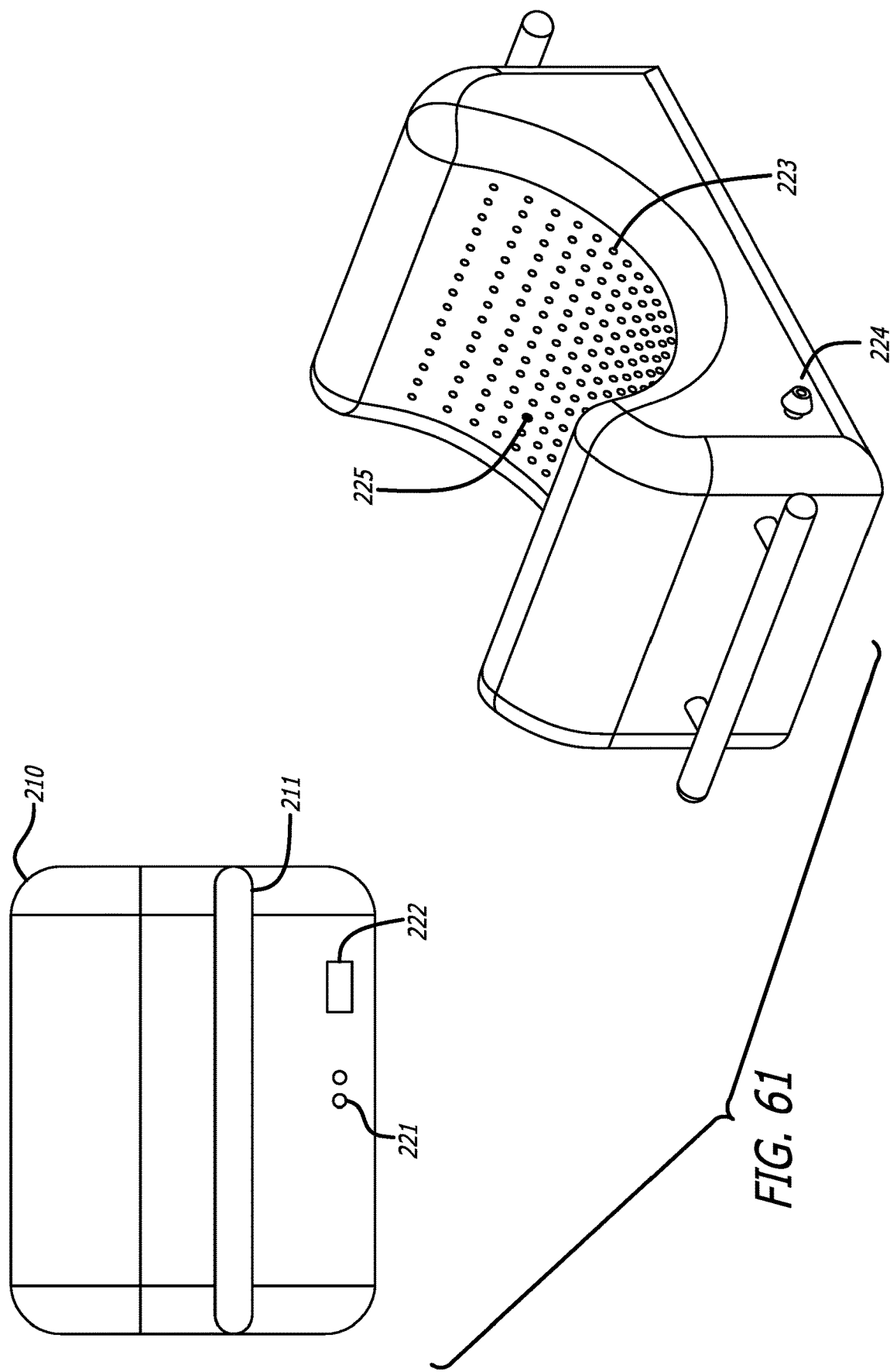
FIG. 61—Image showing audio, power and gas connections to the head nest, as well as venting pattern for head cooling.

FIG. 61 describes a further embodiment of the head component 210. There are locations for audio in and out 221 as well as a power supply 222. Additionally, the head component 210 may be used for hypothermic head cooling, in which gas can be connected to the head component 210 via a gas connector 224, and cooling gas may be driven through vent holes 223 to cool the scalp. Temperature sensors 225 on the head component may be used to automatically drive gas flow until the scalp reaches a preferred temperature.

Figure 62:
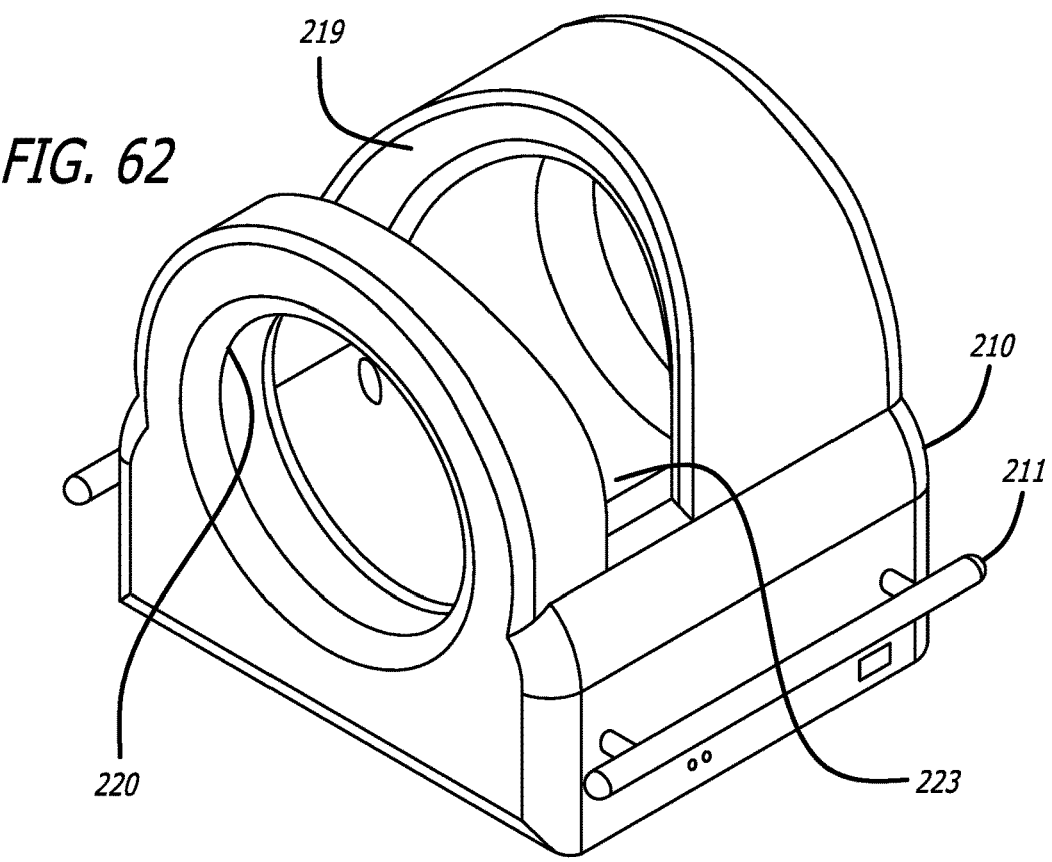
FIG. 62—Image showing full head capture for direct EEG contact and more venting exposure for head cooling.

Alternately, as shown in FIG. 62 the head component 210 may fully encapsulate the head, using a scalp component 219 that can provide direct EEG contact, as well as a modular neck component 220 that can restrain the head. This fully encapsulated system can provide more surface for the cooling vents 223 as well.

Figure 63:
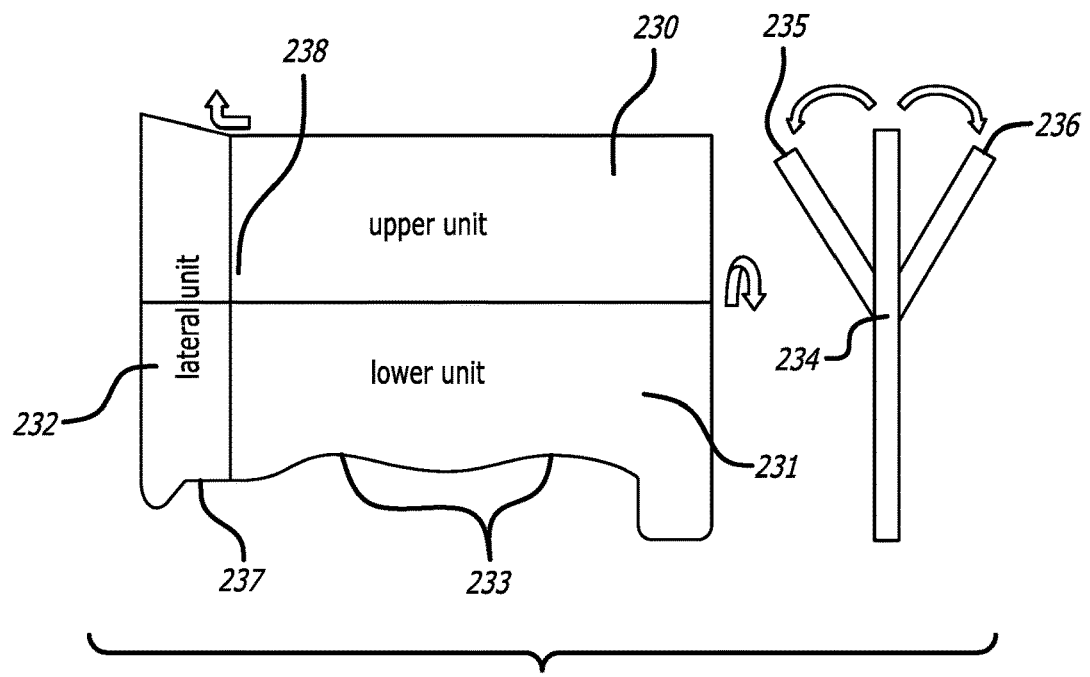
FIG. 63—Image showing flag radiation protection system with regions of deflection.

FIG. 63 describes a radiation protection flag designed to reside over the patient, positioned across the width of the table. The lower unit 231 is relatively rigid, with a cutout for the patient anatomy 233, in this case the groin for femoral vascular access. The upper unit 230 is attached to the lower unit 231 by a hinge mechanism 234 that allows the top of the upper unit 230 to flex or rotate towards the head 236 or towards the feet 235 of the patient relative to the lower unit 231. A lateral unit 232 that may be made as a solitary component or with upper and lower units is attached to the rest of the flag by a vertical hinge 238 that allows for rotation of the outer edge towards the head or feet of the patient. A cutout 237 in the bottom of the lateral unit 232 accommodates the arm of the patient for radial vascular access.

Figure 64:
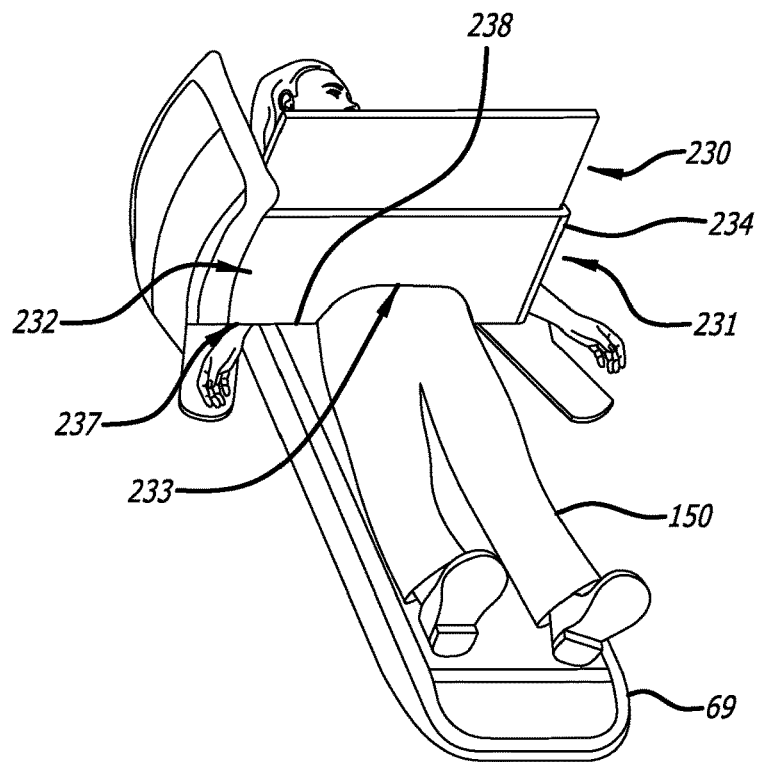
FIG. 64—Image showing flag radiation protection system integrated into the mattress system.

FIG. 64 shows the radiation protection flag in position on the patient mattress 69. The lateral unit 232 sits over the right arm of the patient 150, with the cutout 233 residing over the patient waist or groin. The vertical hinge 238 allows for flexion of the lateral unit 232 to better wrap around the patient 150 and to provide more complete radiation protection.

Figure 65:
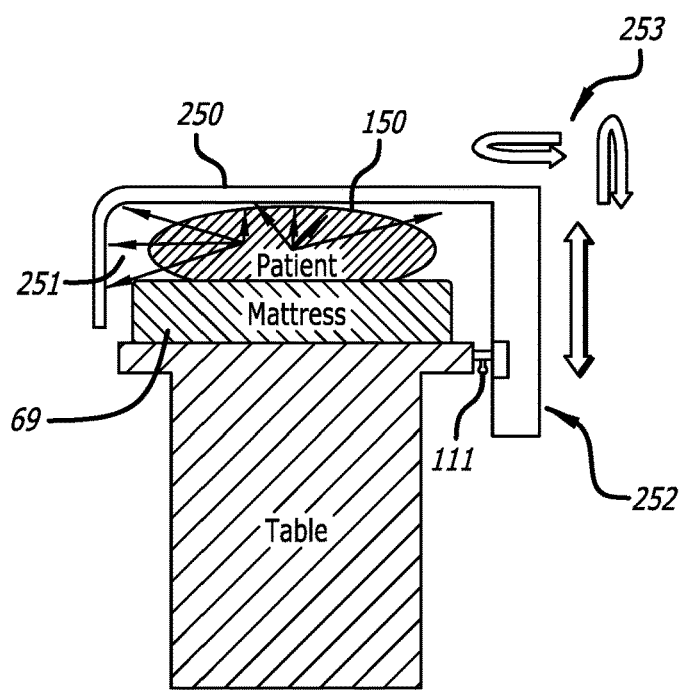
FIG. 65—Image showing workbench in relation to the mattress, patient and backscattered radiation.

FIG. 65 shows a perspective end view of the workbench 250 over the patient 150 on the mattress 69. The workbench 250 is radiation protective to prevent x-ray photons 251 from backscattering from the patient out to the health care staff. The workbench is mounted to the rail 111 using a vertical connection mechanism 252 by which the device may be reversibly affixed. The workbench is designed to provide multiple degrees of freedom in order to allow adjustments for height, rotation and tilt.

Figure 66:
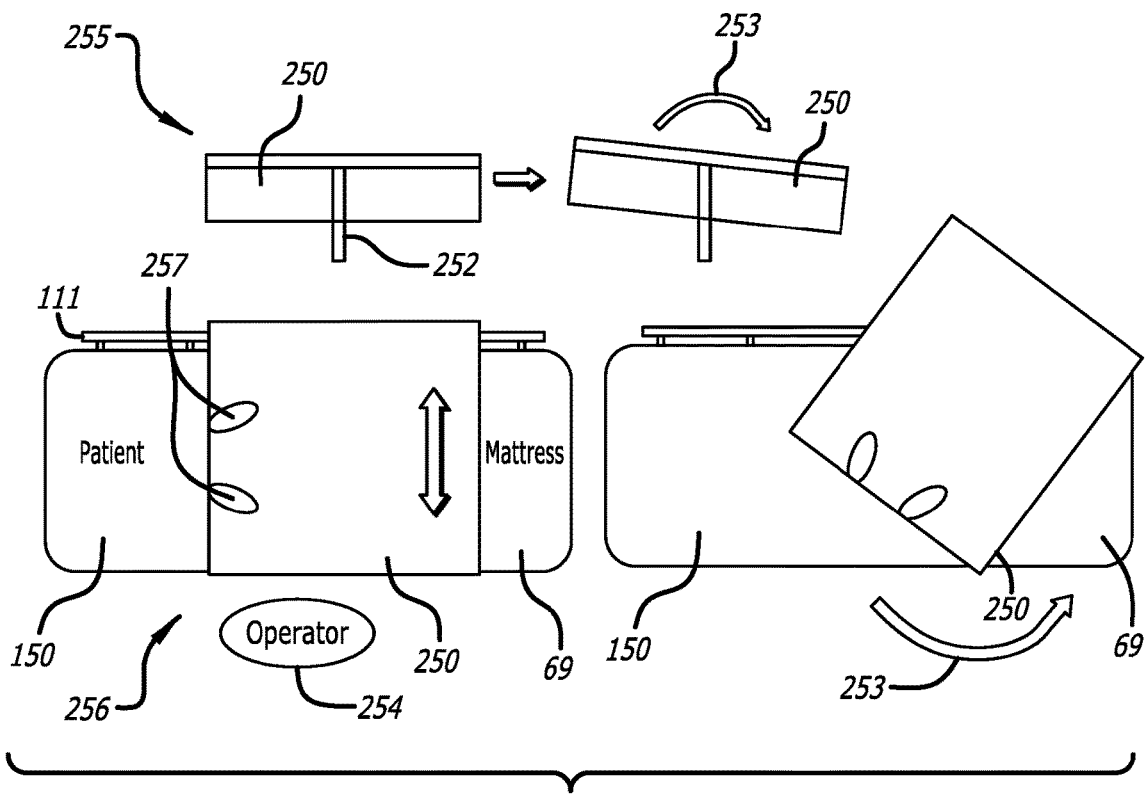
FIG. 66—Image showing workbench in relation to the mattress, demonstrating rotation and tilt features.

FIG. 66 shows top 256 and side 255 views of the workbench. In the side view 255, the workbench 250 can be rotated 253 about the vertical post 252. In the top view 256, cutouts 257 in the workbench 250 for femoral vessel access are shown. This workbench 250 is connected to the rails 111 in such a way that the workbench 250 may be rotated 253 over the patient 150 away from the operator 254 in order to gain access to the patient 150 or to facilitate patient transfer to or from the mattress 69.

Figure 67:
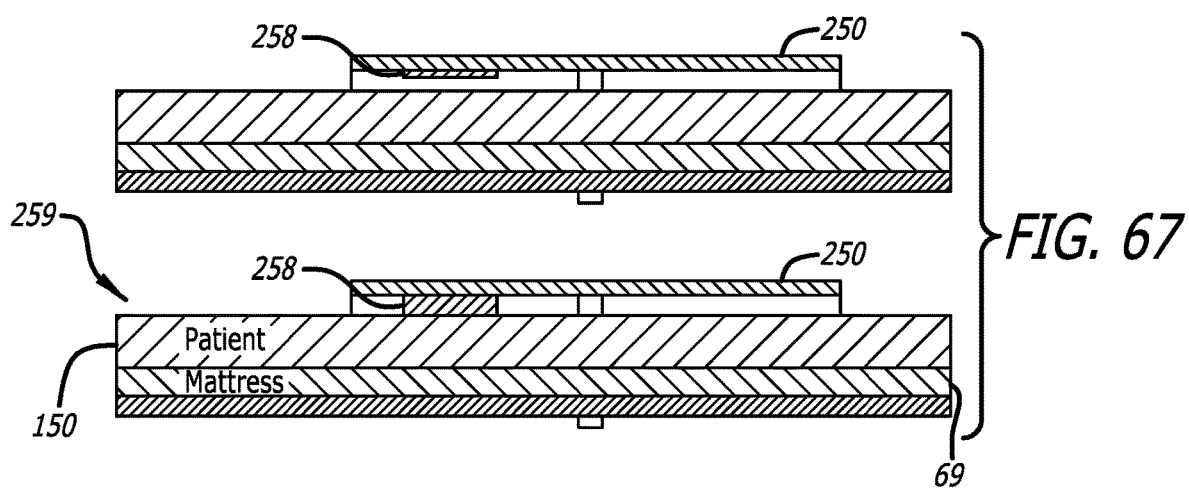
FIG. 67—Image showing features of the workbench to accommodate patient anatomy and aid in compression of vascular access sites.

FIG. 67 demonstrates side views 259 of the workbench 250 with a compression feature 258 to apply pressure to the patient (for example, to stop bleeding). When deflated, the compression feature 258 does not come into contact with the patient 150. When inflated, the compression feature 258 comes into contact with the patient, with the workbench 250 supporting the compression feature 258 such that active compression is placed on the leg of the patient. This compression may be used to prevent blood loss through a vascular access site after removal of catheters.

Figure 68:
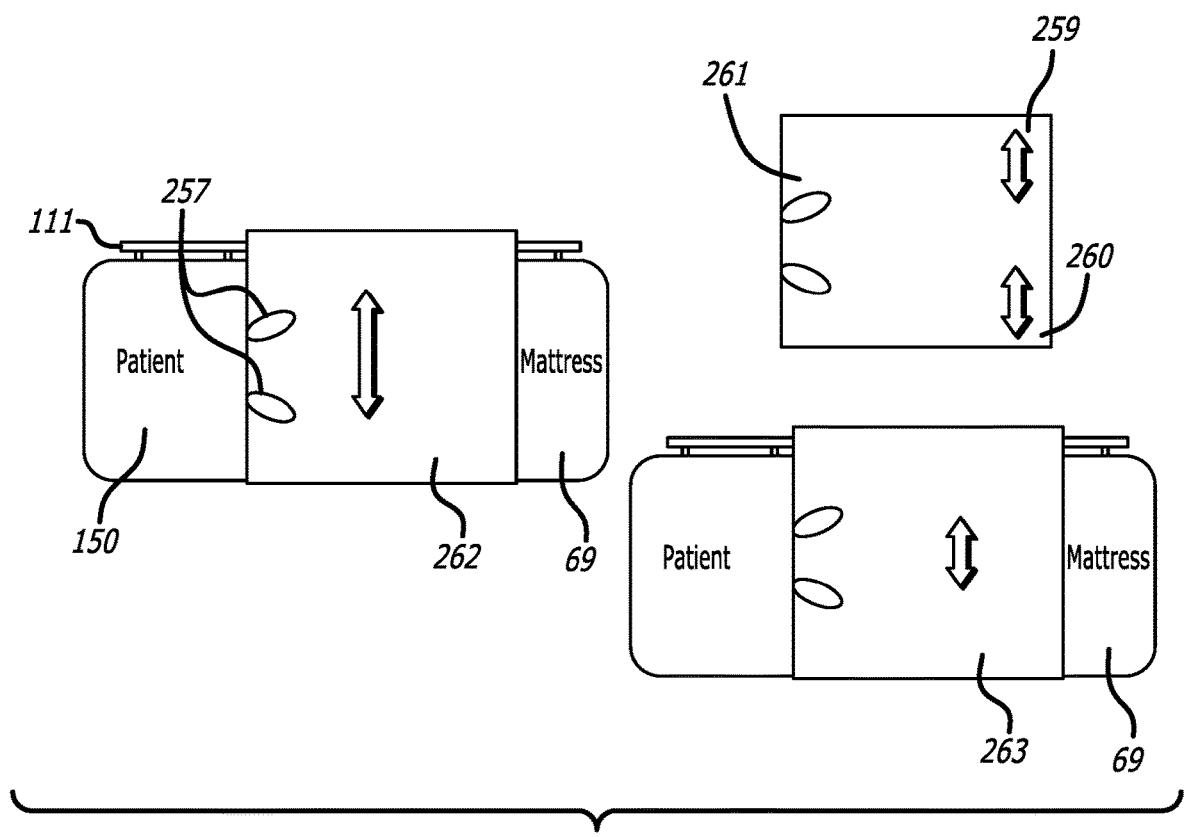
FIG. 68—Image showing workbench with adjustability of width to accommodate a range of vascular access sites.

FIG. 68 demonstrates a feature in which the workbench 250 may be expanded in size to change the relative positions of the femoral access cutouts 257 for various sized patients. In one embodiment, lateral workbench components 259 and 260 may be extended or retracted relative to a center component 261 in order to create a wide configuration 262 or a narrow configuration 263.

Figure 69:
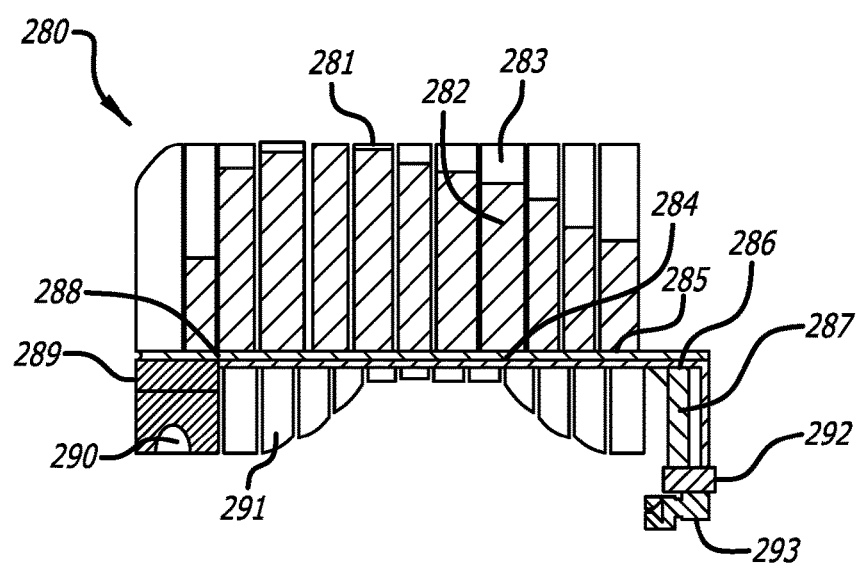
FIG. 69—Image showing another embodiment of the flag, with articulating vertical keys to provide radiation protection.

FIG. 69 demonstrates an embodiment of the flag 280 in which the radiation protection component of the flag is constructed of a series of rigid components or keys 281 that interlock and interact with one another. These keys 281 may be constructed of transparent material, opaque material or a combination of the two. Many of the keys have an element of transparent radiopaque glass 282 and an adjacent element of visually and radiation opaque material 283 rigidly attached to one another. These keys 281 are each attached to a lateral bar 284 by a hinge 285 that allows for rotational motion of the keys 218 about the axis of the lateral bar 284. The system contains a swivel 286 that allows the flag 280 to rotate about a vertical support bar 287. At the patient right arm side, there is a hinge 288 that allows for rotation about a vertical axis to adjust the shape of the flag 280. There are overlapping rigid plates 289 with a cutout for the patient arm 290 that allows for height adjustment. Below the lateral bar 284 there are elements of flexible radiopaque material 291 that allow for the shielding to accommodate the shape of the patient. There are also additional swivel elements 292 and 293 that provide for additional degrees of freedom, allowing rotation in horizontal and vertical planes respectively.

Figure 70:
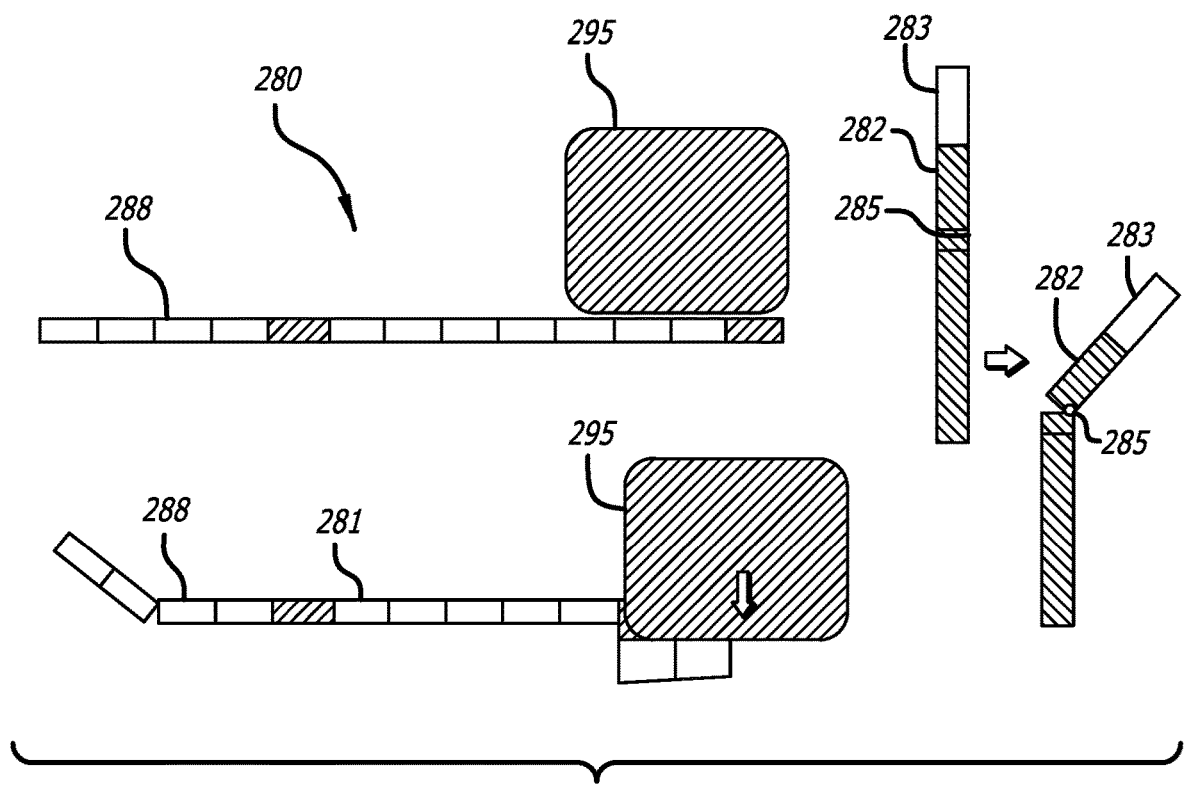
FIG. 70—Image showing overhead and side views of the keys relative to the x-ray detector.

FIG. 70 demonstrates how the flag embodiment 280 performs during use. The vertical hinge 288 allows the most lateral keys 281 of the flag to be flexed to accommodate the table and patient anatomy while continuing to provide good radiation protection to the health care staff. When the x-ray system 295 is advanced into contact with the flag 280, the keys of the flag 281 which are contacted by the x-ray system 295 flex about a lateral hinge 285, deflecting the key 281 which can consist of a radiopaque translucent component 282 and a radiopaque and visually opaque component 283.

Figure 71:
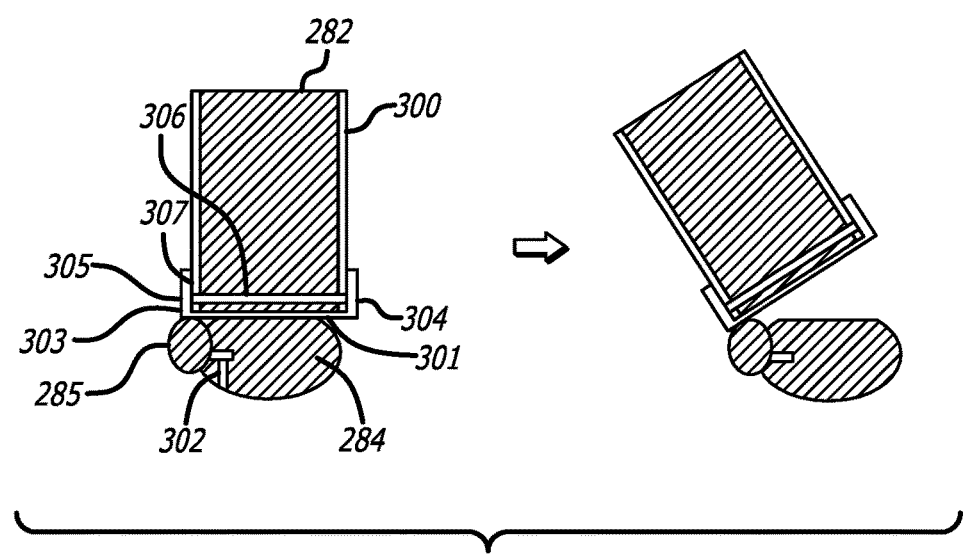
FIG. 71—Image showing mechanism that provides flexion of the rigid keys at the hinged base.

FIG. 71 describes the assembly details of one embodiment of the radiopaque key mechanism. The transparent radiopaque material 282 may be a leaded glass with a thickness of about 7 mm. This leaded glass is housed in a perimeter casing 300 of a polymer or other structurally protective material. A liner material 391 resides under the glass at the base of the key 281 to protect the glass from vibration or impact. The hinge 285 is mounted to the lateral arm 284 using a set screw mechanism 302. This hinge 285 is mounted to the glass casing 300 with a hinge hasp 303 that is bolted through the glass 282 into a receiving plate 304. The glass 282 is protected from the bolt 305 by a bearing sleeve 306 and a nylon spacer 307.

Figure 72:
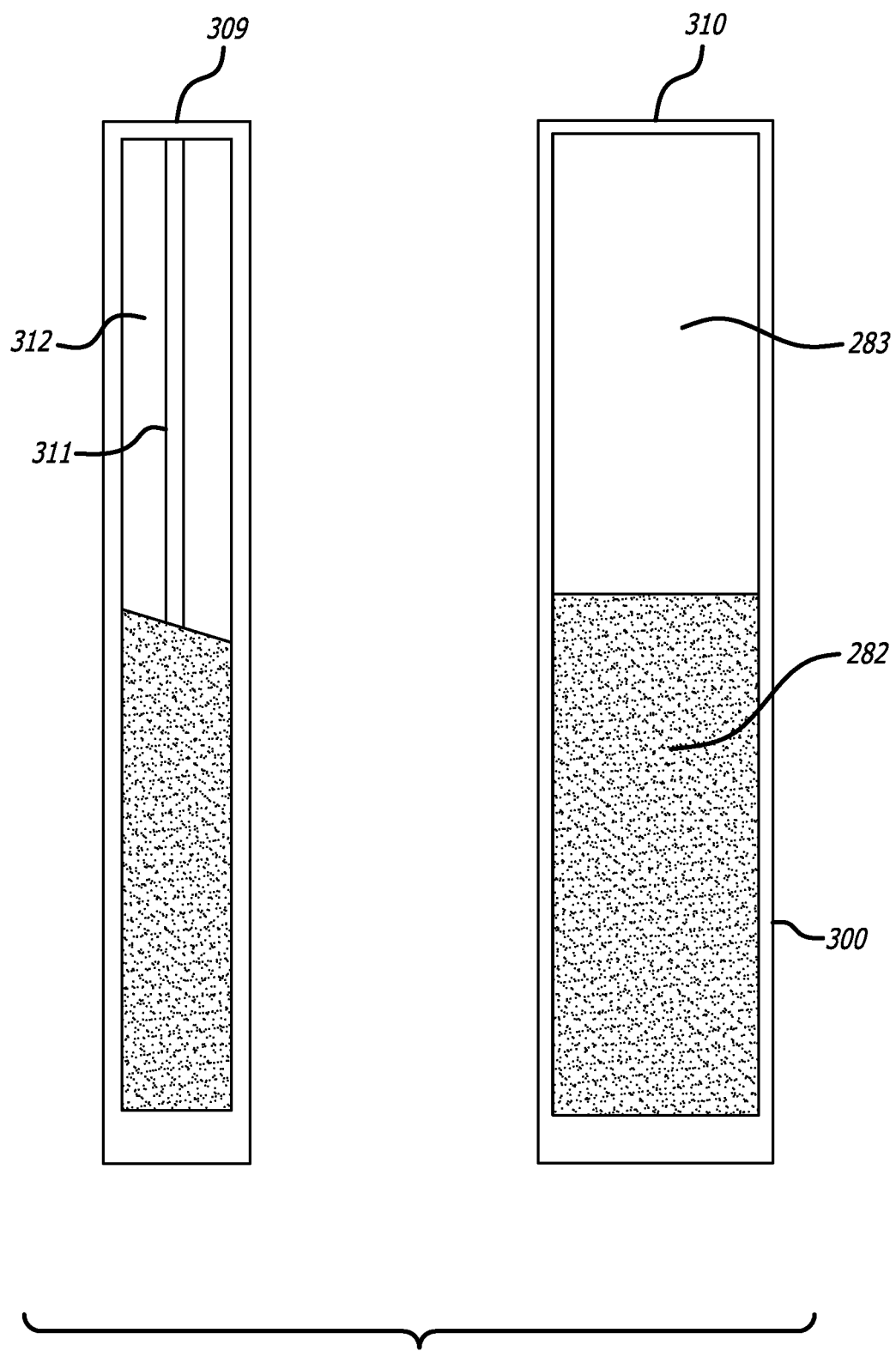
FIG. 72—Image showing integrated protection system to prevent keys from being damaged by contact from the x-ray detector.

FIG. 72 describes some detail as to the construction of the transparent/opaque assembly of the key 281. A front view 310 of the assembly shows the glass 282 and the opaque component 283 housed within a protective outer shell 300. A side view 309 of the assembly shows how an inner layer of radiopaque material 311 can be sandwiched within layers of a lightweight filler material 312 to create an assembly of constant thickness.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A mattress comprising:
   a soft comfort component that complies with a patient's body when the patient is lying on the mattress;
   a shell surrounding at least a lower surface of the comfort component and integral therewith, said shell being more rigid than the soft comfort component;
   a plurality of radiation shields placed to separate an operator from an imaging device, at least one of said plurality of radiation shields being flexible and connected to said mattress at a connected edge and configured with a free edge opposite the connected edge such that said flexible radiation shield will flex out of the way when contacted by the imaging device, wherein one of the plurality of shields is a workbench having sliding surfaces that allow dimensions of the workbench to be adjustable to fit different patient sizes; and,
   a guiderail system attached to the shell, the guiderail system including a guiderail providing an attachment surface usable to attach accessories to said guiderail.

2. The mattress of claim 1 wherein said shell surrounds a lower surface and at least a portion of at least one side surface of said soft comfort component.

3. The mattress of claim 1 wherein said soft comfort component includes a chest portion of increased stiffness to facilitate chest support during application of resuscitative chest compressions.

4. The mattress of claim 1 wherein said guiderail system further includes electrical lines integrated into said guiderails.

5. The mattress of claim 1 wherein said guiderail system further includes data lines integrated into said guiderails.

6. The mattress of claim 1 wherein said guiderail system further includes gas lines integrated into said guiderails.

7. A mattress system for use in a hospital comprising:
a mattress comprising:
a soft comfort component that complies with a patient's body when the patient is lying on the mattress;
a shell surrounding at least a lower surface of the comfort component and integral therewith, said shell being more rigid than the soft comfort component;
a plurality of radiation shields placed to separate an operator from an imaging device, at least one of said plurality of radiation shields being flexible and connected to said mattress at a connected edge and configured with a free edge opposite the connected edge such that said flexible radiation shield will flex out of the way when contacted by the imaging device;
a guiderail system attached to the shell, the guiderail system including a guiderail providing an attachment surface usable to attach accessories to said guiderail; and,
a radiation-shielding workbench having sliding surfaces that allow dimensions of the workbench to be adjustable to fit different patient sizes; and,
a latch and release mechanism slidably attachable to said guiderail such that, once attached to said guiderail, said component may be slid along said attachment surface to a desired location.

8. The mattress system of claim 7 wherein said shell surrounds a lower surface and at least a portion of at least one side surface of said soft comfort component.

9. The mattress system of claim 7 wherein said soft comfort component includes a chest portion of increased stiffness to facilitate chest support during application of resuscitative chest compressions.

10. The mattress system of claim 7 wherein said guiderail system further includes electrical lines integrated into said guiderails.

11. The mattress system of claim 7 wherein said guiderail system further includes data lines integrated into said guiderails.

12. The mattress system of claim 7 wherein said guiderail system further includes gas lines integrated into said guiderails.

13. The mattress system of claim 7 wherein said radiation shield includes a lateral unit that extends vertically from said latch and release mechanism when said latch and release mechanism is attached to said guiderail.

14. The mattress system of claim 13 wherein said radiation shield further includes an upper unit and a lower unit attached to said upper unit, wherein at least one of said upper and lower units are attached to said lateral unit.

15. The mattress system of claim 14 wherein said upper unit pivots vertically about said lower unit.

16. The mattress system of claim 15 wherein said upper unit includes vertical keys, thereby forming a plurality of vertical segments that may be positioned angled relative to each other.

* * * * *